(12) United States Patent
Jo et al.

(10) Patent No.: US 8,586,544 B2
(45) Date of Patent: Nov. 19, 2013

(54) CELL-PERMEABLE ENDOSTATIN RECOMBINANT PROTEIN, A POLYNUCLEOTIDE ENCODING THE SAME, AND AN ANTI-CANCER PREPARATION CONTAINING THE SAME AS AN ACTIVE COMPONENT

(75) Inventors: Daewoong Jo, Seoul (KR); Jong Min Lee, Suwon-si (KR); Kyoungho Park, Gwangju (KR); Minh Tam Duong, Seoul (KR)

(73) Assignees: Procell Therapeutics Inc., Seoul (KR); Daewoong Jo, Seoul (KR)

( * ) Notice: Subject to any disclaimer, the term of this patent is extended or adjusted under 35 U.S.C. 154(b) by 591 days.

(21) Appl. No.: 12/936,334

(22) PCT Filed: Apr. 3, 2009

(86) PCT No.: PCT/KR2009/001726
§ 371 (c)(1),
(2), (4) Date: Dec. 22, 2010

(87) PCT Pub. No.: WO2009/145489
PCT Pub. Date: Dec. 3, 2009

(65) Prior Publication Data
US 2011/0092441 A1    Apr. 21, 2011

Related U.S. Application Data

(60) Provisional application No. 61/042,312, filed on Apr. 4, 2008.

(51) Int. Cl.
*A61K 45/06* (2006.01)

(52) U.S. Cl.
USPC ........ 514/19.3; 514/21.2; 514/21.4; 530/324; 530/326

(58) Field of Classification Search
None
See application file for complete search history.

(56) References Cited

U.S. PATENT DOCUMENTS

| | | |
|---|---|---|
| 5,854,205 A | 12/1998 | O'Reilly et al. |
| 6,174,861 B1 | 1/2001 | O'Reilly et al. |
| 6,346,510 B1 | 2/2002 | O'Reilly et al. |
| 6,544,758 B2 | 4/2003 | O'Reilly et al. |
| 6,630,448 B2 | 10/2003 | O'Reilly et al. |
| 6,746,865 B1 | 6/2004 | O'Reilly et al. |
| 6,764,995 B2 | 7/2004 | O'Reilly et al. |
| 6,797,488 B1 | 9/2004 | Sukhatme |
| 6,852,691 B1 | 2/2005 | Sukhatme |
| 7,078,485 B2 | 7/2006 | Luo et al. |
| 7,101,979 B1 | 9/2006 | Boehm et al. |
| 7,179,608 B2 | 2/2007 | O'Reilly et al. |
| 7,470,667 B2 | 12/2008 | Luo et al. |
| 7,495,089 B2 | 2/2009 | O'Reilly et al. |
| 2002/0123458 A1 | 9/2002 | O'Reilly et al. |
| 2002/0127595 A1 | 9/2002 | O'Reilly et al. |
| 2003/0087393 A1 | 5/2003 | O'Reilly et al. |
| 2003/0114370 A1 | 6/2003 | Folkman et al. |
| 2003/0219426 A1 | 11/2003 | O'Reilly et al. |
| 2004/0005684 A1 | 1/2004 | Hung et al. |
| 2004/0102372 A1 | 5/2004 | O'Reilly et al. |
| 2005/0282253 A1 | 12/2005 | Folkman et al. |
| 2007/0134206 A1 | 6/2007 | Hung et al. |
| 2010/0197598 A1 | 8/2010 | Jo et al. |

FOREIGN PATENT DOCUMENTS

| | | |
|---|---|---|
| WO | 99 29855 | 6/1999 |
| WO | 99 62944 | 12/1999 |
| WO | 03 102187 | 12/2003 |
| WO | 2008 093982 | 8/2008 |

OTHER PUBLICATIONS

Extended European Search Report issued May 27, 2011, in European Patent Application No. 09754954.7.

Vladimir P. Torchilin, et al., "Peptide and Protein drug delivery to and into tumors: Challenges and solutions", Drug Discovery today, vol. 8, No. 6, XP-001197326, Mar. 15, 2003, pp. 259-266.

Aurélie Dutour, et al., "Endostatin cDNA/Cationic Liposome Complexes as a Promising Therapy to Prevent Lung Metastases in Osteosarcoma: Study in a Human-like Rat Orthotopic Tumor", Molecular Therapy, vol. 11, No. 2, XP-004723685, Feb. 1, 2005, pp. 311-319.

Joesun Ko, et al., "Development of novel peptides that mediate macromolecule intracellular transduction to live cells", 19th FAOBMB Seoul Conference, N-65, XP-002636065, May 27, 2007, 1 front page, p. 400.

Mauricio Rojas, et al., "Genetic engineering of proteins with cell membrane permeability", Nature Biotechnology, vol. 16, No. 4, XP-001118371, Apr. 1, 1998, pp. 370-375.

(Continued)

*Primary Examiner* — Cecilia J Tsang
*Assistant Examiner* — Li Lee
(74) *Attorney, Agent, or Firm* — Oblon, Spivak, McClelland, Maier & Neustadt, L.L.P.

(57) ABSTRACT

The present invention relates to a cell-permeable endostatin recombinant protein in which a macromolecule transduction domain (MTD) is fused to an angiogenesis inhibitor (angiogenesis inhibitor) endostatin; a polynucleotide encoding the cell-permeable endostatin recombinant protein; an expression vector for the cell-permeable endostatin recombinant protein; and a pharmacological composition for an anti-cancer preparation with improved inhibitory activity against angiogenesis in cancer, which contains the cell-permeable endostatin recombinant protein as an active component. The cell-permeable endostatin recombinant protein according to the present invention can block the formation of microvessels and inhibit the migration, proliferation, penetration, tube formation and the like of vascular endothelial cells present in tumor tissue by introducing the angiogenesis inhibitor endostatin into the cell with high efficiency, and it exhibits outstanding anti-cancer activity and so can be used as an anti-cancer drug against various cancers.

18 Claims, 23 Drawing Sheets

(56) References Cited

OTHER PUBLICATIONS

Steven R. Schwarze, et al., "In Vivo Protein Transduction: Delivery of a Biologically Active Protein into the Mouse", Science, vol. 285, No. 5433, XP-002140133, Sep. 3, 1999, pp. 1569 1572.

International Search Report issued Nov. 27, 2009 in PCT/KR09/001726 filed Apr. 3, 2009.

Hanai, J., et al., "Endostatin is a potential inhibitor of Wnt signaling," The Journal of Cell Biology, vol. 158, No. 3, pp. 529-539, (Aug. 5, 2002).

Jo, D., et al., "Epigenetic regulation of gene structure and function with a cell-permeable Cre recombinase," Nature Biotechnology, vol. 19, pp. 929-933, (Oct. 2001).

Sauter, B.V., et al., "Adenovirus-mediated gene transfer of endostatin in vivo results in high level of transgene expression and inhibition of tumor growth and metastases," PNAS, vol. 97, No. 9, pp. 4802-4807, (Apr. 25, 2000).

Coutinho, E.L., et al., "Anti-tumor effect of endostatin mediated by retroviral gene transfer in mice bearing renal cell carcinoma," The FASEB Journal, vol. 21, pp. 3153-3161, (Oct. 2007).

Derossi, D., et al., "Cell Internalization of the Third Helix of the Antennapedia Homeodomain Is Receptor-independent," The Journal of Biological Chemistry, vol. 271, No. 30, pp. 18188-18193, (Jul. 26, 1996).

Skovseth, D.K., et al., "Endostatin dramatically inhibits endothelial cell migration, vascular morphogenesis, and perivascular cell recruitment in vivo," Hemostasis, Thrombosis, and Vascular Biology, Blood, vol. 105, No. 3, pp. 1044-1051, (Feb. 1, 2005).

Bertolini, F., et al., "Endostatin, an antiangiogenic drug, induces tumor stabilization after chemotherapy or anti-CD20 therapy in a NOD/SCID mouse model of human high-grade non-Hodgkin lymphoma," Neoplasia, Blood, vol. 96, No. 1, pp. 282-287, (Jul. 1, 2000).

Kikuchi, E., et al., "Inhibition of Orthotopic Human Bladder Tumor Growth by Lentiviral Gene Transfer of Endostatin," Clinical Cancer Research, vol. 10, pp. 1835-1842, (Mar. 1, 2004).

Joliot, A., et al., "Transduction peptides, from technology to physiology," Nature Cell Biology, vol. 6, No. 3, pp. 189-196, (Mar. 2004).

Suzuki, T., et al., "Possible Existence of Common Internalization Mechanisms among Arginine-rich Peptides," The Journal of Biological Chemistry, vol. 277, No. 4, pp. 2437-2443, (Jan. 25, 2002).

Wadia, J.S., et al., "Transducible TAT-HA fusogenic peptide enhances escape of TAT-fusion proteins after lipid raft macropinocytosis," Nature Medicine, vol. 10, No. 3, pp. 310-315, (Mar. 2004).

FIG. 1B

Full-length CP-Endostatin fused JO-66 MTD (MTD3)
HM$_3$E (HM$_3$E-5', HE-3')

Full-length CP-Endostatin fused JO-71 MTD (MTD4)
HM$_4$E (HM$_4$E-5', HE-3')

Full-length CP-Endostatin fused JO-85 MTD (MTD5)
HM$_5$E (HM$_5$E-5', HE-3')

Full-length CP-Endostatin fused JO-18 MTD (MTD6)
HM$_6$E (HM$_6$E-5', HE-3')

Full-length CP-Endostatin fused JO-41 MTD (MTD7)
HM$_7$E (HM$_7$E-5', HE-3')

Full-length CP-Endostatin fused JO-135 MTD (MTD8)
HM$_8$E (HM$_8$E-5', HE-3')

Full-length CP-Endostatin fused JO-159 MTD (MTD9)
HM$_9$E (HM$_9$E-5', HE-3')

- His-tag (18aa)
- JO-66 MTD (10 aa)
- JO-71 MTD (9 aa)
- JO-71 MTD (11 aa)
- JO-18 MTD (16 aa)
- JO-41 MTD (8 aa)
- JO-135 MTD (10 aa)
- JO-159 MTD (12 aa)

M₁: JO-56 MTD
M₂: JO-73 MTD

M: 1 kb Marker
1: HE — -612 bp
2: HM₁E — -639 bp
3: HEM₁ — -639 bp
4: HM₁EM₁ — -666 bp
5: HM₂E — -636 bp
6: HEM₂ — -636 bp
7: HM₂EM₂ — -660 bp

M₁: JO-56 MTD
M₂: JO-73 MTD

M: 100 bp Marker
1: HE        -612 bp
2: HM₁E      -639 bp
3: HEM₁      -639 bp
4: HM₁EM₁    -666 bp
5: HM₂E      -636 bp
6: HEM₂      -636 bp

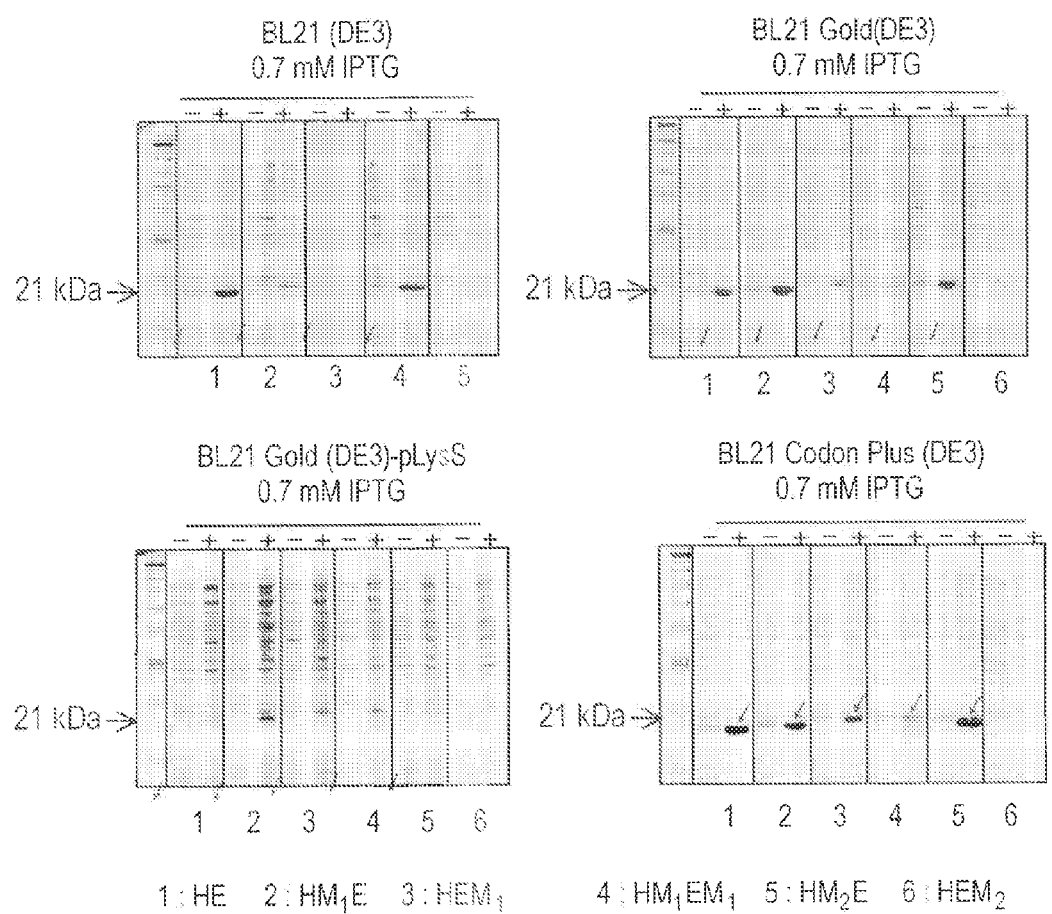

1: HM$_3$E  2: HM$_4$E  3: HM$_5$E  4: HM$_6$E
5: HM$_7$E  6: HM$_8$E  7: HM$_9$E

|  | HE | HM$_1$E | HEM$_1$ | HM$_1$EM$_1$ | HM$_2$E |
| --- | --- | --- | --- | --- | --- |
| Size (aa) | 204 | 213 | 213 | 222 | 212 |
| Yield (mg/L) | 18 | 13 | 10 | 10 | 13 |

FIG. 7A
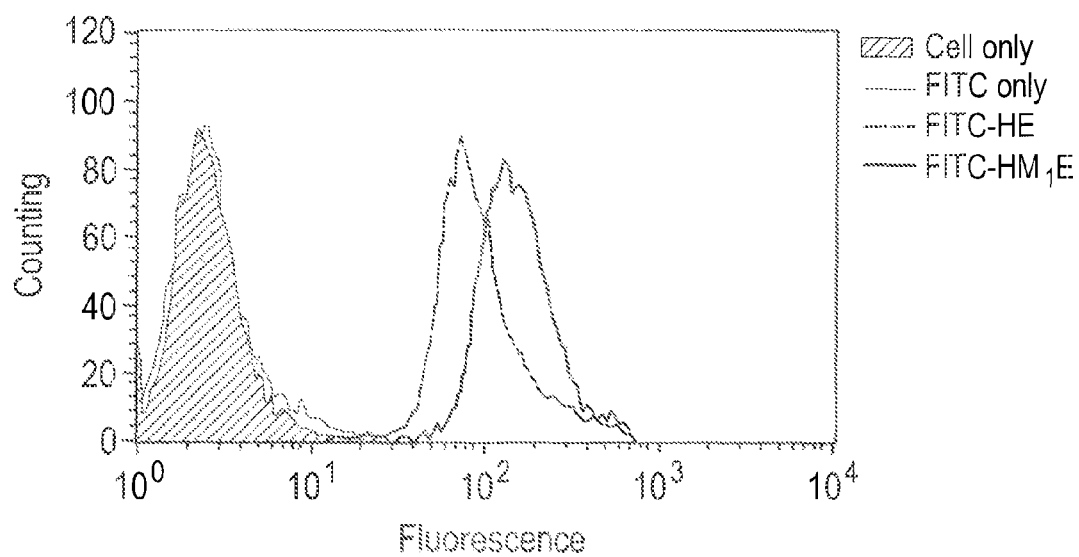
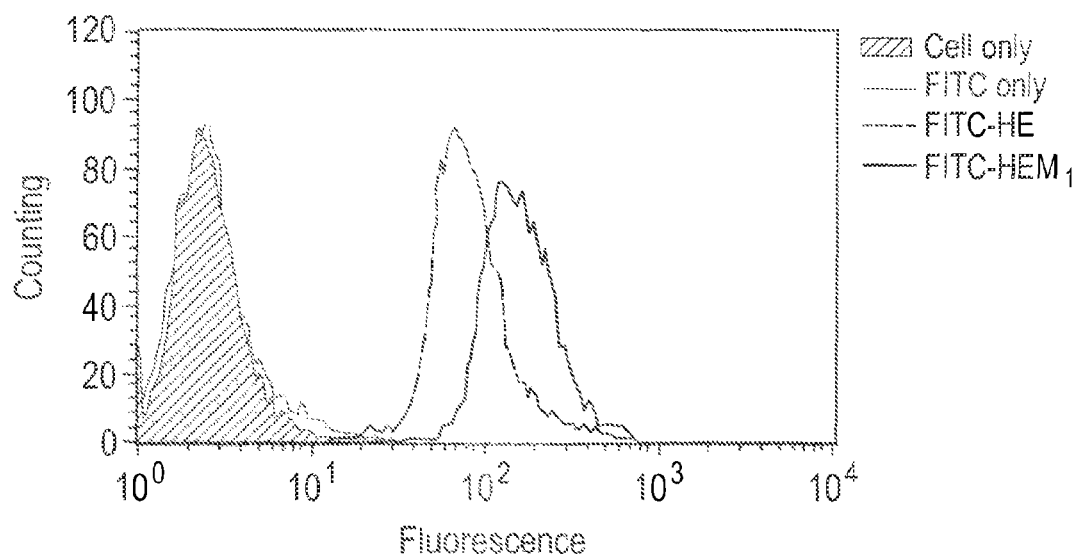

FIG. 7B
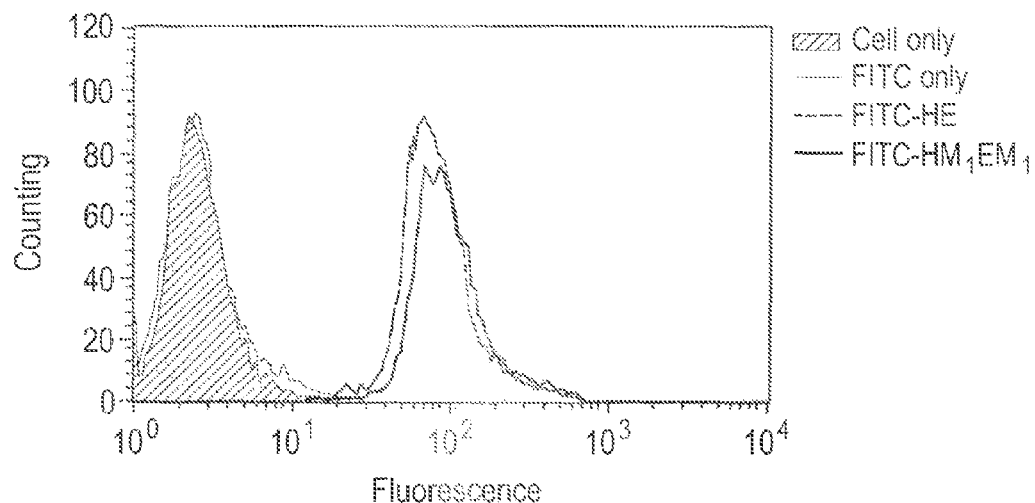
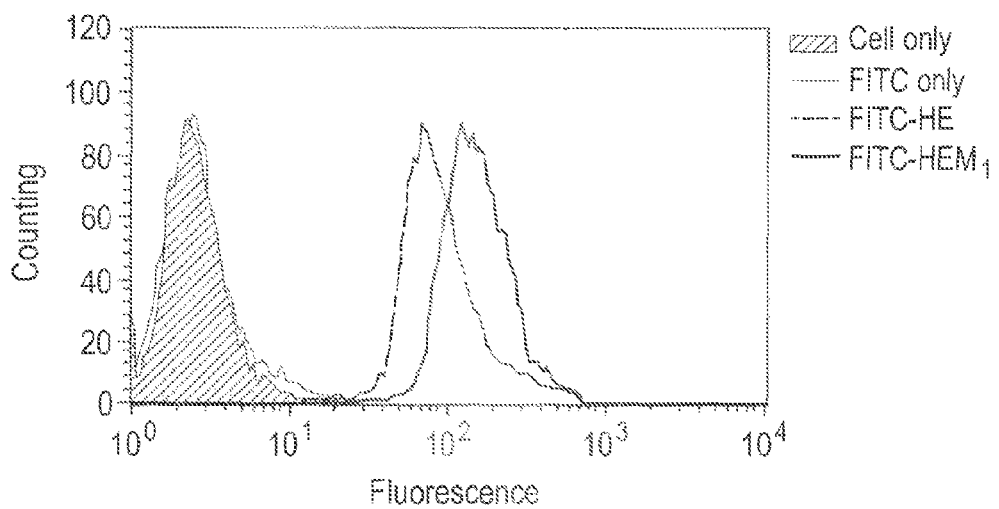

FIG. 10

| Endostatin protein | – | | HE | HM₁E | JO-56 MTD | | | | JO-73 MTD | |
|---|---|---|---|---|---|---|---|---|---|---|
| | | | | | HM₁E | HEM₁ | HM₁EM₁ | | HM₂E | |
| beta-catenin ratio | 1 | | 1.0 | 0.9 | 0.9 | | 0.2 | | 0.2 | |
| c-Myc ratio | 1 | | 1.6 | 1.3 | 2.1 | | 1.2 | | 0.8 | |
| STAT3 ratio | 1 | | 1.1 | 1.0 | 0.6 | | 0.7 | | 0.01 | |
| VEGF ratio | 1 | | 1.4 | 1.1 | 1.1 | | 0.7 | | 0.7 | |
| p-ERK ratio | 1 | | 1 | 0.9 | 1.7 | | 1.4 | | 0.1 | |
| beta-actin | | | | | | | | | | |

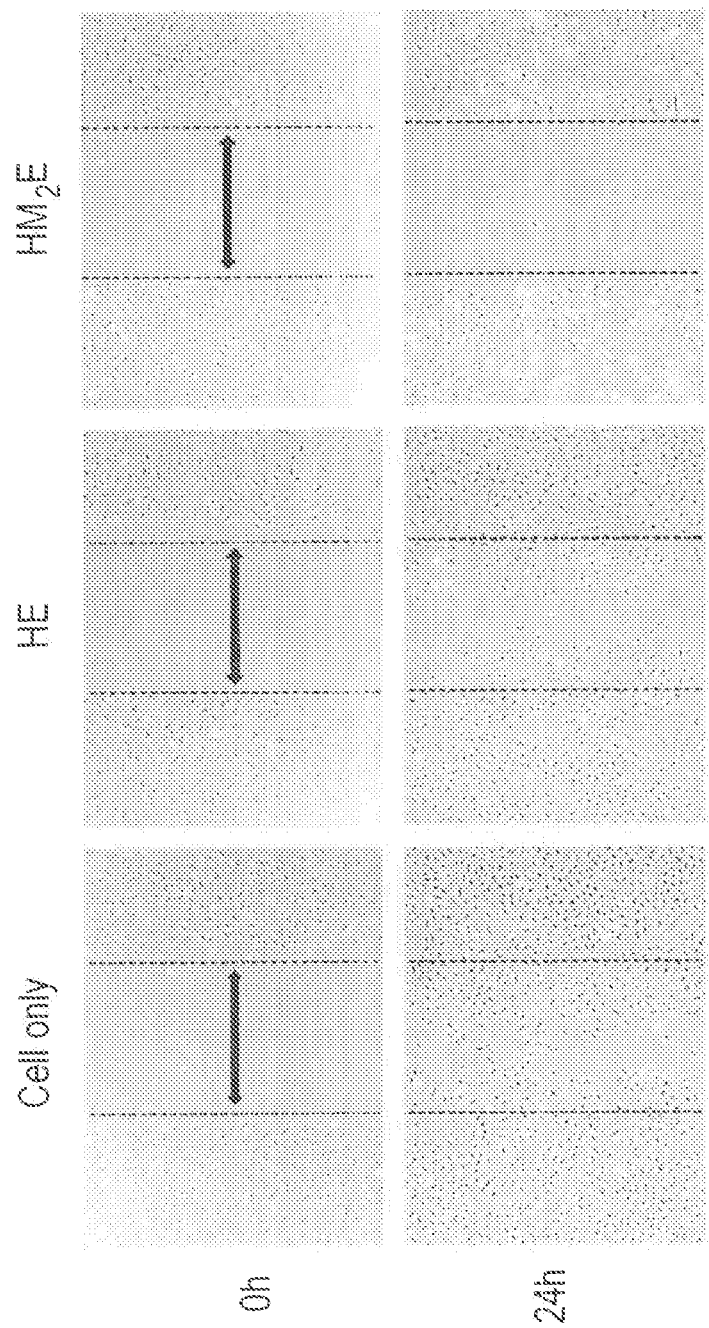

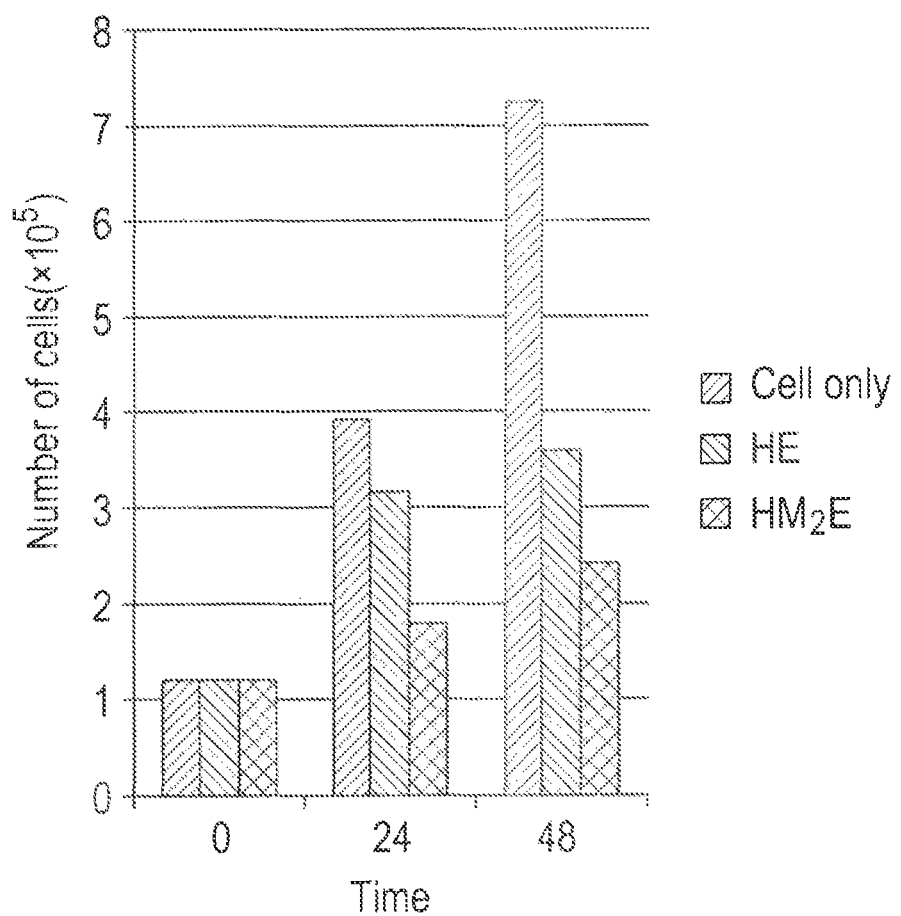

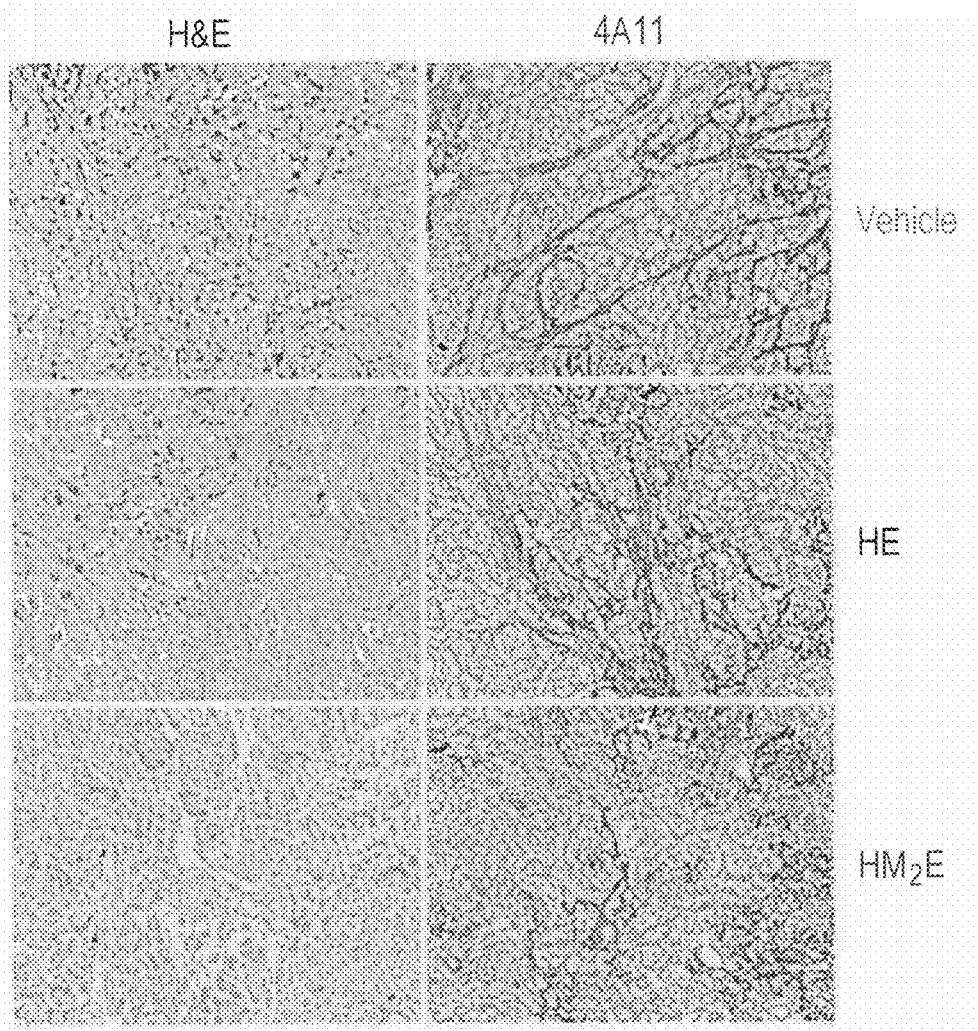

CELL-PERMEABLE ENDOSTATIN RECOMBINANT PROTEIN, A POLYNUCLEOTIDE ENCODING THE SAME, AND AN ANTI-CANCER PREPARATION CONTAINING THE SAME AS AN ACTIVE COMPONENT

FIELD OF THE INVENTION

The present invention relates to a cell-permeable endostatin recombinant protein in which a macromolecule transduction domain (MTD) is fused to an angiogenesis inhibitor endostatin, a polynucleotide encoding the cell-permeable endostatin recombinant protein, an expression vector of the cell-permeable endostatin recombinant protein, and a pharmacological composition for use as an anti-cancer agent with improved cancer angiogenesis inhibiting activity comprising the cell-permeable endostatin recombinant protein as an active ingredient.

BACKGROUND OF THE INVENTION

Angiogenesis, the process by which new capillaries are formed from pre-existing blood vessels, is essential for the growth and persistence of solid tumors and their metastases. Pathogenic angiogenesis plays an important role in the progression of diseases, such as cancer, diabetic retinopathy, psoriasis, rheumatoid arthritis, etc. Under stable conditions, vascular endothelial cells exist in a quiescent state while maintaining a relatively slow turnover. The switch involving the conversion of quiescent endothelial cells to an active pro-angiogenic phenotype requires both the up-regulation of endogenous angiogenesis stimulators and the down-regulation of endogenous angiogenesis inhibitors. Such angiogenesis stimulators may include, for example, bFGF, VEGF, vascular permeability factors, and the like, while endogenous angiogenesis inhibitors may include, for example, angiostatin, endostatin, tumstatin, canstatin, arresten, thrombospondin, and the like.

Among these angiogenesis inhibitors, endostatin is a 20 kDa polypeptide derived from collagen XVIII and an endogenous anti-angiogenesis protein that inhibits endothelial cell proliferation, migration, invasion, tube formation, etc. Endostatin is released from the collagenous domain by cleavage within the protease-sensitive hinge region by enzymes, such as elastase and cathepsin, and circulates in the blood at a concentration of from 20 to 35 ng/ml. Endostatin specifically binds to a specific integrin and inhibits the phosphorylation of focal adhesion kinase (FAK). The inhibition of FAK phosphorylation by the binding of endostatin to integrin leads to the blocking of the downstream MAP kinase pathway, resulting in the inhibition of ERK1 and p38 MAP kinase pathways. This inhibition blocks the migration of endothelial cells.

Recently, another hypothesis has been suggested to explain the function of endostatin as a putative inhibitor of the Wnt signalling pathway (Hanai et al., *JCB* 158:529, 2002). Wnt signaling is important for the regulation of cell proliferation, differentiation, motility and morphogenesis. Endostatin modulates the Wnt signalling pathway by regulating β-catenin stability via a novel GSK3-independent mechanism. That effect of endostatin on the Wnt signalling pathway triggers the inhibition of endothelial cell migration and induces the entry into the S phase of the cell cycle, which is related to angiogenesis inhibitory activity. Thus, rather than directly affecting the tumor tissue, endostatin indirectly affects the tumor tissue by suppressing new blood vessel construction and blood supply into tumor tissue, which makes it an attractive target for anticancer drug development.

Therefore, a number of clinical approaches have been tried to use endostatin, an anti-angiogenesis agent, for treatment of cancer in humans, but there has not been any positive outcome so far. The in vivo pharmacokinetics of endostatin and the administration mode which has a great impact on efficacy are considered as major obstacles preventing success in clinical trials using endostatin.

According to previous studies, in order for endostatin to be activated in vivo, endostatin must be 1) expressed from a bacterial expression system in a soluble form; 2) capable of being purified in large quantities; 3) capable of being directly administered into the body of the test animal with an injection tool; 4) capable of being maintained at a considerably high in vivo concentration by means of non-continuous direct injection. When such requirements are met, endostatin can function as a critical factor in inducing the apoptosis of cancer cells by inhibiting angiogenesis in tumor tissues.

Meanwhile, small molecules derived from synthetic compounds or natural compounds are capable of being transported into the cells, whereas macromolecules, such as proteins, peptides, and nucleic acids, cannot. It is widely understood that macromolecules larger than 500 kDa are incapable of penetrating the plasma membrane, i.e., the lipid bilayer structure, of living cells. In order to overcome this problem, "macromolecule intracellular transduction technology (MITT)" was developed (Jo et al., *Nat. Biotech.* 19: 929-33, 2001), which allows the delivery of therapeutically effective macromolecules into cells, making the development of new drugs using peptides, proteins and genetic materials possible. According to this method, if a target macromolecule is fused to a "hydrophobic macromolecule transduction domain (MTD)" and other cellular delivery regulators, synthesized, expressed, and purified in the form of a recombinant protein, it can penetrate the plasma membrane lipid bilayer of the cells, be accurately delivered to a target site, and then, effectively exhibit its therapeutic effect (U.S. Provisional Patent Application No. 60/887,060; PCT International Publication No. WO 2008/093982). Such MTDs are fused to peptides, proteins, DNA, RNA, synthetic compounds, and the like, facilitating the transport of many impermeable materials into the cells.

Accordingly, the inventors of the present invention have developed an endostatin recombinant protein (CP-endostatin) imparted with cell permeability by fusing the angiogenesis inhibitor endostatin to a MTD and found that this recombinant protein effectively delivered a large amount of endostatin into a cell in vivo as well as in vitro to suppress the formation of microvessels and can be used in the treatment of various cancers in humans.

SUMMARY OF THE INVENTION

Therefore, the objective of the present invention is to provide a cell permeable endostatin recombinant protein by imparting the angiogenesis inhibitor endostatin with cell permeability and introducing the endostatin into a cell with high efficiency, whereby the recombinant protein can be used as an anticancer agent capable of treating various cancers in humans.

In order to achieve the above objective, the present invention provides a cell permeable endostatin recombinant protein capable of imparting endostatin with cell permeability by fusing a macromolecule transduction domain (MTD) to endostatin, and thereby introducing endostatin into a cell with high efficiency.

The present invention also provides a polynucleotide encoding the above cell permeable endostatin recombinant protein.

The present invention further provides an expression vector comprising the above polynucleotide and a transformant transformed with such expression vector.

In addition, the present invention provides a method of producing cell permeable endostatin recombinant proteins comprising culturing the above transformants.

Lastly, the present invention provides a pharmaceutical composition for use as an anticancer agent with improved cancer angiogenesis inhibiting activity comprising the above cell permeable endostatin recombinant protein as an active ingredient.

BRIEF DESCRIPTION OF THE DRAWINGS

FIG. 1b illustrates the structures of the endostatin recombinant proteins, each being fused to one of JO-66, JO-71, JO-85, JO-18, JO-41, JO-135, and JO-159 MTDs and designed in a full-length form according to the present invention.

FIG. 5a shows the results from examining the expression of the cell permeable endostatin recombinant proteins according to the present invention in various host cells.

FIGS. 7a and 7b are the results from flow cytometry analysis of cell permeabilities of the cell permeable endostatin recombinant proteins according to the present invention.

FIG. 10 is a photograph of a western blot analysis showing the in vivo function of the cell permeable endostatin recombinant proteins according to the present invention.

FIG. 11 shows the results from a wound healing analysis showing the inhibitory effect of the cell permeable endostatin recombination protein according to the present invention on human endothelial cell migration.

FIGS. 12a and 12b are graphs illustrating the inhibitory effect of the cell permeable endostatin recombination protein according to the present invention on human endothelial cell proliferation by counting the number of cells after a period of time.

FIG. 15 is a photograph of immunohistrochemical staining showing the inhibitory effect on angiogenesis in a tumor tissue extracted from a mouse administered with the cell permeable endostatin recombinant protein according to the present invention via subcutaneous injection.

DETAILED DESCRIPTION OF THE INVENTION

The present invention provides cell permeable endostatin recombinant proteins (CP-endostatin) in which a macromolecule transduction domain (MTD) is fused to the angiogenesis inhibitor endostatin, whereby the endostatin is imparted with cell permeability and then introduced into a cell with high efficiency and polynucleotides encoding the same.

The present invention is characterized in that the angiogenesis inhibitor endostatin, which is a macromolecule incapable of being introduced into a cell, is fused to a specific macromolecule transduction domain (hereinafter, "MTD") by using MITT so as to be imparted with cell permeability, and thus, can be transported into a cell with high efficiency. The MTD can be fused to only one terminus or both termini of the endostatin. MITT, which exploits a hydrophobic polypeptide MTD that is derived from a secreted protein, enables real-time quantitative regulation of the in vivo concentration of endostatin, thereby allowing endostatin to be delivered into tumor tissues and distributed to individual cancer cells. This effect may allow endostatin to be maintained at a high concentration inside and outside of the endothelial cells present in cancer tissue, thereby inducing the binding of endostatin to the specific receptor (integrin $\alpha 5\beta 1$) present on the surface of the endothelial cells in tumor tissues. Thus, the migration, proliferation, invasion, and tube formation of the endothelial cells are effectively suppressed and the formation of new microvessels is blocked in tumor tissues, thereby leading to an environment favorable for cancer treatment.

The present invention has developed cell permeable endostatin recombinant proteins that are constructed by fusing endostatin to a peptide domain capable of transporting a macromolecule into a cell, i.e., MTD.

The term "cell permeable recombinant protein" as used herein refers to a complex comprising a MTD and the angiogenesis inhibitor endostatin, where they are linked by genetic fusion or chemical coupling. The term "genetic fusion" used herein refers to a linear, covalent linkage of proteins generated through genetic expression of a polynucleotide (DNA sequence) molecule encoding proteins.

Endostatin, which binds to a specific integrin ($\alpha 5\beta 1$) present on the surface of endothelial cells and inhibits migration, proliferation, invasion, tube formation, etc., of the endothelial cells, functions as an anti-angiogenesis protein having a nucleotide sequence represented by SEQ ID NO: 1 and an amino acid sequence represented by SEQ ID NO: 2.

Figure 1A:
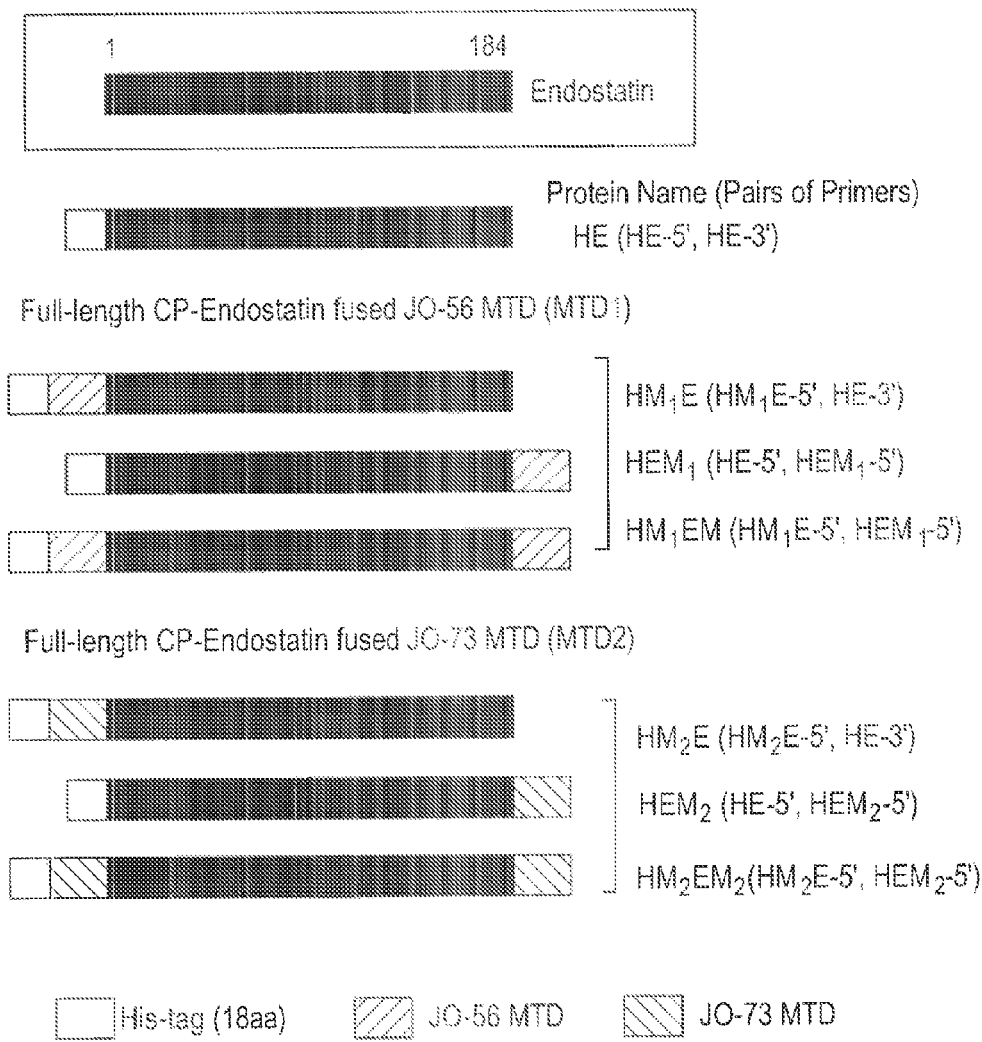
FIG. 1a illustrates the structure of the endostatin recombinant proteins, each being fused to one of JO-56 and JO-73 MTDs and designed in a full-length form according to the present invention.

The angiogenesis inhibitor endostatin is a 20-kDa C-terminal fragment derived from collagen XVIII by cleavage by enzymes, such as elastase and cathepsin, and has an amino acid sequence represented by SEQ ID NO: 2 (see FIG. 1a).

As the MTD capable of being fused to the angiogenesis inhibitor endostatin, cell permeable peptides having an amino acid sequence selected from the group consisting of SEQ ID NOS: 3 to 11 may be used. MTDs having one of the amino acid sequences represented by SEQ ID NOS: 3 to 11 are cell permeable polypeptides capable of mediating the transport of a biologically active molecule, such as a polypeptide, a protein domain, or a full-length protein, across the cell membrane. The MTD according to the present invention includes a hydrophobic region providing cell membrane targeting activity by forming a helix at a signal peptide comprising three domains, i.e., an N-terminal domain, a hydrophobic domain and a C-terminal domain containing a secreted protein cleavage site. These MTDs can directly penetrate the cell membrane while avoiding any cell damage and deliver a target protein into a cell, allowing it to exhibit its desired function.

The MTDs having the amino acid sequences represented by SEQ ID NOS: 3 to 11 and capable of being fused to the angiogenesis inhibitor endostatin according to the present invention are summarized in Table 1 below.

In some embodiments of the present invention, one of the following MTDs:

a JO-56 MTD having the amino acid sequence represented by SEQ ID NO: 5 which is a peptidyl-prolyl cis-trans isomerase B precursor derived from the Cyclophilin B protein (hereinafter, "$MTD_1$");

a JO-73 MTD having the amino acid sequence represented by SEQ ID NO: 8 which is a spatzle (spz) gene derived from *Drosophila melanogaster* (hereinafter, "$MTD_2$");

a JO-66 MTD having the amino acid sequence represented by SEQ ID NO: 6 which is a secreted protein derived from *Streptomyces coelicolor* A3(2) (hereinafter, "$MTD_3$");

a JO-71 MTD having the amino acid sequence represented by SEQ ID NO: 7 which is derived from the Neuroplastin precursor (hereinafter, "$MTD_4$");

a JO-85 MTD having the amino acid sequence represented by SEQ ID NO: 9 which is a peptide transport system secreted peptide binding protein derived from *Streptomyces coelicolor* (hereinafter, "$MTD_5$");

a JO-18 MTD having the amino acid sequence represented by SEQ ID NO: 3 which is a putative secreted protein derived from *Streptomyces coelicolor* A3(2) (hereinafter, "$MTD_6$");

a JO-41 MTD having the amino acid sequence represented by SEQ ID NO: 4 which is a secreted protein derived from *Streptomyces coelicolor* A3(2) (hereinafter, "$MTD_7$");

a JO-135 MTD having the amino acid sequence represented by SEQ ID NO: 10 which is a secreted ATP/GTP binding protein derived from *Streptomyces coelicolor* A3(2) (hereinafter, "$MTD_8$"); and a JO-159 MTD having the amino acid sequence represented by SEQ ID NO: 11 which is a Foldase protein prsA precursor (hereinafter, "$MTD_9$"), is used as the MTD capable of being fused to the angiogenesis inhibitor endostatin.

The cell permeable endostatin recombinant proteins according to the present invention may have a structure where

TABLE 1

| MTD | Origin | Amino acid sequence | SEQ ID NO |
|---|---|---|---|
| JO-18 | CAB38593 putative secreted protein [*Streptomyces coelicolor* A3(2)] | Ala Ala Leu Ala Leu Gly Val Ala Ala Ala Pro Ala Ala Ala Pro Ala | 3 |
| JO-41 | NP_626993 secreted protein [*Streptomyces coelicolor* A3(2)] | Ala Ala Ala Leu Leu Ala Val Ala | 4 |
| JO-56 | P23284 Peptidyl-prolyl cis-trans isomerase B precursor (PPIase) (Rotamase) (Cyclophilin B) | Val Leu Leu Ala Ala Ala Leu Ile Ala | 5 |
| JO-66 | NP_626568 secreted protein [*Streptomyces coelicolor* A3(2)] | Ala Ala Ala Leu Ala Ala Ile Ala Val Ile | 6 |
| JO-71 | P97300 Neuroplastin precursor (Stromal cell-derived receptor 1) (SDR-1) | Ala Leu Ala Leu Leu Leu Leu Val Pro | 7 |
| JO-73 | AAA17887 *Drosophila melanogaster* spatzle (spz) gene | Pro Val Leu Leu Leu Leu Ala Pro | 8 |
| JO-85 | NP_629842 peptide transport system secreted peptide binding protein [*Streptomyces coelicolor* A3(2)] | Leu Leu Ala Ala Ala Ala Ala Leu Leu Leu Ala | 9 |
| JO-135 | NP_733682 secreted ATP/GTP binding protein [*Streptomyces coelicolor* A3(2)] | Ala Ala Val Ala Leu Pro Ala Ala Ala Pro | 10 |
| JO-159 | P24327 Foldase protein prsA precursor | Ile Ala Ile Ala Ala Ile Pro Ala Ile Leu Ala Leu | 11 | one of the nine MTDs above (JO-56 MTD: MTD$_1$; JO-73 MTD: MTD$_2$; JO-66 MTD: MTD$_3$; JO-71 MTD: MTD$_4$; JO-85 MTD: MTD$_5$; JO-18 MTD: MTD$_6$; JO-41 MTD: MTD; JO-135 MTD: MTD$_8$; and JO-159 MTD: MTD$_9$) is fused to one terminus or both termini of the angiogenesis inhibitor endostatin and a histamine-tag (His-Tag) affinity domain can be fused to one terminus of this fusion construct for the facilitation of purification.

In one embodiment of the present invention, three full-length forms of endostatin recombinant proteins using a JO-56 MTD and three full-length forms of endostatin recombinant proteins using a JO-73 MTD may be designed. In other embodiments of the present invention, a full-length form of an endostatin recombinant protein may be designed for each of the remaining seven MTDs.

As used herein, the term "full-length form" refers to a form including a C-terminal domain of collagen XVIII having all amino acid residues 1 to 184 of the amino acid sequence of SEQ ID NO: 2.

Referring to FIG. 1a, the full-length forms of the cell permeable endostatin recombinant proteins according to the present invention in which a JO-56 MTD is fused are as follows:
1) HM$_1$E, where a JO-56 MTD is fused to the N-terminus of a full-length endostatin,
2) HEM$_1$, where a JO-56 MTD is fused to the C-terminus of a full-length endostatin, and
3) HM$_1$EM$_1$ where a JO-56 MTD is fused to both termini of a full-length endostatin, where a His-Tag is covalently coupled to the N-terminus of all of the above recombinant constructs.

In the full-length forms of the endostatin recombinant proteins described above, HM$_1$E has an amino acid sequence represented by SEQ ID NO: 15, which is encoded by a polynucleotide having a nucleotide sequence represented by SEQ ID NO: 14; HEM$_1$ has an amino acid sequence represented by SEQ ID NO: 17, which is encoded by a polynucleotide having a nucleotide sequence represented by SEQ ID NO: 16; and HM$_1$EM$_1$ has an amino acid sequence represented by SEQ ID NO: 19, which is encoded by a polynucleotide having a nucleotide sequence represented by SEQ ID NO: 18.

In addition, the full-length forms of the cell permeable endostatin recombinant proteins according to the present invention in which a JO-73 MTD is fused are as follows:
1) HM$_2$E, where a JO-73 MTD is fused to the N-terminus of a full-length endostatin,
2) HEM$_2$, where a JO-73 MTD is fused to the C-terminus of a full-length endostatin, and
3) HM$_2$EM$_2$ where a JO-73 MTD is fused to both termini of a full-length endostatin, where a His-Tag is covalently coupled to the N-terminus of all of the above constructs.

In the full-length forms of the endostatin recombinant proteins described above, HM$_2$E has an amino acid sequence represented by SEQ ID NO: 21, which is encoded by a polynucleotide having a nucleotide sequence represented by SEQ ID NO: 20; HEM$_2$ has an amino acid sequence represented by SEQ ID NO: 23, which is encoded by a polynucleotide having a nucleotide sequence represented by SEQ ID NO: 22; and HM$_2$EM$_2$ has an amino acid sequence represented by SEQ ID NO: 25, which is encoded by a polynucleotide having a nucleotide sequence represented by SEQ ID NO: 24.

In another embodiment of the present invention, seven full-length forms of cell permeable endostatin recombinant proteins using a JO-66 MTD, a JO-71 MTD, a JO-85 MTD, a JO-18 MTD, a JO-41 MTD, a JO-135 MTD, and a JO-159 MTD, respectively, may be designed.

Referring to FIG. 1b, the full-length forms of the endostatin recombinant proteins according to the present invention, which are fused to any one of JO-66, JO-71, JO-85, JO-18, JO-41, JO-135, and JO-159 MTDs are as follows:
1) HM$_3$E, where a JO-66 MTD is fused to the N-terminus of a full-length endostatin;
2) HM$_4$E, where a JO-71 MTD is fused to the N-terminus of a full-length endostatin;
3) HM$_5$E, where a JO-85 MTD is fused to the N-terminus of a full-length endostatin;
4) HM$_6$E, where a JO-18 MTD is fused to the N-terminus of a full-length endostatin;
5) HM$_7$E, where a JO-41 MTD is fused to the N-terminus of a full-length endostatin;
6) HM$_8$E, where a JO-135 MTD is fused to the N-terminus of a full-length endostatin; and
7) HM$_9$E, where a JO-159 MTD is fused to the N-terminus of a full-length endostatin, where a His-Tag is covalently coupled to the N-terminus of all of the above recombinant constructs.

In the full-length forms of the endostatin recombinant proteins described above, HM$_3$E has an amino acid sequence represented by SEQ ID NO: 27, which is encoded by a polynucleotide having a nucleotide sequence represented by SEQ ID NO: 26; HM$_4$E has an amino acid sequence represented by SEQ ID NO: 29, which is encoded by a polynucleotide having a nucleotide sequence represented by SEQ ID NO: 28; HM$_5$E has an amino acid sequence represented by SEQ ID NO: 31, which is encoded by a polynucleotide having a nucleotide sequence represented by SEQ ID NO: 30; HM$_6$E has an amino acid sequence represented by SEQ ID NO: 33, which is encoded by a polynucleotide having a nucleotide sequence represented by SEQ ID NO: 32; HM$_7$E has an amino acid sequence represented by SEQ ID NO: 35, which is encoded by a polynucleotide having a nucleotide sequence represented by SEQ ID NO: 34; HM$_8$E has an amino acid sequence represented by SEQ ID NO: 37, which is encoded by a polynucleotide having a nucleotide sequence represented by SEQ ID NO: 36; and HM$_9$E has an amino acid sequence represented by SEQ ID NO: 39, which is encoded by a polynucleotide having a nucleotide sequence represented by SEQ ID NO: 38.

As a control to be compared with the cell permeable endostatin recombinant proteins, an endostatin recombinant protein HE in which endostatin is fused only to a His-Tag with no MTD fused thereto may be prepared. The control protein has an amino acid sequence represented by SEQ ID NO: 13, which is encoded by a polynucleotide having a nucleotide sequencer represented by SEQ ID NO: 12.

Further, the present invention provides a recombinant expression vector comprising the polynucleotide encoding the cell permeable endostatin recombinant proteins described above, and a transformant which is transformed with such expression vector.

The term "expression vector" as used herein, which is a vector capable of expressing target protein or a target RNA in a suitable host cell, refers to a genetic structure which is operably linked to necessary regulatory elements such that a genetic insert can be expressed.

As used herein, the term "operably linked" means that a nucleotide sequence encoding a target protein or a target RNA is functionally linked to the regulatory sequence in a manner which allows for the expression of the nucleotide sequence.

For example, if a promoter is functionally linked to a nucleotide sequence encoding a protein or RNA, the expression of the nucleotide sequence may be affected. An operable linkage with an expression vector can be achieved by conventional gene recombinant techniques known in the art, while site-specific DNA cleavage and linkage are carried out by using conventional enzymes.

The expression vectors that can be used in the present invention may include, but are not limited to, plasmid vectors, cosmid vectors, bacteriophage vectors, viral vectors, etc. Suitable expression vectors may include a signal sequence or a leader sequence for membrane targeting or secretion, as well as regulatory sequences such as a promoter, an operator, an initiation codon, a termination codon, a polyadenylation signal, an enhancer and the like, and can be prepared in various ways depending on the desired purpose. The promoter may be constitutive or inducible. Further, the expression vector may include one or more selective markers for selecting a host cell containing the expression vector, and in the case of a replicable expression vector, may include a nucleotide sequence of replication origin.

The recombinant expression vector according to the present invention constructed as above may be, for example, pHM$_1$E, where the polynucleotide encoding HM$_1$E in which a JO-56 MTD is fused to the N-terminus of a full-length endostatin is inserted into the NdeI restriction site within the multiple cloning sites (MCS) of a pET-28a(+) vector (Novagen, Germany).

In one embodiment of the present invention, the polynucleotide of the present invention is cloned into a pET-28a(+) vector (Novagen, Germany) having a His-Tag sequence so as to fuse 6 histidine tags (SEQ ID NO: 53) to the N-terminus of the cell permeable endostatin recombinant protein to allow easy purification.

The cell permeable endostatin recombinant protein expressed in the above recombinant expression vector has a structure where one of a JO-56 MTD, a JO-73 MTD, a JO-66 MTD, a JO-71 MTD, a JO-85 MTD, a JO-18 MTD, a JO-41 MTD, a JO-135 MTD, and a JO-159 MTD is fused to one terminus or both termini of a full-length endostatin, and a His-Tag is linked to the N-terminus thereof.

The present invention further provides a transformant that is obtained by transforming a host cell with the above recombinant expression vector. Host cells suitable for the present invention may be specifically E. coli. E. coli may be transformed with the recombinant expression vector of the present invention, for example, pHM$_1$E, where a polynucleotide encoding HM$_1$E in which a JO-56 MTD is fused to the N-terminus of a full length endostatin, is inserted and the transformant thus obtained can be used to produce the cell permeable endostatin recombinant protein in large amounts. Any method of introducing a nucleic acid into a host cell may be used for the transformation and may include any transformation techniques well known in the art. Specifically, the methods may include, but is not limited to, microprojectile bombardment, electroporation, calcium phosphate (CaPO$_4$) precipitation, calcium chloride (CaCl$_2$) precipitation, PEG-mediated fusion, microinjection, and liposome-mediated method.

In some embodiments of the present invention, E. coli DH5α was transformed with the recombinant protein expression vectors prepared by the methods described above, which respectively contain HM$_1$E where a JO-56 MTD is fused to, HM$_2$E where a JO-73 MTD is fused to, HM$_3$E where a JO-66 MTD is fused to, and HM$_8$E where a JO-135 MTD is fused to the N terminus of a full-length endostatin to obtain transformant bacteria DH5α/pET-28a(+):HM$_1$E, DH5α/pET-28a(+):HM$_2$E, DH5α/pET-28a(+):HM$_3$E, and DH5α/pET-28a(+):HM$_8$E, respectively. These transformants were deposited with the Korean Collection for Type Cultures (KCTC), Korea Research Institute of Bioscience and Biotechnology (KRIBB) on Mar. 20, 2009 as Deposit Nos. KCTC11485BP, KCTC 11486BP, KCTC11487BP, and KCTC11488BP, respectively.

The present invention also provides a method of producing a cell permeable endostatin recombinant protein involving culturing the transformant under suitable conditions to express the cell permeable endostatin recombinant protein and harvesting the cell permeable endostatin recombinant protein from the culture.

The above production method is carried out by culturing the transformant in a suitable medium under suitable conditions so that a polynucleotide encoding the cell permeable endostatin recombinant protein of the present invention can be expressed. The above method is well known in the art and for example, may be carried out by inoculating a transformant in a suitable medium for growing the transformant, performing a subculture, transferring the same to a main culture medium, culturing under suitable conditions, for example, in the presence of isopropyl-β-D-thiogalactoside (IPTG), a gene expression inducer, and thereby inducing the expression of the recombinant protein. After the culture is completed, it is possible to recover a substantially pure recombinant protein from the above culture solution. The term "substantially pure" means that the recombinant protein of the present invention and the polynucleotide encoding the same are essentially free of other proteins derived from the same host cell.

The recombinant protein obtained above may be recovered by various isolation and purification methods known in the art. Conventionally, cell lysates are centrifuged to remove cell debris and impurities, and then subject to precipitation, e.g. salting out (ammonium sulfate precipitation and sodium phosphate precipitation), solvent precipitation (protein fragment precipitation using acetone, ethanol, etc.). Further, dialysis, electrophoresis and various column chromatographies may be performed. With respect to the chromatography, ion exchange chromatography, gel permeation chromatography, HPLC, reverse phase HPLC, affinity chromatography, and ultrafiltration may be used alone or in combination (Maniatis et al., *Molecular Cloning*: A Laboratory Manual, Cold Spring Harbor Laboratory, Cold Spring Harbor, N.Y., 1982; Sambrook et al., *Molecular Cloning*: A Laboratory Manual, 2d Ed., Cold Spring Harbor Laboratory Press, 1989; Deutscher, M., *Guide to Protein Purification Methods Enzymology* vol. 182. Academic Press. Inc., San Diego, Calif., 1990).

Meanwhile, the recombinant protein expressed in the transformant transformed with the expression vector can be classified into a soluble fraction and an insoluble fraction according to the characteristics of the proteins during protein purification. If the majority of the expressed recombinant proteins are present in the soluble fraction, the recombinant protein can be isolated and purified according to the method as described above. However, when the majority of the expressed recombinant proteins are present in the insoluble fraction, i.e., as inclusion bodies, the recombinant proteins can be isolated and purified by solubilization using polypeptide denaturing agents, e.g., urea or detergents, and then, performing a series of centrifugation, dialysis, electrophoresis and column chromatography. Since there is a risk of losing the recombinant protein's activity due to structural modifications caused by solutions containing polypeptide denaturing agents, the process of purifying the recombinant protein from the insoluble fraction requires desalting and refolding steps. That is, the desalting and refolding steps can be performed by dialysis and dilution with a solution that does not include a polypeptide denaturing agent or by centrifugation with a filter. Further, if the salt concentration of the solution used for the purification of a recombinant protein from a soluble fraction is relatively high, such desalting and refolding steps may be performed.

In one embodiment of the present invention, after confirming that the cell permeable endostatin recombinant proteins of the present invention are mostly present in the insoluble fraction as inclusion bodies, in order to purify the recombinant protein from the insoluble fraction, the insoluble fraction may be dissolved in a lysis buffer containing a non-ionic surfactant such as Triton X-100, subjected to ultrasonification, and then centrifuged to separate the precipitate. The separated precipitate may be dissolved in a buffer containing a denaturing agent, such as urea, and centrifuged to separate the supernatant. The recombinant protein of the present invention obtained by dissolving the insoluble fraction to the maximum extent with urea is purified by means of a histidine-binding protein purification kit and subjected to ultrafiltration, for example, by using an amicon filter for salt removal and protein refolding, thereby obtaining a purified recombinant protein of the present invention.

Further, the present invention provides a pharmaceutical composition use as an anti-cancer agent with improved cancer angiogenesis inhibiting activity comprising the cell permeable endostatin recombinant protein as an active ingredient.

Administration of the cell permeable endostatin recombinant protein according to the present invention may allow endostatin to be maintained at a high concentration inside and outside of the endothelial cells present in tumor tissues, thereby inducing the binding of endostatin to the specific receptor (integrin $\alpha 5\beta 1$) present on the surface of the endothelial cells and blocking new microvessel formation in tumor tissues. Thus, the cell permeable endostatin recombinant protein according to the present invention may be used as an anti-cancer agent against various cancers.

The pharmaceutical composition comprising the recombinant protein of the present invention as an active ingredient may further include pharmaceutically acceptable carriers suitable for oral administration or parenteral administration. The carriers for oral administration may include lactose, starch, cellulose derivatives, magnesium stearate, stearic acid and the like. In case of oral administration, the recombinant protein of the present invention can be formulated in the form of chewable tablets, buccal tablets, troches, capsules, elixir, suspensions, syrup, wafers or combination thereof by mixing with the carrier. Further, the carriers for parenteral administration may include water, suitable oil, saline, aqueous glucose, glycol and the like, and may further include stabilizers and preservatives. Suitable stabilizers for the present invention may include antioxidants such as sodium bisulfite, sodium sulfite and ascorbic acid. Suitable preservatives may include benzalconium chloride, methyl-paraben, propyl-paraben and chlorobutanol. Other pharmaceutically acceptable carriers may be used by referring to the following literature (*Remington's Pharmaceutical Sciences*, 19th ed., Mack Publishing Company, Easton, Pa., 1995).

The pharmaceutical composition of the present invention may be formulated into various parenteral or oral administration forms. Representative examples of formulations for parenteral administration include injection formulations, specifically isotonic solutions or suspensions. Injection formulations may be formulated by conventional methods using suitable dispersing agents, wetting agents and suspension agents. For example, each ingredient may be dissolved in a saline solution or a buffer solution to formulate for injection. Formulations for oral administration include, for example, tablets and capsules, which may include diluents (e.g., lactose, dextrose, sucrose, mannitol, sorbitol, cellulose and/or glycin) and lubricants (e.g., silica, talc, stearic acid, magnesium stearate, calcium stearate, and/or polyethylene glycol), in addition to the active ingredient. The tablets may include binders, such as magnesium aluminum silicate, starch paste, gelatin, tragacanth, methyl cellulose, sodium carboxymethylcellulose, and/or polyvinylpyrrolidone, and in some cases, may additionally include disintegrating agents, such as starch, agar, alginic acid or sodium alginate, absorbents, coloring agents, flavoring agents and/or sweeteners. The above formulations can be prepared by conventional mixing, granulating or coating methods.

The pharmaceutical compositions of the present invention may further include additives, such as preservatives, hydration agents, emulsifiers, salts for osmotic regulation, and/or buffering agents and other therapeutically effective materials, and may be formulated according to conventional methods known in the art.

In addition, the pharmaceutical composition of the present invention may be administered to humans or animals orally or parenterally, such as intravenously, subcutaneously, intranasally or intraperitoneally. Oral administration may include sublingual application. Parenteral administration may include drip infusion and injection, such as subcutaneous injection, intramuscular injection, intravenous injection and intratumoral injection.

The total effective amount of the cell permeable endostatin recombinant protein of the present invention may be administered to patients in a single dose or may be administered by a fractionated treatment protocol, in which multiple doses are administered over a prolonged period of time. Although the amount of the active ingredient in the composition of the present invention may vary depending on the severity of the disease, the active ingredient may generally be administered several times a day with an effective unit dose of 5 to 20 mg for an adult human. However, the suitable dose of the recombinant protein in the pharmaceutical composition of the present invention may depend on many factors, such as age, body weight, health condition, sex, disease severity, diet and excretion of patients, as well as the route of administration and the number of treatments to be administered. In view of the above, any person skilled in the art may determine the effective dose of the above recombinant protein as an anti-cancer agent for a specific use. The pharmaceutical composition of the present invention containing the recombinant protein is not particularly limited in terms of its formulation, administration route and/or administration method insofar as it exhibits the effects of the present invention.

EXAMPLES

Hereinafter, the embodiments of the present invention will be described in more detail with reference to the following examples. However, the examples are only provided for purposes of illustration and are not to be construed as limiting the scope of the invention.

Example 1

Preparation of Cell Permeable Endostatin Recombinant Proteins (CP-Endostatin)

<1-1> Preparation of Cell Permeable Endostatin Recombinant Proteins Using Jo-56 and JO-73 MTDs Six full-length forms of cell permeable endostatin recombinant proteins were designed using a JO-56 MTD ($MTD_1$) and a JO-73 MTD ($MTD_2$) as follows (see FIG. 1*a*).

Specifically, the full length forms of the endostatin recombinant proteins fused to a JO-56 MTD ($MTD_1$) are:
1) $HM_1E$, where a JO-56 MTD is fused to the N-terminus of a full length endostatin;
2) $HEM_1$, where a JO-56 MTD is fused to the C-terminus of a full length endostatin; and
3) $HM_1EM_1$, where a JO-56 MTD is fused to both termini of a full length endostatin, where a His-Tag is covalently coupled to the N-terminus of all of the above constructs.

In addition, the full-length forms of the endostatin recombinant proteins fused to a JO-73 MTD ($MTD_2$) are:
1) $HM_2E$, where a JO-73 MTD is fused to the N-terminus of a full length endostatin;
2) $HEM_2$, where a JO-73 MTD is fused to the C-terminus of a full length endostatin; and
3) $HM_2EM_2$, where a JO-73 MTD is fused to both termini of a full length endostatin, where a His-Tag is covalently coupled to the N-terminus of all of the above constructs.

In order to prepare the above recombinant constructs, polymerase chain reactions (PCRs) were carried out using a primer pair specifically designed for each recombinant construct and a human endostatin cDNA as the template. The forward and reverse primers for amplifying $HM_1E$ have nucleotide sequences represented by SEQ ID NOS: 42 and 41, respectively; those for amplifying $HEM_1$ have nucleotide sequences represented by SEQ ID NOS: 40 and 43, respectively; and those for amplifying $HM_1EM_1$ have nucleotide sequences represented by SEQ ID NOS: 42 and 43, respectively.

In addition, the forward and reverse primers for amplifying $HM_2E$ have nucleotide sequences represented by SEQ ID NOS: 44 and 41, respectively; those for amplifying $HEM_1$ have nucleotide sequences represented by SEQ ID NOS: 40 and 45, respectively; and those for amplifying $HM_2EM_2$ have nucleotide sequences represented by SEQ ID NOS: 44 and 45, respectively.

The above PCR was carried out in a final volume of 50 μl reaction mixture containing 100 ng of a plasmid DNA containing human endostatin cDNA as a template, 0.2 mM (final concentration) dNTP mixture, 1 μM of each primer, 5 μl of 10×Taq buffer, and 1 μl of Taq polymerase (Novagen, Germany). The PCR conditions were as follows: denaturation at 94° C. for 5 minutes; 30 cycles of 94° C. for 30 seconds, 63° C. for 30 seconds and 72° C. for 30 seconds; and final amplification at 72° C. for 5 minutes. After the PCR was completed, the amplified products were confirmed by carrying out electrophoresis on a 1.0% agarose gel.

Figure 2A:
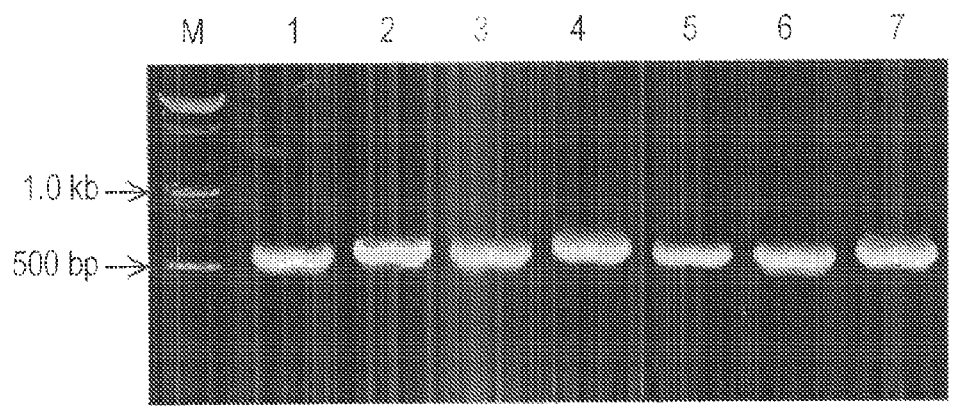
FIG. 2a is the result of PCR amplification of the endostatin recombinant proteins, each being fused to one of JO-56 and JO-73 MTDs and designed in a full-length form according to the present invention.
Figure 2B:
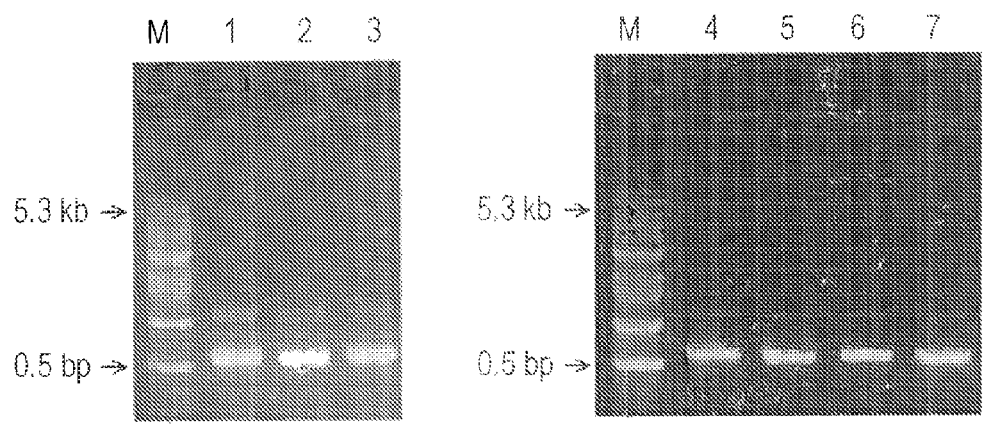
FIG. 2b is the result of PCR amplification of the endostatin recombinant proteins, each being fused to one of JO-66, JO-71, JO-85, JO-18, JO-41, JO-135, and JO-159 MTDs and designed in a full-length form according to the present invention.

As shown in FIG. 2a, it was confirmed that each MTD-fused endostatin recombinant fragment was amplified to the desired size.

Figure 3A:
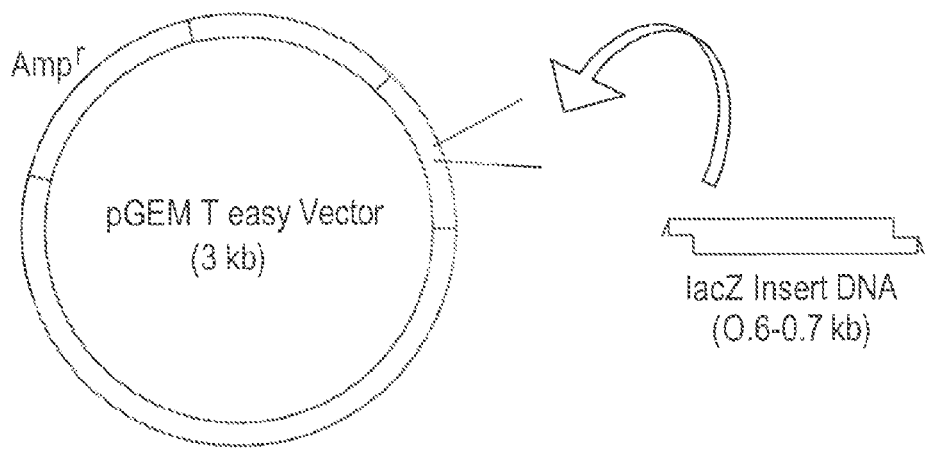
FIG. 3a is a schematic diagram illustrating a process of subcloning the PCR product into the pGEM-T Easy vector.

After recovering the amplified recombinant fragment from the agarose gel, each recombinant fragment was extracted and purified using a commonly used kit (QIAquick Gel extraction kit, Qiagen, USA). The extracted fragment was inserted into a pGEM-T Easy vector (Promega, USA) (FIG. 3a), followed by transformation of E. coli DH5α supercompetent cells with the vector. The cells were cultured on a LB plate media supplemented with 100 μg/ml of ampicillin to select the transformed E. coli. The transformed E. coli were inocuated in a LB medium again to obtain a large amount of pGEM-T Easy vectors in which an endostatin recombinant fragment fused to each MTD is inserted.

Figure 3B:
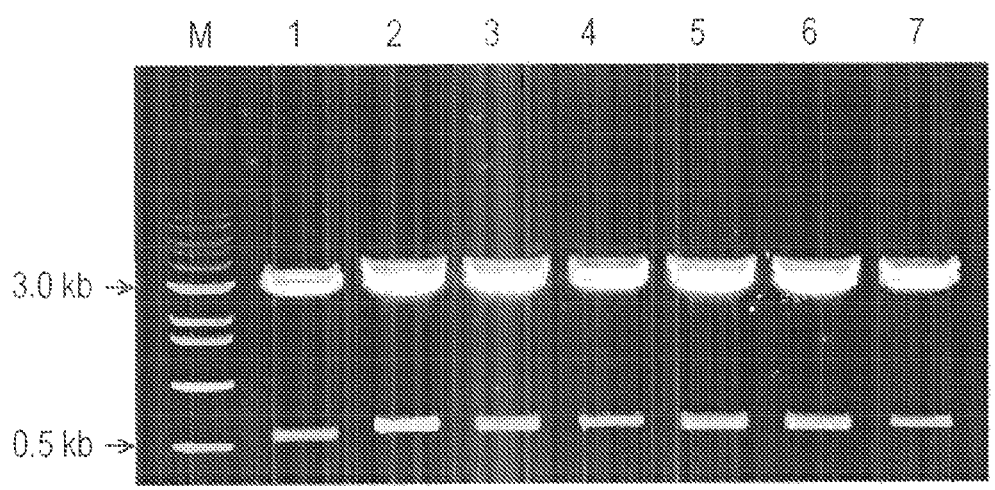
FIGS. 3b and 3c are photographs showing that the PCR product of the MTD-fused endostatin recombinant protein according to the present invention was subcloned into the pGEM-T Easy vector.

FIG. 3b shows the results from an agarose gel electrophoresis of the recombinant fragment which was cleaved from pGEM-T Easy vector by a NdeI restriction enzyme (Enzynomics, Korea), confirming the successful subcloning of each recombinant fragment into the vector.

Figure 4A:
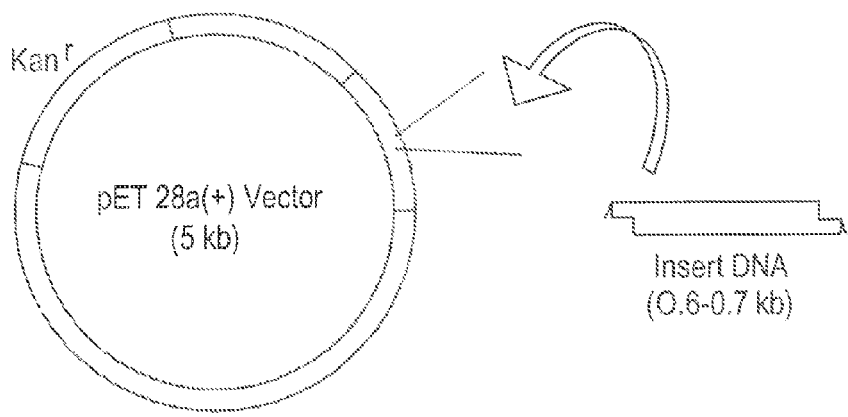
FIG. 4a is a schematic diagram illustrating a process of constructing the expression vectors by cloning the MTD-fused endostatin recombinant fragment into the pET-28a(+) vector according to the present invention.

The pGEM-T Easy vectors in which an endostatin recombinant fragment fused to each MTD is inserted were digested with NdeI at 37° C. for 1 hour to obtain a recombinant fragments for each vector. Meanwhile, an expression vector bearing a His-Tag and a T7 promoter, pET-28a(+) (Novagen, Germany), was digested with NdeI under the same conditions as above. The above recombinant fragments and the digested pET-28a(+) vector were isolated by electrophoresis and purified using a commonly used kit (QIAquick Gel extraction kit, Qiagen, USA). With the addition of a T4 DNA ligase (Takara, Japan) to a mixture comprising these fragments and the vector, the mixture was subjected to ligation at 16° C. for 12 hours, followed by transformation of the E. coli DH5α supercompetent cells to obtain the recombinant protein expression vectors (FIG. 4a).

Figure 4B:
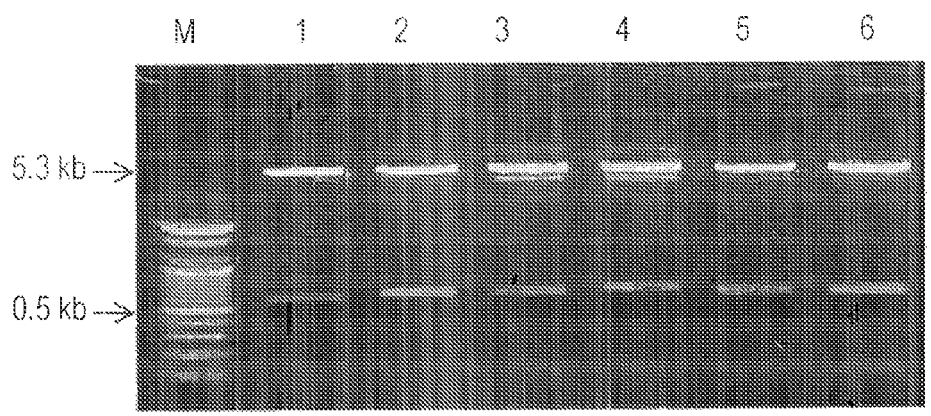
FIGS. 4b and 4c are photographs showing that the MTD-fused endostatin recombinant fragment according to the present invention was cloned into the pET-28a(+) vector.

FIG. 4b shows the results from an agarose gel electrophoresis of the recombinant fragment which was cleaved from pET-28a(+) vector by a NdeI restriction enzyme (Enzynomics, Korea), confirming the successful subcloning of each endostatin recombinant fragment into the vector.

The recombinant protein expression vectors thus obtained were designated $pHM_1E$, $pHEM_1$, $pHM_1EM_1$, $pHM_2E$, $pHEM_2$, and $pHM_2EM_2$, respectively. Among these vectors, the recombinant expression vectors $pHM_1E$ and $pHM_2E$ were used to transform E. coli. DH5α to obtain transformant bacteria DH5α/pET-28a(+):$HM_1E$ and DH5α/pET-28a(+):$HM_2E$, which were deposited with the Korean Collection for Type Cultures (KCTC), Korea Research Institute of Bioscience and Biotechnology (KRIBB) on Mar. 20, 2009 as Deposit Nos. KCTC11485BP and KCTC 11486BP, respectively.

The results from the sequencing analysis confirmed that, as the full-length forms of the above endostatin recombinant proteins, $HM_1E$ has an amino acid sequence represented by SEQ ID NO: 15, which is encoded by a polynucleotide having an amino acid sequence represented by SEQ ID NO: 14; $HEM_1$ has an amino acid sequence represented by SEQ ID NO: 17, which is encoded by a polynucleotide having an amino acid sequence represented by SEQ ID NO: 16; $HM_1EM_1$ has an amino acid sequence represented by SEQ ID NO: 19, which is encoded by a polynucleotide having an amino acid sequence represented by SEQ ID NO: 18; $HM_2E$ has an amino acid sequence represented by SEQ ID NO: 21, which is encoded by a polynucleotide having an amino acid sequence represented by SEQ ID NO: 20; $HEM_2$ has an amino acid sequence represented by SEQ ID NO: 23, which is encoded by a polynucleotide having an amino acid sequence represented by SEQ ID NO: 22; and $HM_2EM_2$ has an amino acid sequence represented by SEQ ID NO: 25, which is encoded by a polynucleotide having an amino acid sequence represented by SEQ ID NO: 24.

As a control to be compared with the above cell permeable endostatin recombinant proteins, recombinant protein HE fused to only a histidine-tag (His-Tag) and lacking a MTD was prepared. The control protein has an amino acid sequence represented by SEQ ID NO: 13, which is encoded by a polynucleotide having a nucleotide sequence represented by SEQ ID NO: 12.

<1-2> Preparation of cell permeable endostatin recombinant proteins using JO-66, JO-71, JO-85, JO-18, JO-41, JO-135, and JO-159 MTDs MTD fused cell permeable recombinant proteins were prepared using JO-66 ($MTD_3$), JO-71 ($MTD_4$), JO-85($MTD_5$), JO-18 ($MTD_6$), JO-41 ($MTD_7$), JO-135 ($MTD_8$), and JO-159 ($MTD_9$) MTDs, as follows:
1) $HM_3E$, where a JO-66 MTD is fused to the N-terminus of a full length endostatin;

2) HM₄E, where a JO-71 MTD is fused to the N-terminus of a full length endostatin;
3) HM₅E, where a JO-85 MTD is fused to the N-terminus of a full length endostatin;
4) HM₆E, where a JO-18 MTD is fused to the N-terminus of a full length endostatin;
5) HM₇E, where a JO-41 MTD is fused to the N-terminus of a full length endostatin;
6) HM₈E, where a JO-135 MTD is fused to the N-terminus of a full length endostatin; and
7) HM₉E, where a JO-159 MTD is fused to the N-terminus of a full length endostatin; where a His-Tag is covalently coupled to the N-terminus of each of the above recombinant constructs.

In order to prepare the above recombinant constructs, PCR was performed by the same method as in EXAMPLE <1-1>. The forward and reverse primers for amplifying HM₃E have nucleotide sequences represented by SEQ ID NOS: 46 and 41, respectively; those for amplifying HM₄E have nucleotide sequences represented by SEQ ID NOS: 47 and 41, respectively; those for amplifying HM₅E have nucleotide sequences represented by SEQ ID NOS: 48 and 41, respectively; those for amplifying HM₆E have nucleotide sequences represented by SEQ ID NOS: 49 and 41, respectively; those for amplifying HM₇E have nucleotide sequences represented by SEQ ID NOS: 50 and 41, respectively; those for amplifying HM₈E have nucleotide sequences represented by SEQ ID NOS: 51 and 41, respectively; and those for amplifying HM₉E have nucleotide sequences represented by SEQ ID NOS: 52 and 41, respectively.

Figure 3C:
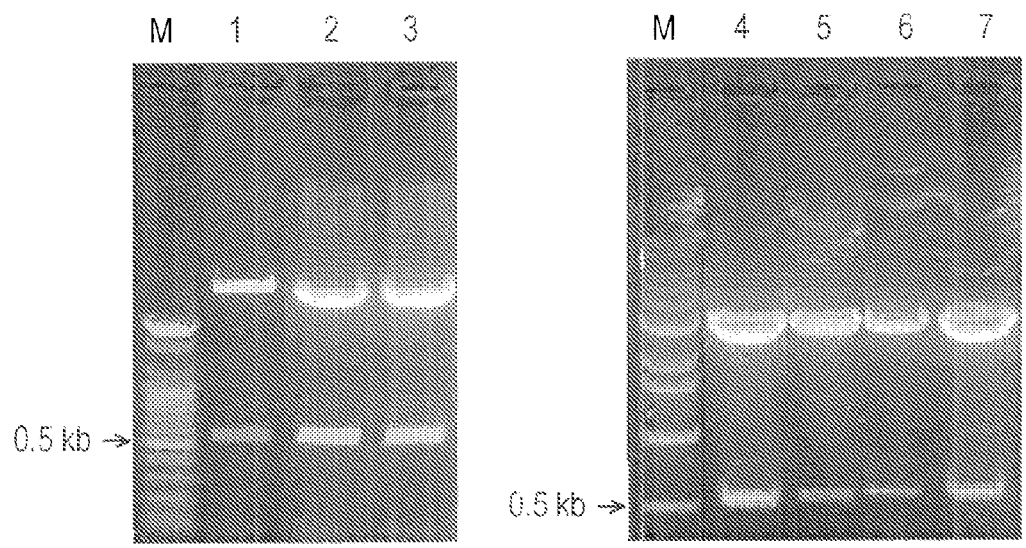
Figure 4C:
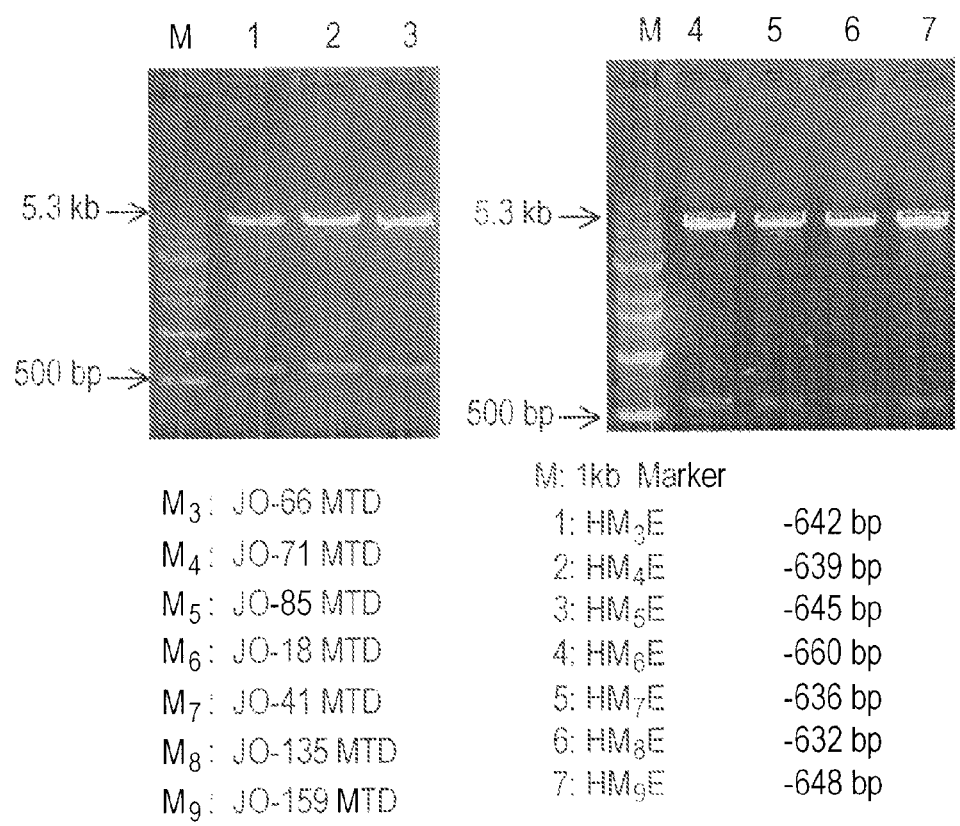

Each of the PCR amplified recombinant fragments was subcloned into a pGEM-T Easy vector by the same method as in EXAMPLE <1-1>, followed by inserting the same into a pET-28a(+) vector to obtain expression vectors of the recombinant proteins according to the present invention. The successful insertion of the recombinant fragments into the pGEM-T Easy and pET-28a(+) vectors was confirmed by FIGS. 3c and 4c.

The recombinant protein expression vectors thus obtained were designated pHM₃E, pHM₄E, pHM₅E, pHM₆E, pHM₇E, pHM₈E, and pHM₉E, respectively. Among these vectors, the recombinant expression vectors pHM₃E and pHM₈E were used to transform *E. coli*. DH5α to obtain transformant bacteria DH5α/pET-28a(+):HM₃E and DH5α/pET-28a(+):HM₈E, where were deposited with the Korean Collection for type Cultures (KCTC), Korea Research Institute of Bioscience and Biotechnology (KRIBB) on Mar. 20, 2009 as Deposit Nos. KCTC11487BP and KCTC 11488BP, respectively.

The results from the sequencing analysis confirmed that, as the full-length form of the above endostatin recombinant protein fused to JO-66 MTD, HM₃E has an amino acid sequence represented by SEQ ID NO: 27, which is encoded by a polynucleotide having an amino acid sequence represented by SEQ ID NO: 26; as the full-length form of the above endostatin recombinant protein fused to JO-71 MTD, HM₄E has an amino acid sequence represented by SEQ ID NO: 29, which is encoded by a polynucleotide having an amino acid sequence represented by SEQ ID NO: 28; as the full-length form of the above endostatin recombinant protein fused to JO-85 MTD, HM₅E has an amino acid sequence represented by SEQ ID NO: 31, which is encoded by a polynucleotide having an amino acid sequence represented by SEQ ID NO: 30; as the full-length form of the above endostatin recombinant protein fused to JO-18 MTD, HM₆E has an amino acid sequence represented by SEQ ID NO: 33, which is encoded by a polynucleotide having an amino acid sequence represented by SEQ ID NO: 32; as the full-length form of the above endostatin recombinant protein fused to JO-41 MTD, HM₇E has an amino acid sequence represented by SEQ ID NO: 35, which is encoded by a polynucleotide having an amino acid sequence represented by SEQ ID NO: 34; as the full-length form of the above endostatin recombinant protein fused to JO-135 MTD, HM₈E has an amino acid sequence represented by SEQ ID NO: 37, which is encoded by a polynucleotide having an amino acid sequence represented by SEQ ID NO: 36; and as the full-length form of the above endostatin recombinant protein fused to JO-159 MTD, HM₉E has an amino acid sequence represented by SEQ ID NO: 39, which is encoded by a polynucleotide having an amino acid sequence represented by SEQ ID NO: 38.

The forward and reverse primer pairs used for the amplification of recombinant proteins used in EXAMPLES <1-1> and <1-2> are summarized in Table 2 below.

TABLE 2

| Primer | SEQ ID NO | Sequence |
|---|---|---|
| HE-5' (36 nts) | 40 | CCG CAT ATG CAC AGC CAC CGC GAC TTC CAG CCG GTG |
| HE-3' (36 nts) | 41 | CCG CAT ATG CTA CTT GGA GGC AGT CAT GAA GCT GTT |
| HM₁E-5' (63 nts) | 42 | CCG CAT ATG GTG CTG CTG GCG GCG GCG CTG ATT GCG CAC AGC CAC CGC GAC TTC CAG CCG GTG |
| HEM₁-3' (63 nts) | 43 | CCG CAT ATG CTA CGC AAT CAG CGC CGC CGC CAG CAG CAC CTT GGA GGC AGT CAT GAA GCT GTT |
| HM₂E-5' (60 nts) | 44 | CCG CAT ATG CCG GTG CTG CTG CTG GCG CCG CAC AGC CAC CGC GAC TTC CAG CCG GTG |
| HEM₂-3' (60 nts) | 45 | CCG CAT ATG CTA CGG CGC CAG CAG CAG CAG CAC CGG CTT GGA GGC AGT CAT GAA GCT GTT |
| HM₃E-5' (66 nts) | 46 | CCG CAT ATG GCG GCG GCG CTG GCG GCG ATT GCG GTG ATT CAC AGC CAC CGC GAC TTC CAG CCG GTG |
| HM₄E-5' (63 nts) | 47 | CCG CAT ATG GCG CTG GCG CTG CTG CTG GTG CCG CAC AGC CAC CGC GAC TTC CAG CCG GTG |
| HM₅E-5' (69 nts) | 48 | CCG CAT ATG CTG CTG GCG GCG GCG GCG GCG CTG CTG CTG GCG CAC AGC CAC CGC GAC TTC CAG CCG GTG |
| HM₆E-5' (84 nts) | 49 | CCG CAT ATG GCG GCG CTG GCG CTG GGC GTG GCG GCG GCG CCG GCG GCG GCG CCG GCG CAC AGC CAC CGC GAC TTC CAG CCG GTG |
| HM₇E-5' (60 nts) | 50 | CCG CAT ATG GCG GCG GCG CTG CTG GCG GTG GCG CAC AGC CAC CGC GAT TTC CAG CCG GTG |
| HM₈E-5' (66 nts) | 51 | CCG CAT ATG GCG GCG GTG GCG CTG CCG GCG GCG GCG CCG CAC AGC CAC CGC GAC TTC CAG CCG GTG |
| HM₉E-5' (72 nts) | 52 | CCG CAT ATG ATT GCG ATT GCG GCG ATT CCG GCG ATT CTG GCG CTG CAC AGC CAC CGC GAC TTC CAG CCG GTG |

Example 2

Expression of Recombinant Proteins

<2-1> Selection of Optimal Bacterial Strains

In order to select the optimal bacterial strain for the expression of cell permeable endostatin recombinant proteins, the following experiments were carried out in *E. coli* BL21 (DE3), BL21 Gold (DE3), BL21 CodonPlus (DE3), and BL21 Gold (DE3) pLysS strains (Stratagene, USA), all of which contain the LacI promoter.

First, the above *E. coli* BL21 (DE3), BL21 Gold (DE3), BL21 CodonPlus (DE3), and BL21 Gold (DE3) pLysS strains were transformed with the recombinant expression vectors prepared in EXAMPLE <1-1> above, i.e., pHM$_1$E, pHEM$_1$, pHM$_1$EM$_1$, pHM$_2$E, pHEM$_2$, and pHE (control), respectively, by a heat shock method, followed by incubation in a LB medium containing 50 μg/ml of kanamycin. Thereafter, *E. coli* transformed with DNA encoding the recombinant protein was inoculated in 1 ml of a LB medium and cultured at 37° C. overnight, and then inoculated again in 100 ml of a LB medium and cultured at 37° C. until the optical density OD$_{600}$ reached 0.6. To the culture was added 0.7 mM isopropyl-β-D-thiogalactoside (IPTG) as a protein expression inducer, followed by culturing at 37° C. for an additional 3 hours. 1 ml of the *E. coli* culture was subjected to centrifugation at room temperature at a speed of 13,000 rpm for 1 minute to remove the supernatant and harvest bacterial cells. The harvested bacterial cells were suspended in a 2× sample loading buffer (125 mM Tris-HCl, 20% glycerol, 2% β-mercaptoethanol, 0.04% bromophenol blue, 4% SDS, pH 6.8), and the suspension was boiled at 100° C. for 5 minutes to disrupt the cells. The cell lysates were centrifuged at a speed of 13,000 rpm for 1 minute to separate the insoluble fraction from the soluble fraction. The soluble and insoluble fractions thus obtained were loaded on a SDS-PAGE gel to analyze the protein expression profile and the degree of expression.

When the expression of the recombinant protein according to the present invention in various host strains was examined, BL21 CodonPlus (DE3) showed the highest level of expression as shown in FIG. 5a. Thus, this strain was selected as the optimal strain for recombinant protein expression.

<2-2> Induction of Recombinant Protein Expression

The *E. coli* BL21 CodonPlus (DE3), which was selected as the optimal host cell strain in EXAMPLE <2-1> above, was transformed with each of the recombinant expression vectors prepared in EXAMPLE <1-1> above, i.e., pHM$_3$E, pHM$_4$E, pHM$_5$E, pHM$_6$E, pHM$_7$E, pHM$_8$E and pHM$_9$E, respectively, by a heat shock method, followed by incubation in a LB medium containing 50 μg/ml of kanamycin. Thereafter, *E. coli* transformed with DNA encoding the recombinant protein was inoculated in 1 ml of a LB medium and cultured at 37° C. overnight, and then inoculated again in 100 ml of a LB medium and cultured at 37° C. until the optical density OD$_{600}$ reached 0.6. To the culture was added 0.7 mM IPTG as a protein expression inducer (+), or not (−), followed by culturing at 37° C. for an additional 3 hours. 1 ml of the *E. coli* culture was subjected to centrifugation at room temperature at a speed of 13,000 rpm for 1 minute to remove the supernatant and harvest bacterial cells. The harvested bacterial cells were suspended in a 2× sample loading buffer (125 mM Tris-HCl, 20% glycerol, 2% β-mercaptoethanol, 0.04% bromophenol blue, 4% SDS, pH 6.8) and the suspension was boiled at 100° C. for 5 minutes to disrupt the cells. The cell lysates were centrifuged at a speed of 13,000 rpm for 1 minute to separate the insoluble fraction and the soluble fraction. The soluble and insoluble fractions thus obtained were loaded on a SDS-PAGE gel to analyze the protein expression profile and the degree of expression.

Figure 5B:
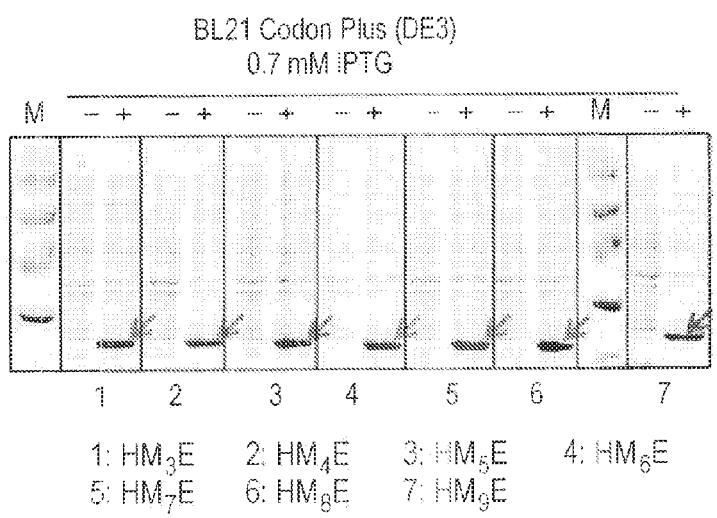
FIG. 5b shows the results from examining the expression of the cell permeable endostatin recombinant proteins according to the present invention in the presence (+) and absence (−) of IPTG, a protein expression inducer.

As shown in FIG. 5b, the cell permeable endostatin recombinant proteins according to the present invention (about 21 kDa) were mostly present in the insoluble fraction as inclusion bodies. The protein expression was significantly increased in the culture solution with IPTG (+) compared to that without IPTG (−).

Example 3

Purification of Recombinant Proteins

Since the cell permeable endostatin recombinant proteins according to the present invention are present in the insoluble fraction as inclusion bodies, 8M urea was used as a strong denaturing agent to separate these proteins from the insoluble fraction.

First, the BL21 CodonPlus (DE3) strains transformed with each of the expression vectors of the present invention (pHE (control), pHM$_1$E, pHEM$_1$, pHM$_1$EM$_1$, and pHM$_2$E) were cultured in 1 L of an LB medium as described in Example 2 above. Each culture solution was centrifuged to harvest the bacterial cells. The obtained bacterial cells were gently suspended in 20 ml of a lysis buffer (100 mM NaH$_2$PO$_4$, 10 mM Tris-HCl, 8 M urea, pH 8.0) carefully so as to avoid forming bubbles, and homogenized at a low temperature using an ultrasonic homogenizer equipped with a microtip. Here, the power was set at 28% of the maximum power, while a 30 second sonication followed by a 10 second pause was repeated for 15 minutes. The sufficiently lysed inclusion bodies were centrifuged at 4° C. at a speed of 8,000 rpm for 10 minutes to remove the cell precipitate and recover the supernatant. The recovered supernatant was loaded onto a Ni-NTA agarose resin where nitrilotriacetic acid agarose was charged with nickel (Ni). The Ni-NTA agarose was used after equilibration by washing with a lysis buffer prior to use. The supernatant was allowed to absorb onto the resin while slowly stirring using a rotary shaker for at least 1 hour at 4° C. The resin absorbed with the inclusion bodies containing the recombinant protein was centrifuged at 4° C. at a speed of 1,000 rpm for 5 minutes to remove the reaction solution and then washed with a washing buffer (100 mM NaH$_2$PO$_4$, 10 mM Tris-HCl, 8 M urea, pH 6.3) five times to remove the non-specific absorbed materials. Onto the washed resin was loaded an elution buffer (100 mM HaH$_2$PO$_4$, 10 mM Tris-HCl, 8 M urea, 500 mM imidazole, pH 4.5) in a volume that is twice the resin volume under acidic conditions of pH 4.0, followed by stirring in a shaker for 1 hour to elute the protein. In order to analyze the purity of the eluted protein, electrophoresis was carried out on a 12% SDS-PAGE gel, and subsequently, the gel was stained with Coomassie Brilliant Blue R250 while gently stirring, and de-stained with a de-staining solution until the band of the target protein can be seen clearly.

Figure 6:
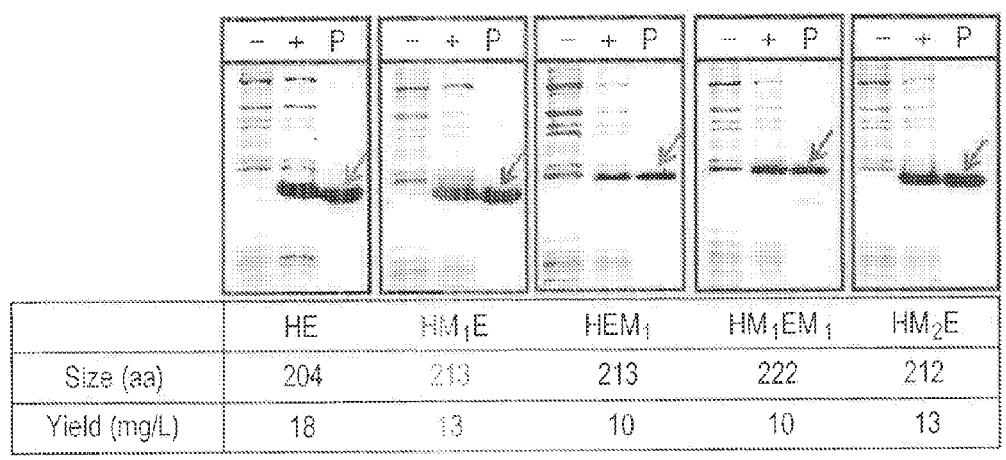
FIG. 6 shows the results from the purification of cell permeable endostatin recombinant proteins expressed from the transformant transformed with the expression vector of the present invention.

As shown in FIG. 6, all of the cell permeable endostatin recombinant proteins fused to a JO-56 MTD and a JO-73 MTD were detected as a single band corresponding to about 21 kDa, as compared with the band of the marker protein. It was confirmed from the above results that the cell permeable endostatin recombinant proteins of the present invention have been purified from the insoluble fraction.

Example 4

Recovery of Protein Activity and Fluorescent Staining

Since the recombinant proteins of the present invention purified from the insoluble fraction in Example 3 above were denatured with 8 M urea, a strong denaturing agent, a refolding process had to be carried out to convert them to an active form, as follows.

First, the purified recombinant proteins were subject to dialysis using a refolding buffer (0.55 M Guanidine HCl, 0.44 M L-arginine, 50 mM Tris-HCl, 150 mM NaCl, 1 mM EDTA, 100 mM NDSB, 2 mM glutathione oxidized, and 0.2 mM glutathione reduced) at 4° C. for 48 hours to remove the denaturing agent. By doing so, the recombinant proteins were reactivated, that is, refolded. Thereafter, the activated recombinant proteins were dialyzed in a dialysis tubing (Snakeskin pleated, PIERCE, USA) against a solution, where culture media RPMI 1640 (Invitrogen, USA) and HBSS (Hang's Balanced Salt Solution) were mixed together in a ratio of 7:3 and supplemented with 5% glycerol and 0.1% CHAPS (Biosesang, Korea) to prevent the endostatin protein from agglomerating, at 4° C. for 9 hours. The solution in the tubing was changed every 3 hours.

The activated cell permeable endostatin recombinant proteins thus obtained were labeled with FITC (fluorescein-5-isothiocyanate, Molecular Probe) in order to confirm the cell permeability more clearly. 1 µl of FITC having a concentration of 333 mg/ml was used for 2 to 20 ml of the recombinant proteins. The FITC conjugation was carried out in a dark room at room temperature for 1 hour by stirring. The unreacted FITC was removed by dialysis in a DMEM medium at 4° C. for 1 day. The FITC-labeled recombinant proteins thus obtained were subject to a Bradford protein assay for protein quantification. As a result, each of the recombinant proteins was measured to have a concentration of about 1 µg/µl.

Example 5

Cell Permeability Analysis

<5-1> Flow Cytometry

In order to examine the cell permeability of the cell permeable endostatin recombinant protein according to the present invention, RAW 264.7 cells (Korean Cell Line Bank, Korea) derived from mouse macrophages were treated with 10 µM of each protein and cultured at 37° C. for 1 hour. The RAW 264.7 cells were cultured in DMEM containing 10% fetal bovine serum (FBS) and 5% penicillin/streptomycin (500 mg/ml). After the completion of the culture, the cells were treated with trypsin/EDTA (T/E) for removal of the free FITC exposed on the cell membranes and washed with cold PBS three times. The cells were analyzed for flow cytometry using the CellQuest Pro software of FACS Calibur (Beckton-Dickinson, USA).

As a result, as shown in FIGS. 7a and 7b, the cell permeable endostatin recombinant proteins ($HM_1E$ and $HEM_1$) in which a JO-56 MTD ($MTD_1$) is fused to the N-terminus and C-terminus of endostatin, respectively, showed high cell permeability as compared to the control without MTD. On the other hand, $HM_1EM_1$ in which a JO-56 MTD is fused to both termini showed almost no cell permeability as compared to the control. In the case of $HM_2E$ in which a JO-73 MTD ($MTD_2$) is fused to the N-terminus of endostatin, the cell permeability was found to be higher than that of the control. In FIGS. 7a and 7b, the gray curve represents cell only, the black curve represents FITC only, the blue curve represents the control protein lacking a MTD (HE), the purple curve represents $HM_1E$ in which $MTD_1$ is fused to the N-terminus of endostatin, the green curve represents $HEM_1$ in which the same MTD is fused to the C-terminus of endostatin, the brown curve represents $HM_1EM_1$ in which the same MTD is fused to both termini, and the red curve represents $HM_2E$ in which $MTD_2$ is fused to the N-terminus of endostatin.

<5-2> Confocal Laser Scanning Microscope Analysis I

NIH3T3 cells derived from mouse fibroblasts (Korean Cell Line Bank, Korea) were treated with the cell permeable endostatin recombinant proteins of the present invention, which were primarily confirmed as to their cell permeability by flow cytometry in EXAMPLE <5-1> above, and the control endostatin proteins lacking MTD, each at a concentration of 10 µM. The treated cells were incubated at 37° C. for 1 hour and observed under a confocal laser scanning microscope. The NIH3T3 cells used above were cultured in DMEM containing 10% FBS and 5% penicillin/streptomycin (500 mg/ml). In order to preserve the FITC fluorescence of the recombinant protein, 10 µl of a mounting medium was dropped onto the glass slide and an observation was made after 15 minutes. For easy detection of the intracellular distribution of MTD, the cells were stained with a nuclear fluorescent stain solution comprising propidium iodide (PI) to examine nuclear localization and cell permeability. The original shape, FITC staining, and PI staining of the cells were observed by means of a confocal laser scanning microscope using a Normaski filter.

Figure 8:
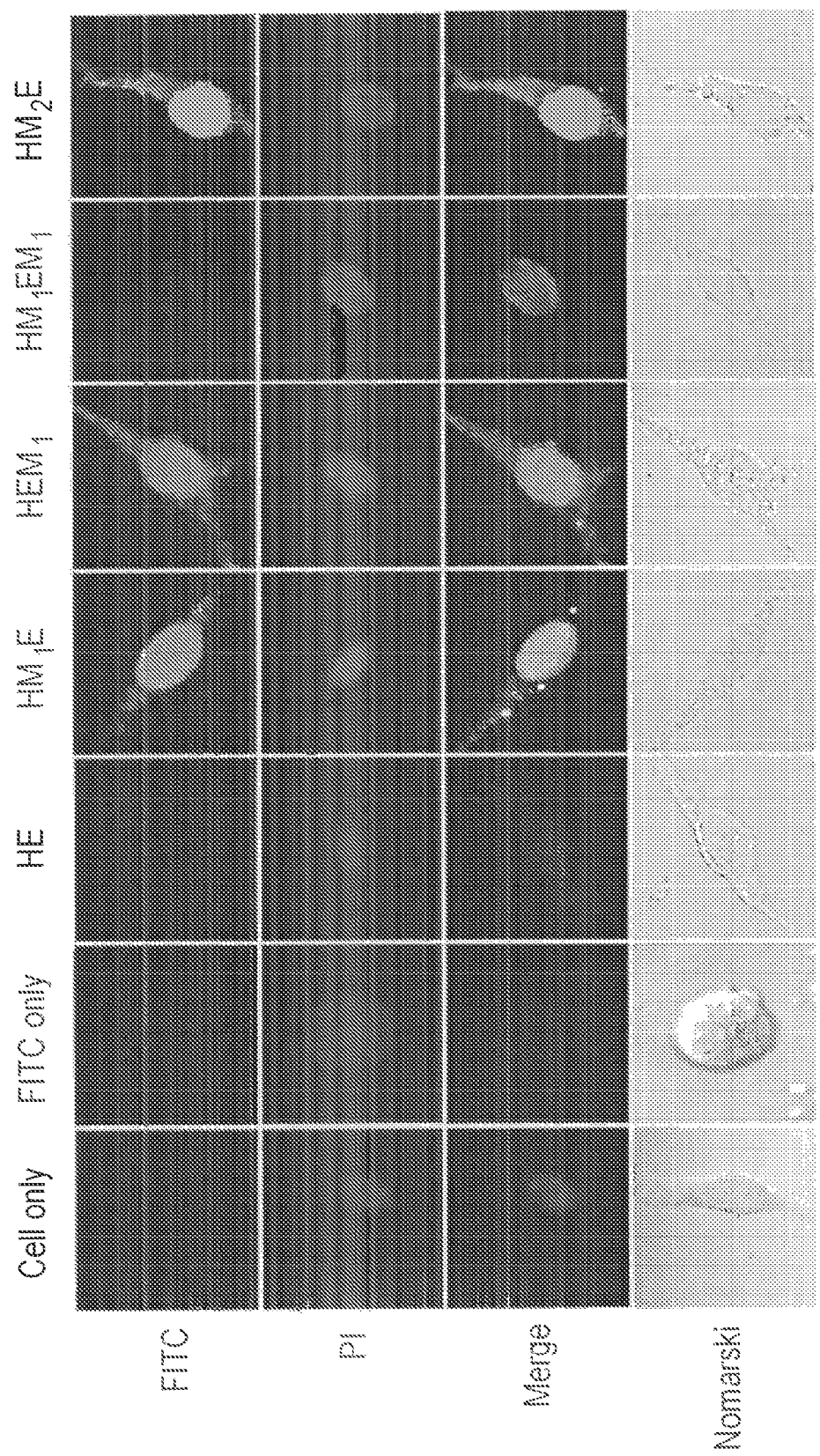
FIG. 8 is a confocal laser scanning microscopy photograph visualizing the cell permeability of the cell permeable endostatin recombinant proteins according to the present invention in mouse fibroblasts.

As shown in FIG. 8, the proteins stained with FITC (green) and PI (red) were clearly localized in the nucleus of the cells, which is consistent with the results from the cell permeability analysis by flow cytometry. Thus, the cell permeability of the cell permeable endostatin recombinant proteins according to the present invention was further confirmed by directly observing the intracellular localization of the proteins.

<5-3> Confocal Laser Scanning Microscope Analysis II

In order to examine whether the cell permeable endostatin recombinant proteins according to the present invention, whose cell permeability was confirmed in EXAMPLE <5-2> above using cultured cells, also exhibit cell permeability in a tissue, the following experiment was carried out.

7-week old Balb/c nu/nu mice (Central Lab. Animal Inc., Seoul), which were immune-deficient by mutation of the major histrocompatibility complex (MHC), were used as test animals. HCT-116 cells, a human colon cancer cell line, were administered to the right legs of the above mice via subcutaneous injection at a concentration of $1 \times 10^7$ cells/ml by using a syringe (omnican, Germany, B. BRAUN) to induce tumors. Meanwhile, $HM_1E$ where a JO-56 MTD ($MTD_1$) is fused to the N-terminus of endostatin, $HEM_1$ where the same is fused to the C-terminus, and $HM_1EM_1$ where the same is fused to both termini, $HM_2E$ where a JO-73 MTD ($MTD_2$) is fused to the N-terminus of endostatin, and MTD lacking HE (control) were labeled with FITC. 300 µg of the FITC-labeled endostatin recombinant proteins were administered to the tumor-bearing mice via intraperitoneal injection. Two hours later, the mice were sacrificed, and various tissue samples were extracted from the liver, kidney, spleen, lung, heart, brain and the tumor tissue. The collected tissue samples were embedded with an OCT compound, frozen, and then sliced using a microtome so that they had a thickness of 14 µm. The tissue specimens were mounted on a glass slide and observed under a confocal laser scanning microscope. In order to preserve the FITC fluorescence of each recombinant protein, 10 µl of a mounting medium was dropped onto the glass slide and an observation was made after 15 minutes.

Figure 9:
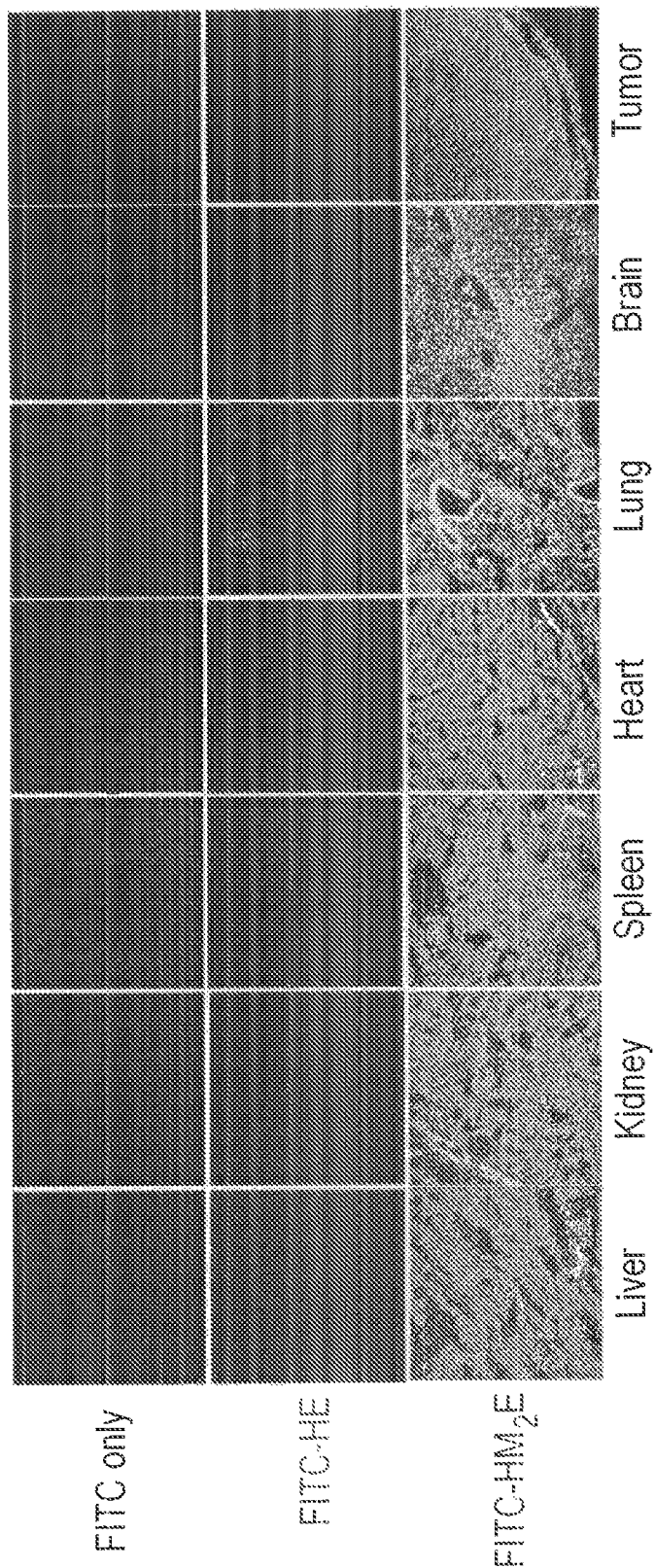
FIG. 9 is a confocal laser scanning microscopy photograph visualizing the cell permeability of the cell permeable endostatin recombinant proteins according to the present invention in various mouse tissues.

As illustrated in FIG. 9, the localization of proteins stained with FITC (green) in the nucleus was clearly observed in all of the tissue specimens, which is consistent with the results obtained by flow cytometry. It can be appreciated from the above results that the cell permeable recombinant proteins of the present invention can effectively transport a target endostatin protein into a tissue due to their superior cell permeability.

Example 6

Cellular Function of Cell Permeable Endostatin Recombinant Proteins

<6-1> Western Blotting

In order to examine the cellular function of the endostatin recombinant proteins whose cell permeability was confirmed, a western blotting analysis was carried out as follows.

First, human umbilical vein endothelial cells (HUVECs) (Bio4You, Korea) were cultured in a M199 medium (L-glutamine 300 mg/l, 2.2 g/L $NaHCO_3$, 25 mM HEPES, 10 unit/ml heparin, 20 ng/ml bFGF, 20% heat inactivated FBS, and 1% streptomycin/penicillin) in a 5% $CO_2$ incubator at 37° C. using a culture dish coated with 2% gelatin.

After 2 ml of M199 medium was added to each well of a 6-well plate, the above cultured HUVECs were inoculated. The plate was incubated at 37° C. for 1 day, followed by culturing in a serum-free medium for an additional 1 day so as to synchronize the cells to the same cell cycle phase. After removing the medium, the HUVECs were washed with PBS (phosphate-buffered saline). Subsequently, the cells were treated with each of the cell permeable endostatin recombinant proteins according to the present invention ($HM_1E$, $HEM_1$, $HM_1EM_1$, and $HM_2E$) and the control protein (HE) at concentrations of 10 µM and 15 µM, respectively, for 4 hours. After removing the protein, the HUVECs were washed with PBS and then cultured in a 5% $CO_2$ incubator at 37° C. for 8 hours. The cultured HUVECs were lysed in 100 µl of a lysis buffer (20 mM HEPES, pH 7.2, 1% Triton-X100, 10% glycerol) on ice for 30 minutes to obtain cell lysates. The cell lysate was centrifuged at 4° C. at a speed of 12,000 rpm for 20 minutes to separate the supernatant. The obtained supernatant was subjected to a Bradford protein assay to quantitatively measure the protein concentration. The prepared cell lysate sample was stored at −80° C. until use.

For the western blot analysis, anti-β-catenin antibody (92 kDa, Santa Cruz Biotechnology, Heidelberg, Germany), anti-c-Myc antibody (67 kDa, Santa Cruz Biotechnology, Heidelberg, Germany), anti-cyclin D1 antibody (37 kDa, Santa Cruz Biotechnology, Heidelberg, Germany), anti-STAT3 antibody (79 kDa, Santa Cruz Biotechnology, Heidelberg, Germany), anti-VEGF (45 kDa, Santa Cruz Biotechnology, Heidelberg, Germany), anti-phospho-ERK1/2 (Thr 185/202, 44.42 kDa, Abeam Cambridge, USA), and anti-phospho-MEK1/2 (Ser 217/221, 45 kDa, Cell Signaling, Boston, USA) were used as primary antibodies, while goat anti-mouse IgG-HRP (Santa Cruz Biotechnology, Germany) and goat anti-rabbit IgG-HRP (Santa Cruz Biotechnology, Germany) were used as secondary antibodies. The above quantitatively measured cell lysate sample was subjected to electrophoresis on a SDS-PAGE gel at 100 V and then transferred onto a polyvinylidene fluoride (PDVF) membrane at 100 V for 1 hour. In order to prevent the nonspecific absorption to antibodies, the PVDF membrane was blocked with 5% (w/v) powdered milk in a TBS/T buffer (10 mM Tris-Cl, pH 8.0, 150 mM NaCl, 0.05% Tween 20) for 1 hour, followed by a reaction at 4° C. for 1 hour adding each of the primary antibodies for 1 day. After the reaction, the PVDF membrane was washed with a TBS/T buffer three times, followed by a reaction adding each of the secondary antibodies at room temperature for 1 day. After washing with a TBS/T buffer three times, the membrane was stained using an enhanced chemiluminescence (ECL) detection system (GE Healthcare Amersham, UK) to detect and analyze the antigen.

As shown in FIG. 10, the HUVECs treated with the cell permeable endostatin recombinant proteins ($HM_1E$, $HEM_1$, $HM_1EM_1$, and $HM_2E$) showed increased expression of the cell proliferation inhibitors, β-catenin, c-Myc, and STAT3, and the angiogenesis stimulator, VEGF, while showing reduced expression of p-ERK and p-MEK, which induce cell migration, as compared with those treated with the conventional recombinant endostatin (HE).

<6-2> Inhibitory Effect on Human Endothelial Cell Migration

In order to examine the cellular function of endostatin recombinant proteins whose cell permeability was confirmed, the inhibitory effect of the recombinant proteins on human endothelial cell migration was examined by a wound healing assay as follows.

HUVECs were cultured in a M199 medium (L-glutamine 300 mg/l, 2.2 g/L $NaHCO_3$, 25 mM HEPES, 10 unit/ml heparin, 20 ng/ml bFGF, 20% heat inactivated FBS, and 1% streptomycin/penicillin) in a 5% $CO_2$ incubator at 37° C. using a culture dish coated with 2% gelatin. After 2 ml of the M199 medium was added to each well of a 6-well plate, the above cultured HUVECs were inoculated and the plate was incubated at 37° C. for 1 day. To each well was added the cell permeable endostatin recombinant proteins according to the present invention ($HM_2E$) and the control protein (HE) at a concentration of 10 µM, followed by incubation in a serum-free medium for 1 hour. After the incubation, the cells were washed with PBS two times and those around the center of the well were removed by scraping with a 10 µl pipette tip. To the plate was added 1 ml of M199 medium, followed by culturing in an incubator in a 5% $CO_2$ incubator at 37° C. for 24 hours. Thereafter, the migration of the HUVECs was observed under an optical microscope.

As shown in FIG. 11, it was confirmed that the cell permeable endostatin recombinant protein ($HM_2E$)-treated group showed increased inhibition of HUVEC migration, as compared with the non-treated group and the control group without MTD (HE).

<6-3> Inhibitory Effect on Human Endothelial Cell Proliferation

In order to confirm the cellular function of endostatin recombination proteins whose cell permeability was confirmed, the inhibitory effect on human endothelial cell proliferation was examined as follows.

HUVECs were inoculated in a M199 medium (L-glutamine 300 mg/l, 2.2 g/L $NaHCO_3$, 25 mM HEPES, 10 unit/ml heparin, 20 ng/ml bFGF, 20% heat inactivated FBS, and 1% streptomycin/penicillin) and cultured using a culture dish coated with 2% gelatin in a 5% $CO_2$ incubator at 37° C. To each well of 6-well plates was added 2 ml of M199 medium and the above cultured cells were inoculated. The plate was then cultured at 37° C. for 1 day. Each well was treated with the cell permeable endostatin recombinant proteins according to the present invention ($HM_2E$) and the control protein (HE) at a concentration of 10 µM, followed by incubation in a serum-free medium for 1 hour. To the plate was added 1 ml of the M199 medium, followed by culturing in an incubator in a 5% $CO_2$ incubator at 37° C. for 0, 24, and 48 hours, respectively. Thereafter, the proliferation of the HUVECs was observed under an optical microscope.

Figure 12A:
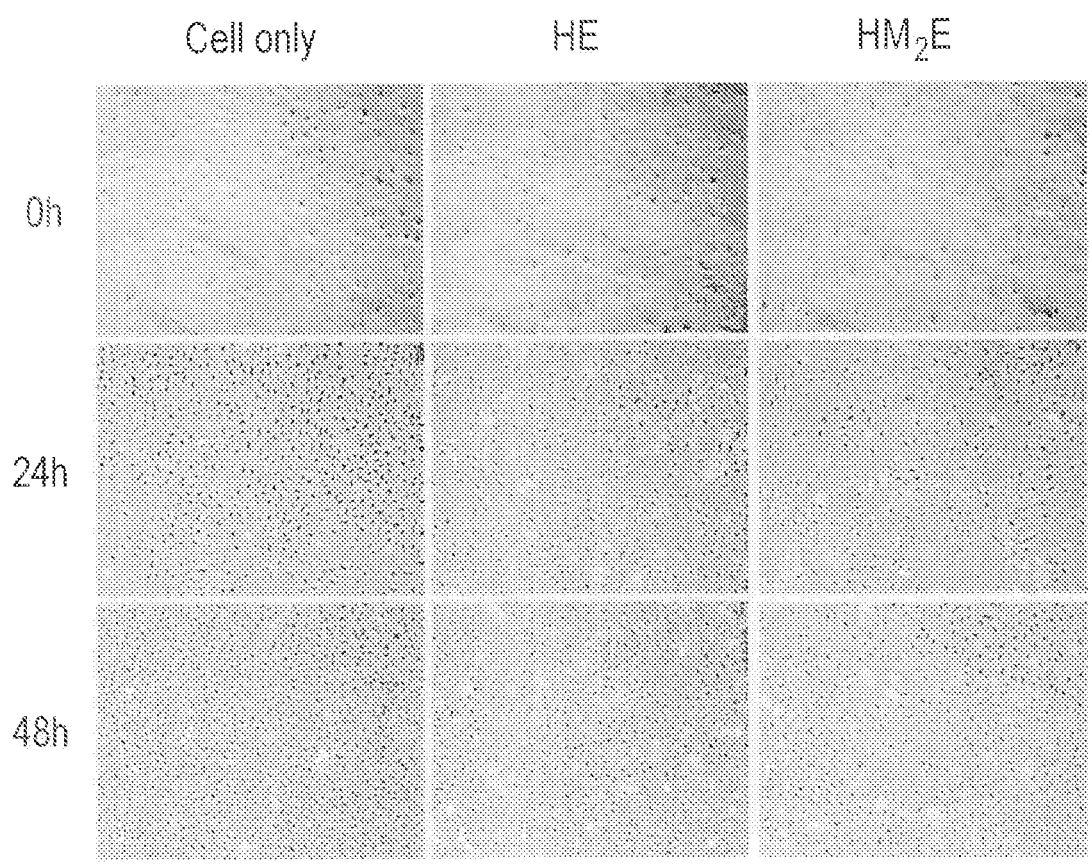

As shown in FIGS. 12a and 12b, it was confirmed that the cell permeable endostatin recombinant protein ($HM_2E$)-treated group showed increased inhibition of HUVEC proliferation, as compared with the non-treated group and the control group without MTD (HE).

<6-4> Inhibitory Effect on Human Endothelial Cell Tube Formation

In order to examine the cellular function of endostatin recombination proteins whose cell permeability was confirmed, the inhibitory effect on the tube formation of human endothelial cells was examined as follows.

HUVECs were inoculated in a M199 medium (L-glutamine 300 mg/L, 2.2 g/L $NaHCO_3$, 25 mM HEPES, 10 unit/ml heparin, 20 ng/ml bFGF, 20% heat inactivated FBS, and 1% streptomycin/penicillin) and cultured using a culture dish coated with 2% gelatin in a 5% $CO_2$ incubator at 37° C. The above cultured cells were suspended in the pre-existing medium (M199) supplemented with 0.1% BSA. 500 μl of the M199 medium was added to each well of the BD Matrigel™ Matrix 12-well plate and the above cell suspension was inoculated. Subsequently, each well was treated with the cell permeable endostatin recombinant proteins according to the present invention ($HM_2E$) and the control protein (HE) at concentrations of 2.5 μM and 5 μM, respectively, followed by culturing in a free-serum medium for 24 hours. The cells cultured on the plate were fixed in a HBSS medium containing 1% paraformaldehyde and then reacted using 10 μM calcein AM fluorescent staining agent for 30 minutes. After culture, the cells were washed with PBS and observed under an optical microscope.

Figure 13A:
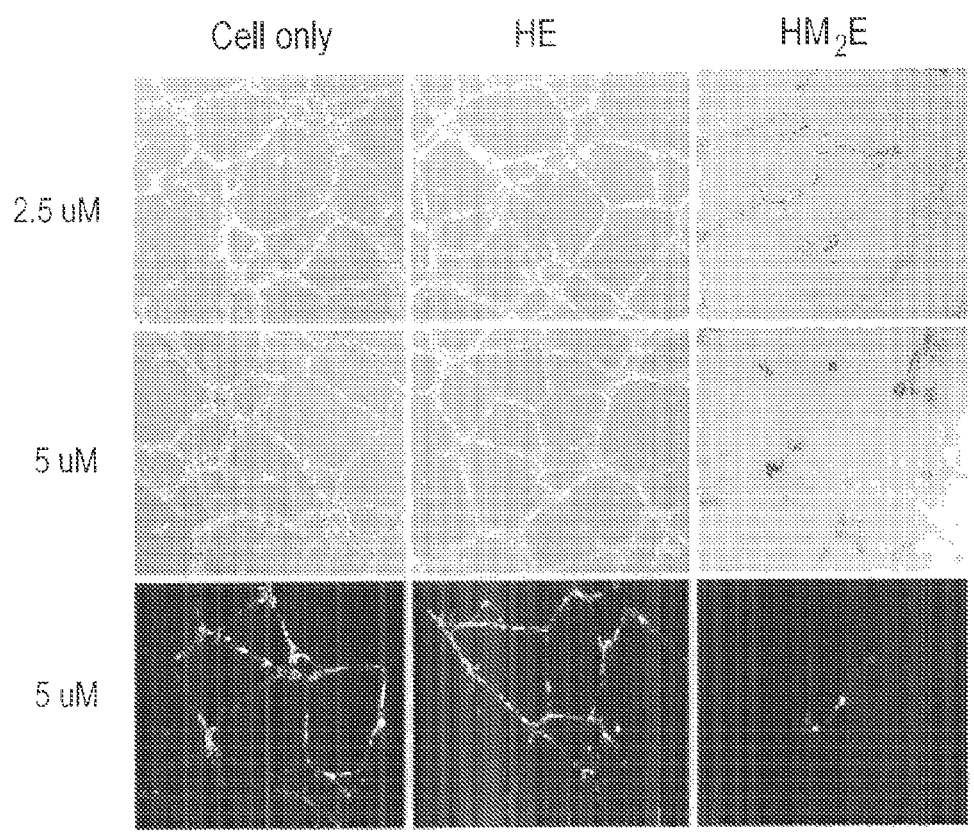
FIGS. 13a and 13b are graphs illustrating the inhibitory effect of the cell permeable endostatin recombination protein according to the present invention on human endothelial cell tube formation.
Figure 13B:
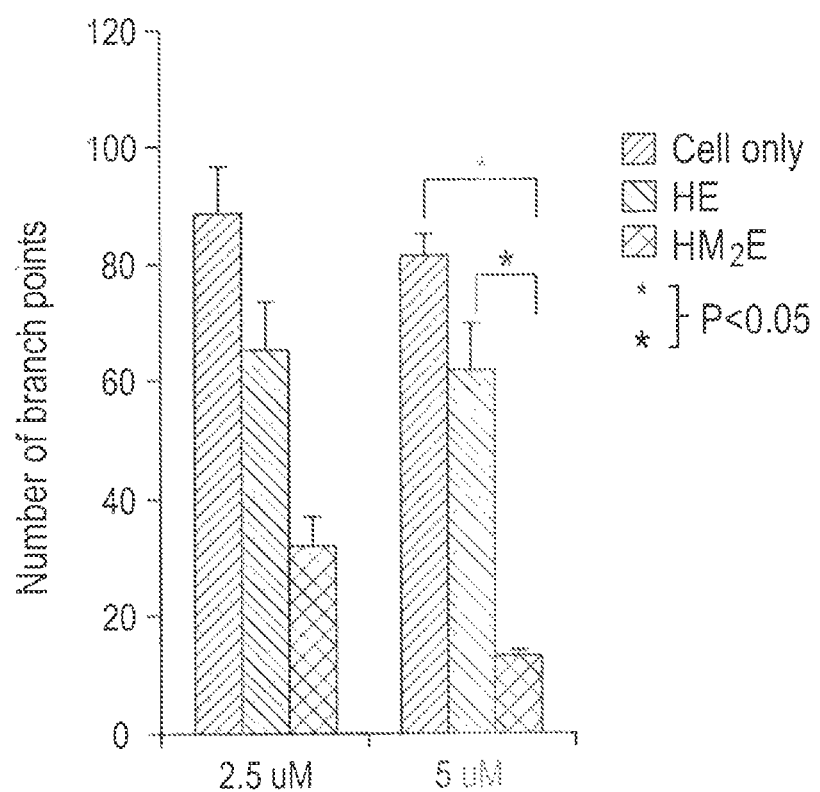

As shown in FIGS. 13a and 13b, it was confirmed that the cell permeable endostatin recombinant protein-treated group ($HM_2E$) showed increased inhibition of the tube formation of human endothelial cells, as compared with the non-treated group and the control group without MTD (HE).

Example 7

In Vivo Function of Cell Permeable Endostatin Recombinant Proteins

In order to examine the cellular function of endostatin recombination proteins whose cell permeability was confirmed, the anti-cancer effect by prevention of angiogenesis was assessed by using an animal model as follows.

In the present experiment, a 5-week old, immune-deficient Balb/c nu/nu mice (Central Lab. Animal Inc., Seoul) were subdivided into 3 groups of 6 mice each. HCT-116 cells (Korean Cell Line Bank, Korea), which are human colon cancer cell lines, were administered to the left upper back of the mouse via subcutaneous injection at a concentration of $1 \times 10^7$ cells/ml by using a syringe (omnican, Germany, B. BRAUN). From the day when the tumor size was measured as 50 to 60 $mm^3$ ($width^2 \times length \times 0.52$), the cell permeable endostatin recombinant proteins $HM_2E$ (Group 3; 200 μg) were administered daily to the mice at a concentration of 0.5 μg/μl using a vernier caliper via intraperitoneal injection for 21 days. As a control, a vehicle (Group 1) and MTD-lacking endostatin protein HE (Group 2) were administered in the same manner as above for 21 days in an amount of 400 μl each. During the 21 day administration, the change in tumor size and body weight in the mouse of each group was monitored, and the results are shown in FIGS. 14a and 14b.

Figure 14A:
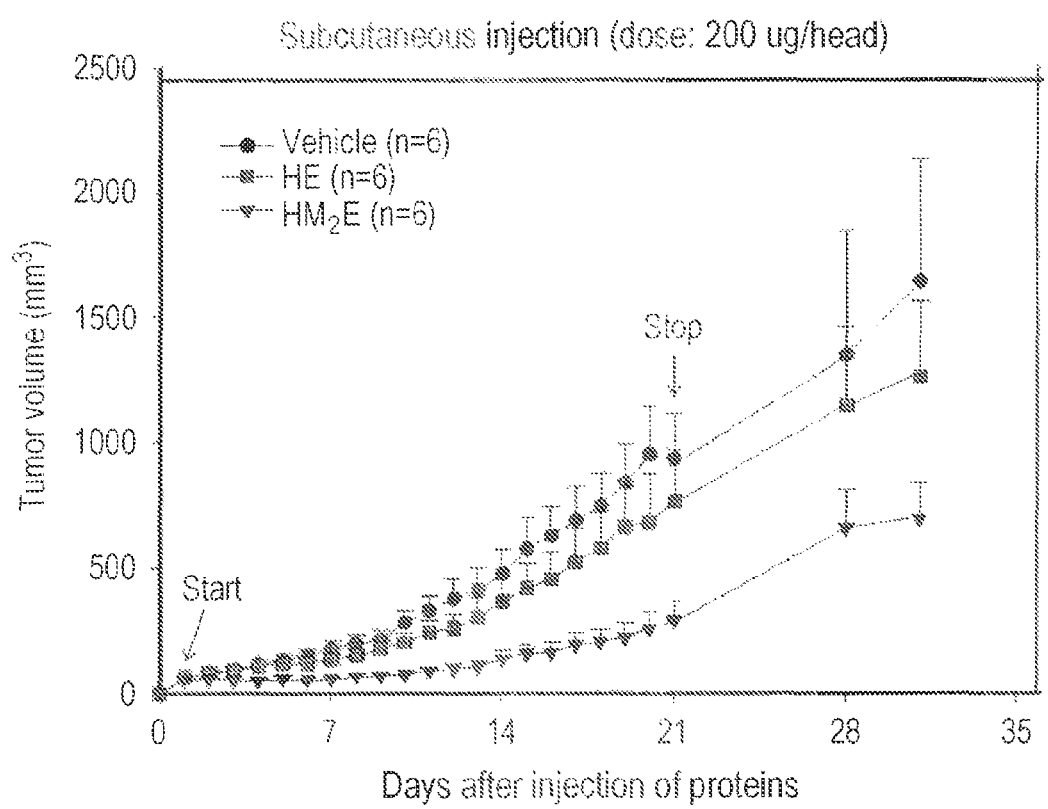
FIGS. 14a and 14b are graphs illustrating the daily change in tumor size and body weight, respectively, in a tumor-bearing mouse where each of the cell permeable endostatin recombinant proteins according to the present invention was administered via subcutaneous injection for 21 days.
Figure 14B:
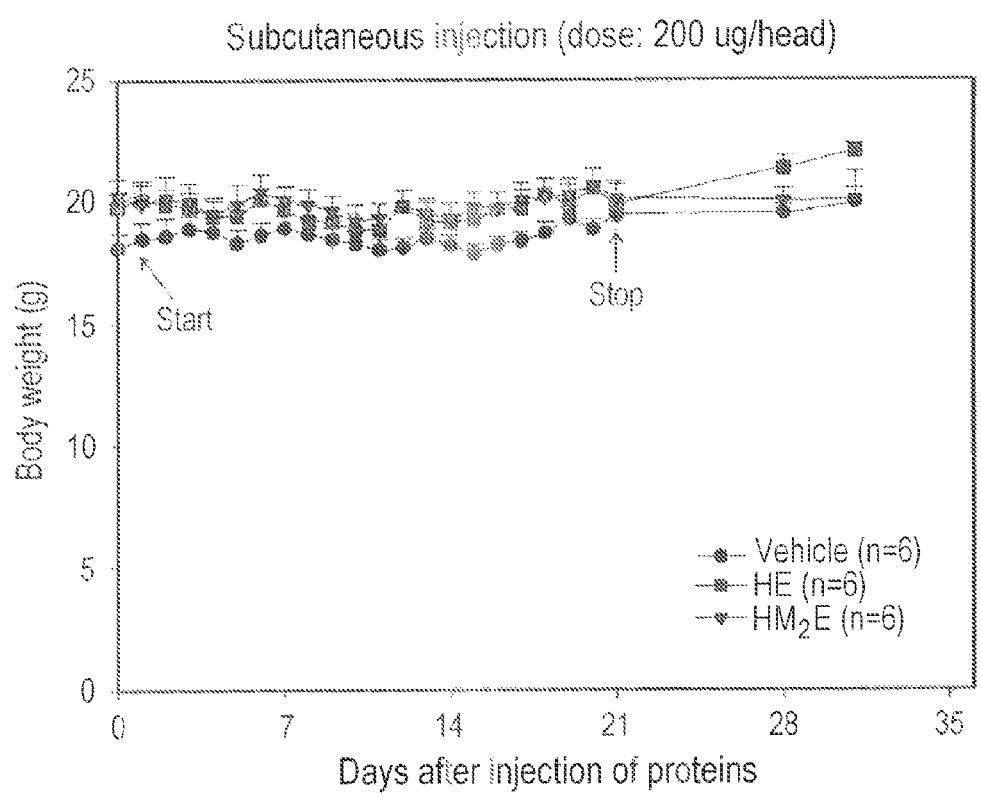

According to the results shown in FIGS. 14a and 14b, tumor growth was significantly reduced in the mice treated with the cell permeable endostatin recombinant proteins $HM_2E$ (Group 3), as compared to that of the controls (Groups 1 and 2), while there was no significant difference in body weight between the control mice and the cell permeable endostatin recombinant protein-treated mice.

Example 8

Immunohistochemical Analysis after Administration of Cell Permeable Endostatin Recombinant Proteins In order to examine the histological changes in tumor tissues following the administration of cell permeable endostatin recombinant proteins, immunohistochemistry staining was carried out using the mouse model in EXAMPLE 7.

Specifically, cell permeable endostatin recombinant proteins ($HM_2E$), as well as vehicle and HE proteins (as control groups), were administered to the mice which were subdivided into three groups (6 mice per group) via subcutaneous injection for 21 days, respectively, according to the same method as described in EXAMPLE 7. After the administration was terminated, tumor tissue samples were extracted from the mice. Each of the extracted tumor tissue samples was fixed in formalin and washed, and then embedded in paraffin melted at 62° C. at the embedding center, to prepare a paraffin block. The prepared paraffin block was sliced with a microtome to have a thickness of 5 μm. The slices were mounted on a glass slide and treated with xylene three times (each for 5 minutes) to remove paraffin. Subsequently, the tissue slide was hydrated with 100%, 100%, 95%, 70%, and 50% ethanol, in order, for 3 minutes each, and washed with running water for 5 minutes. In order to unmask the antigen from the tissue, the glass slide was treated with an antigen retrieval solution, followed by storing at 37° C. for 20 minutes. Subsequently, the tissue slide was washed with PBS for 5 minutes, treated with a peroxide blocking solution for 10 minutes, and again, washed with PBS three times for 5 minutes each, and treated with a power blocking solution for 10 minutes, followed by washing with PBS for 5 minutes. The tissue slide was reacted with a human vascular endothelial cell specific marker 4A11 as the primary antibody at 25° C. for 30 minutes and washed with a PBS buffer for 5 minutes three times and then with goat anti-mouse IgG-HRP (Biogenex) as the secondary antibody for 30 minutes, followed by staining the tissue slide with DAB (diaminobenzidine tetrahydrochloride, Biogenex). Subsequently, the tissue slide was washed with distilled water and subjected to counter-staining with hematoxylin. The tissue slide was then dehydrated with, 95%, 95%, 100%, and 100% ethanol, in order, for 10 seconds each, and de-waxed with xylene twice for 10 seconds each. The tissue slide was mounted on a glass slide and observed under an optical microscope.

As shown in FIG. 15, it was confirmed that the formation of microvessels was inhibited in the mouse tumor tissues treated with the cell permeable endostatin recombinant proteins ($HM_2E$), as compared to those treated with the vehicle and the control protein (HE).

Effect of the Invention

The cell permeable endostatin recombinant proteins according to the present invention can introduce the angiogenesis inhibitor endostatin into a cell with high efficiency so that the endostatin is maintained at a high concentration inside and outside of the vascular endothelial cell present in tumor tissues. Accordingly, the recombinant proteins of the present invention can effectively inhibit the migration, proliferation, invasion, and tube formation of vascular endothelial cells and strongly block the formation of new microvessels, thereby leading to superior anti-cancer activity, and thus are useful as an anti-cancer agent for treating various cancers.

What is claimed:

1. A cell permeable endostatin recombinant protein comprising an angiogenesis inhibitor endostatin and a macromolecule transduction domain (MTD), wherein the MTD is fused to one terminus or both termini of the endostatin, wherein the MTD comprises an amino acid sequence selected from the group consisting of SEQ ID NOS: 3 to 11.

2. The cell permeable endostatin recombinant protein according to claim 1, wherein the angiogenesis inhibitor endostatin is in a full-length form having an amino acid sequence represented by SEQ ID NO: 2.

3. The cell permeable endostatin recombinant protein according to claim 1, wherein the MTD is selected from the group consisting of:
    a JO-56 MTD having an amino acid sequence represented by SEQ ID NO: 5;
    a JO-73 MTD having an amino acid sequence represented by SEQ ID NO: 8;
    a JO-66 MTD having an amino acid sequence represented by SEQ ID NO: 6;
    a JO-71 MTD having an amino acid sequence represented by SEQ ID NO: 7;
    a JO-85 MTD having an amino acid sequence represented by SEQ ID NO: 9;
    a JO-18 MTD having an amino acid sequence represented by SEQ ID NO: 3;
    a JO-41 MTD having an amino acid sequence represented by SEQ ID NO: 4;
    a JO-135 MTD having an amino acid sequence represented by SEQ ID NO:10; and
    a JO-159 MTD having an amino acid sequence represented by SEQ ID NO: 11.

4. The cell permeable endostatin recombinant protein according to claim 1, wherein a histidine-tag affinity domain is fused to one terminus of the recombinant protein.

5. The cell permeable endostatin recombinant protein according to any one of claims 1 to 2 and 3 to 4, wherein the recombinant protein is selected from the group consisting of:
    a recombinant protein wherein a JO-56 MTD having an amino acid sequence represented by SEQ ID NO: 5 is fused to the N-terminus of a full-length endostatin having an amino acid sequence represented by SEQ ID NO: 2;
    a recombinant protein wherein a JO-56 MTD having an amino acid sequence represented by SEQ ID NO: 5 is fused to the C-terminus of a full-length endostatin having an amino acid sequence represented by SEQ ID NO: 2;
    a recombinant protein wherein a JO-56 MTD having an amino acid sequence represented by SEQ ID NO: 5 is fused to both termini of a full-length endostatin having an amino acid sequence represented by SEQ ID NO: 2;
    a recombinant protein wherein a JO-73 MTD having an amino acid sequence represented by SEQ ID NO: 8 is fused to the N-terminus of a full-length endostatin having an amino acid sequence represented by SEQ ID NO: 2;
    a recombinant protein wherein a JO-73 MTD having an amino acid sequence represented by SEQ ID NO: 8 is fused to the C-terminus of a full-length endostatin having an amino acid sequence represented by SEQ ID NO: 2;
    a recombinant protein wherein a JO-73 MTD having an amino acid sequence represented by SEQ ID NO: 8 is fused to both termini of a full-length endostatin having an amino acid sequence represented by SEQ ID NO: 2;
    a recombinant protein wherein a JO-66 MTD having an amino acid sequence represented by SEQ ID NO: 6 is fused to the N-terminus of a full-length endostatin having an amino acid sequence represented by SEQ ID NO: 2;
    a recombinant protein wherein a JO-71 MTD having an amino acid sequence represented by SEQ ID NO: 7 is fused to the N-terminus of a full-length endostatin having an amino acid sequence represented by SEQ ID NO: 2;
    a recombinant protein wherein a JO-85 MTD having an amino acid sequence represented by SEQ ID NO: 9 is fused to the N-terminus of a full-length endostatin having an amino acid sequence represented by SEQ ID NO: 2;
    a recombinant protein wherein a JO-18 MTD having an amino acid sequence represented by SEQ ID NO: 3 is fused to the N-terminus of a full-length endostatin having an amino acid sequence represented by SEQ ID NO: 2;
    a recombinant protein wherein a JO-41 MTD having an amino acid sequence represented by SEQ ID NO: 4 is fused to the N-terminus of a full-length endostatin having an amino acid sequence represented by SEQ ID NO: 2;
    a recombinant protein wherein a JO-135 MTD having an amino acid sequence represented by SEQ ID NO: 10 is fused to the N-terminus of a full-length endostatin having an amino acid sequence represented by SEQ ID NO: 2; and
    a recombinant protein wherein a JO-159 MTD having an amino acid sequence represented by SEQ ID NO: 11 is fused to the N-terminus of a full-length endostatin having an amino acid sequence represented by SEQ ID NO: 2;
    wherein a histidine-tag is covalently coupled to the N-terminus of all of said recombinant proteins.

6. The cell permeable endostatin recombinant protein according to claim 1, wherein the recombinant protein has an amino acid sequence selected from the group consisting of SEQ ID NOS: 15, 17, 19, 21, 23, 25, 27, 29, 31, 33, 35, 37, and 39.

7. A polynucleotide encoding the cell permeable recombinant protein according to claim 1.

8. The polynucleotide according to claim 7, wherein the polynucleotide has a nucleotide sequence selected from the group consisting of SEQ ID NOS: 14, 16, 18, 20, 22, 24, 26, 28, 30, 32, 34, 36, and 38.

9. A recombinant expression vector comprising the polynucleotide according to claim 7.

10. The recombinant expression vector according to claim 9, wherein the expression vector is selected from the group consisting of:
pHM$_1$E which comprises a polynucleotide having a nucleotide sequence represented by SEQ ID NO: 14 which encodes a cell permeable endostatin recombinant protein fused to a JO-56 MTD;
pHEM$_1$ which comprises a polynucleotide having a nucleotide sequence represented by SEQ ID NO: 16 which encodes a cell permeable endostatin recombinant protein fused to a JO-56 MTD;
pHM$_1$EM$_i$ which comprises a polynucleotide having a nucleotide sequence represented by SEQ ID NO: 18 which encodes a cell permeable endostatin recombinant protein fused to a JO-56 MTD;
pHM$_2$E which comprises a polynucleotide having a nucleotide sequence represented by SEQ ID NO: 20 which encodes a cell permeable endostatin recombinant protein fused to a JO-73 MTD;
pHEM$_2$ which comprises a polynucleotide having a nucleotide sequence represented by SEQ ID NO: 22 which encodes a cell permeable endostatin recombinant protein fused to a JO-73 MTD;
pHM$_2$EM$_2$ which comprises a polynucleotide having a nucleotide sequence represented by SEQ ID NO: 24 which encodes a cell permeable endostatin recombinant protein fused to a JO-73 MTD;
pHM$_3$E which comprises a polynucleotide having a nucleotide sequence represented by SEQ ID NO: 26 which encodes a cell permeable endostatin recombinant protein fused to a JO-66 MTD;
pHM$_4$E which comprises a polynucleotide having a nucleotide sequence represented by SEQ ID NO: 28 which encodes a cell permeable endostatin recombinant protein fused to a JO-71 MTD;
pHM$_5$E which comprises a polynucleotide having a nucleotide sequence represented by SEQ ID NO: 30 which encodes a cell permeable endostatin recombinant protein fused to a JO-85 MTD;
pHM$_6$E which comprises a polynucleotide having a nucleotide sequence represented by SEQ ID NO: 32 which encodes a cell permeable endostatin recombinant protein fused to a JO-18 MTD;
pHM$_7$E which comprises a polynucleotide having a nucleotide sequence represented by SEQ ID NO: 34 which encodes a cell permeable endostatin recombinant protein fused to a JO-41 MTD;
pHM$_8$E which comprises a polynucleotide having a nucleotide sequence represented by SEQ ID NO: 36 which encodes a cell permeable endostatin recombinant protein fused to a JO-135 MTD; and
pHM$_9$E which comprises a polynucleotide having a nucleotide sequence represented by SEQ ID NO: 38 which encodes a cell permeable endostatin recombinant protein fused to a JO-159 MTD.

11. A transformant which is obtained by transformation with the recombinant expression vector according to claim 9.

12. The transformant according to claim 11, wherein the transformant is *E. coli* DH5α/pET-28a(+):HM$_1$E (KCTC-11485BP).

13. The transformant according to claim 11, wherein the transformant is *E. coli* DH5α/pET-28a(+):HM$_2$E (KCTC-11486BP).

14. The transformant according to claim 11, wherein the transformant is *E. coli* DH5α/pET-28a(+):HM$_3$E (KCTC-11487BP).

15. The transformant according to claim 11, wherein the transformant is *E. coli* DH5α/pET-28a(+):HM$_8$E (KCTC-11488BP).

16. A method of producing a cell permeable endostatin recombinant protein according to claim 1 comprising:
culturing the transformant according to claim 11 to express a cell permeable endostatin recombinant protein; and
recovering the expressed cell permeable endostatin recombinant protein from the culture.

17. A pharmaceutical composition for use as an anti-cancer agent comprising the cell permeable endostatin recombinant protein according to claim 1 as an active ingredient and a pharmaceutically acceptable carrier.

18. The pharmaceutical composition according to claim 17, wherein the cell permeable endostatin recombinant protein inhibits the migration, proliferation, invasion, and tube formation of vascular endothelial cells in tumor tissue, and blocks the formation of microvessels, allowing the pharmaceutical composition to exhibit anti-cancer activity.

* * * * *

SEQUENCE LISTING

<160> NUMBER OF SEQ ID NOS: 53

<210> SEQ ID NO 1
<211> LENGTH: 552
<212> TYPE: DNA
<213> ORGANISM: Homo sapiens
<220> FEATURE:
<223> OTHER INFORMATION: Endostatin cDNA sequence

<400> SEQUENCE: 1

```
cacagccacc gcgacttcca gccggtgctc cacctggttg cgctcaacag cccctgtca      60
ggcggcatgc ggggcatccg cggggccgac ttccagtgct ccagcaggc gcgggccgtg     120
gggctggcgg gcaccttccg cgccttcctg tcctcgcgcc tgcaggacct gtacagcatc    180
gtgcgccgtg ccgaccgcgc agccgtgccc atcgtcaacc tcaaggacga gctgctgttt    240
cccagctggg aggctctgtt ctcaggctct gagggtccgc tgaagcccgg ggcacgcatc    300
ttctcctttg acggcaagga cgtcctgagg caccccacct ggcccagaa gagcgtgtgg     360
catggctcgg accccaacgg cgcaggctg accgagagct actgtgagac gtggcggacg    420
gaggctccct cggccacggg ccaggcctcc tcgctgctgg ggggcaggct cctggggcag    480
agtgccgcga gctgccatca cgcctacatc gtgctctgca ttgagaacag cttcatgact    540
gcctccaagt ag                                                         552
```

<210> SEQ ID NO 2
<211> LENGTH: 182
<212> TYPE: PRT
<213> ORGANISM: Homo sapiens
<220> FEATURE:
<223> OTHER INFORMATION: Endostatin amino acid sequence

<400> SEQUENCE: 2

```
His Ser His Arg Asp Phe Glu Pro Val Leu His Leu Val Ala Leu Asn
1               5                   10                  15

Ser Pro Leu Gly Gly Met Arg Gly Ile Arg Gly Ala Asp Phe Gln Cys
            20                  25                  30

Phe Gln Gln Ala Arg Ala Val Gly Leu Ala Gly Thr Phe Arg Ala Phe
        35                  40                  45

Leu Ser Ser Arg Leu Gln Asp Leu Tyr Ser Ile Val Arg Arg Ala Asp
    50                  55                  60

Arg Ala Ala Val Pro Ile Val Asn Leu Lys Asp Glu Leu Leu Phe Pro
65                  70                  75                  80

Ser Trp Glu Ala Leu Phe Ser Gly Ser Glu Gly Pro Leu Lys Pro Gly
                85                  90                  95

Ala Arg Ile Phe Ser Phe Asp Gly Lys Asp Val Leu Arg His Pro Thr
            100                 105                 110

Trp Pro Gln Lys Ser Val Trp His Gly Ser Asp Pro Asn Gly Arg Arg
        115                 120                 125

Leu Thr Glu Ser Tyr Cys Glu Thr Trp Arg Thr Glu Ala Pro Ser Ala
    130                 135                 140

Thr Gly Gln Ala Ser Ser Leu Leu Gly Gly Arg Leu Leu Gly Gln Ser
145                 150                 155                 160

Ala Ala Ser Cys His His Ala Tyr Ile Val Leu Cys Ile Glu Asn Ser
                165                 170                 175

Phe Met Thr Ala Ser Lys
            180
```

-continued

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      JO-18 MTD peptide

<400> SEQUENCE: 3

Ala Ala Leu Ala Leu Gly Val Ala Ala Ala Pro Ala Ala Ala Pro Ala
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      JO-41 MTD peptide

<400> SEQUENCE: 4

Ala Ala Ala Leu Leu Ala Val Ala
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      JO-56 MTD peptide

<400> SEQUENCE: 5

Val Leu Leu Ala Ala Ala Leu Ile Ala
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      JO-66 MTD peptide

<400> SEQUENCE: 6

Ala Ala Ala Leu Ala Ala Ile Ala Val Ile
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      JO-71 MTD peptide

<400> SEQUENCE: 7

Ala Leu Ala Leu Leu Leu Leu Val Pro
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      JO-73 MTD peptide

<400> SEQUENCE: 8

Pro Val Leu Leu Leu Leu Ala Pro
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      JO-85 MTD peptide

<400> SEQUENCE: 9

Leu Leu Ala Ala Ala Ala Ala Leu Leu Leu Ala
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      JO-135 MTD peptide

<400> SEQUENCE: 10

Ala Ala Val Ala Leu Pro Ala Ala Ala Pro
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      JO-159 MTD peptide

<400> SEQUENCE: 11

Ile Ala Ile Ala Ala Ile Pro Ala Ile Leu Ala Leu
1               5                   10

<210> SEQ ID NO 12
<211> LENGTH: 615
<212> TYPE: DNA
<213> ORGANISM: Artificial Sequence
<220> FEATURE:
<223> OTHER INFORMATION: Description of Artificial Sequence: Synthetic
      His-Endostatin cDNA sequence

<400> SEQUENCE: 12
atgggcagca gcaaacatca tcatcatcac agcagcggcc tggtgccgcg cggcagccat      60
atgcacagcc accgcgactt ccagccggtg ctccacctgg ttgcgctcaa cagcccctg     120 tcaggcggca tgcggggcat ccgcggggcc gacttccagt gcttccagca ggcgcgggcc    180
gtggggctgg cggcaccctt ccgcgccttc tgtcctcgc gcctgcagga cctgtacagc     240
atcgtgcgcc gtgccgaccg cgcagccgtg cccatcgtca acctcaagga cgagctgctg    300
tttcccagct gggaggctct gttctcaggc tctgagggtc cgctgaagcc cggggcacgc    360
atcttctcct tgacggcaa ggacgtcctg aggcacccca cctggcccca gaagagcgtg     420
tggcatggct cggaccccaa cgggcgcagg ctgaccgaga gctactgtga cgtggcgg      480 acggaggctc cctcggccac gggccaggcc tcctcgctgc tggggggcag gctcctgggg    540
cagagtgccg cgagctgcca tcacgcctac atcgtgctct gcattgagaa cagcttcatg    600
actgcctcca agtag                                                     615

```
<210> SEQ ID NO 13
<211> LENGTH: 201
<212> TYPE: PRT
<213> ORGANISM: Artificial Sequence
<220> FEATURE:
<223> OTHER INFORMATION: Description of Artificial Sequence: Synthetic
      His-Endostatin Amino Acid Sequence

<400> SEQUENCE: 13

Met Gly Ser Ser Lys His His His His Ser Ser Gly Leu Val Pro
1               5                   10                  15

Arg Gly Ser His Ser His Arg Asp Phe Glu Pro Val Leu His Leu Val
            20                  25                  30

Ala Leu Asn Ser Pro Leu Gly Gly Met Arg Gly Ile Arg Gly Ala Asp
        35                  40                  45

Phe Gln Cys Phe Gln Gln Ala Arg Ala Val Gly Leu Ala Gly Thr Phe
    50                  55                  60

Arg Ala Phe Leu Ser Ser Arg Leu Gln Asp Leu Tyr Ser Ile Val Arg
65                  70                  75                  80

Arg Ala Asp Arg Ala Ala Val Pro Ile Val Asn Leu Lys Asp Glu Leu
                85                  90                  95

Leu Phe Pro Ser Trp Glu Ala Leu Phe Ser Gly Ser Glu Gly Pro Leu
            100                 105                 110

Lys Pro Gly Ala Arg Ile Phe Ser Phe Asp Gly Lys Asp Val Leu Arg
        115                 120                 125

His Pro Thr Trp Pro Gln Lys Ser Val Trp His Gly Ser Asp Pro Asn
    130                 135                 140

Gly Arg Arg Leu Thr Glu Ser Tyr Cys Glu Thr Trp Arg Thr Glu Ala
145                 150                 155                 160

Pro Ser Ala Thr Gly Gln Ala Ser Ser Leu Leu Gly Gly Arg Leu Leu
                165                 170                 175

Gly Gln Ser Ala Ala Ser Cys His His Ala Tyr Ile Val Leu Cys Ile
            180                 185                 190

Glu Asn Ser Phe Met Thr Ala Ser Lys
        195                 200

<210> SEQ ID NO 14
<211> LENGTH: 642
<212> TYPE: DNA
<213> ORGANISM: Artificial Sequence
<220> FEATURE:
<223> OTHER INFORMATION: Description of Artificial Sequence: Synthetic
      His-JO-56 MTD-Endostatin cDNA Sequence

<400> SEQUENCE: 14
atgggcagca gcaaacatca tcatcatcac agcagcggcc tggtgccgcg cggcagccat      60
atggtgctgc tggcggcggc gctgattgcg cacagccacc gcgacttcca gccggtgctc     120
cacctggttg cgctcaacag ccccctgtca ggcggcatgc ggggcatccg cggggccgac     180
ttccagtgct tccagcaggc gcgggccgtg gggctggcgg gcaccttccg cgccttcctg     240
tcctcgcgcc tgcaggacct gtacagcatc gtgcgccgtg ccgaccgcgc agccgtgccc     300
atcgtcaacc tcaaggacga gctgctgttt cccagctggg aggctctgtt ctcaggctct     360
gagggtccgc tgaagcccgg ggcacgcatc ttctcctttg acggcaagga cgtcctgagg     420
caccccacct ggccccagaa gagcgtgtgg catggctcgg accccaacgg cgcaggctg      480 accgagagct actgtgagac gtggcggacg gaggctccct cggccacggg ccaggcctcc     540
tcgctgctgg ggggcaggct cctggggcag agtgccgcga gctgccatca cgcctacatc     600
```
gtgctctgca ttgagaacag cttcatgact gcctccaagt ag        642

<210> SEQ ID NO 15
<211> LENGTH: 210
<212> TYPE: PRT
<213> ORGANISM: Artificial Sequence
<220> FEATURE:
<223> OTHER INFORMATION: Description of Artificial Sequence: Synthetic
His-JO-56 MTD-Endostatin Amino Acid Sequence

<400> SEQUENCE: 15

Met Gly Ser Ser Lys His His His His Ser Ser Gly Leu Val Pro
1               5                   10                  15

Arg Gly Ser Val Leu Leu Ala Ala Ala Leu Ile Ala His Ser His Arg
            20                  25                  30

Asp Phe Glu Pro Val Leu His Leu Val Ala Leu Asn Ser Pro Leu Gly
        35                  40                  45

Gly Met Arg Gly Ile Arg Gly Ala Asp Phe Gln Cys Phe Gln Gln Ala
    50                  55                  60

Arg Ala Val Gly Leu Ala Gly Thr Phe Arg Ala Phe Leu Ser Ser Arg
65                  70                  75                  80

Leu Gln Asp Leu Tyr Ser Ile Val Arg Arg Ala Asp Arg Ala Ala Val
                85                  90                  95

Pro Ile Val Asn Leu Lys Asp Glu Leu Leu Phe Pro Ser Trp Glu Ala
            100                 105                 110

Leu Phe Ser Gly Ser Glu Gly Pro Leu Lys Pro Gly Ala Arg Ile Phe
        115                 120                 125

Ser Phe Asp Gly Lys Asp Val Leu Arg His Pro Thr Trp Pro Gln Lys
    130                 135                 140

Ser Val Trp His Gly Ser Asp Pro Asn Gly Arg Arg Leu Thr Glu Ser
145                 150                 155                 160

Tyr Cys Glu Thr Trp Arg Thr Glu Ala Pro Ser Ala Thr Gly Gln Ala
                165                 170                 175

Ser Ser Leu Leu Gly Gly Arg Leu Leu Gly Gln Ser Ala Ala Ser Cys
            180                 185                 190

His His Ala Tyr Ile Val Leu Cys Ile Glu Asn Ser Phe Met Thr Ala
        195                 200                 205

Ser Lys
    210

<210> SEQ ID NO 16
<211> LENGTH: 642
<212> TYPE: DNA
<213> ORGANISM: Artificial Sequence
<220> FEATURE:
<223> OTHER INFORMATION: Description of Artificial Sequence: Synthetic
His-Endostaitn-JO-56 MTD cDNA Sequence

<400> SEQUENCE: 16
atgggcagca gcaaacatca tcatcatcac agcagcggcc tggtgccgcg cggcagccat    60
atgcacagcc accgcgactt ccagccggtg ctccacctgg ttgcgctcaa cagcccctg    120 tcaggcggca tgcggggcat ccgcggggcc gacttccagt gcttccagca ggcgcgggcc    180
gtggggctgg cgggcacctt ccgcgccttc ctgtcctcgc gcctgcagga cctgtacagc    240
atcgtgcgcc gtgccgaccg cgcagccgtg cccatcgtca acctcaagga cgagctgctg    300
tttcccagct gggaggctct gttctcaggc tctgagggtc cgctgaagcc ggggcacgc    360 atcttctcct tgacggcaa ggacgtcctg aggcaccca cctggcccca gaagagcgtg    420

```
tggcatggct cggaccccaa cgggcgcagg ctgaccgaga gctactgtga cgtggcgg    480 acggaggctc cctcggccac gggccaggcc tcctcgctgc tggggggcag gctcctgggg    540
cagagtgccg cgagctgcca tcacgcctac atcgtgctct gcattgagaa cagcttcatg    600
actgcctcca aggtgctgct ggcggcggcg ctgattgcgt ag                       642
```

```
<210> SEQ ID NO 17
<211> LENGTH: 210
<212> TYPE: PRT
<213> ORGANISM: Artificial Sequence
<220> FEATURE:
<223> OTHER INFORMATION: Description of Artificial Sequence: Synthetic
      His-Endostatin-JO-56 MTD Amino Acid Sequence

<400> SEQUENCE: 17
```

Met Gly Ser Ser Lys His His His His Ser Ser Gly Leu Val Pro
1               5                   10                  15

Arg Gly Ser His Ser His Arg Asp Phe Glu Pro Val Leu His Leu Val
            20                  25                  30

Ala Leu Asn Ser Pro Leu Gly Gly Met Arg Gly Ile Arg Gly Ala Asp
        35                  40                  45

Phe Gln Cys Phe Gln Gln Ala Arg Ala Val Gly Leu Ala Gly Thr Phe
50                  55                  60

Arg Ala Phe Leu Ser Ser Arg Leu Gln Asp Leu Tyr Ser Ile Val Arg
65                  70                  75                  80

Arg Ala Asp Arg Ala Ala Val Pro Ile Val Asn Leu Lys Asp Glu Leu
                85                  90                  95

Leu Phe Pro Ser Trp Glu Ala Leu Phe Ser Gly Ser Glu Gly Pro Leu
            100                 105                 110

Lys Pro Gly Ala Arg Ile Phe Ser Phe Asp Gly Lys Asp Val Leu Arg
        115                 120                 125

His Pro Thr Trp Pro Gln Lys Ser Val Trp His Gly Ser Asp Pro Asn
130                 135                 140

Gly Arg Arg Leu Thr Glu Ser Tyr Cys Glu Thr Trp Arg Thr Glu Ala
145                 150                 155                 160

Pro Ser Ala Thr Gly Gln Ala Ser Ser Leu Leu Gly Gly Arg Leu Leu
                165                 170                 175

Gly Gln Ser Ala Ala Ser Cys His His Ala Tyr Ile Val Leu Cys Ile
            180                 185                 190

Glu Asn Ser Phe Met Thr Ala Ser Lys Val Leu Leu Ala Ala Ala Leu
        195                 200                 205

Ile Ala
    210

```
<210> SEQ ID NO 18
<211> LENGTH: 669
<212> TYPE: DNA
<213> ORGANISM: Artificial Sequence
<220> FEATURE:
<223> OTHER INFORMATION: Description of Artificial Sequence: Synthetic
      His-JO-56 MTD-Endostatin-JO-56 MTD cDNA Sequence

<400> SEQUENCE: 18
```

```
atgggcagca gcaaacatca tcatcatcac agcagcggcc tggtgccgcg cggcagccat    60
atggtgctgc tggcggcggc gctgattgcg cacagccacc gcgacttcca gccggtgctc    120
cacctggttg cgctcaacag cccccctgtca ggcggcatgc ggggcatccg cggggccgac    180
ttccagtgct tccagcaggc gcgggccgtg ggctggcgg gcaccttccg cgccttcctg    240
```

```
tcctcgcgcc tgcaggacct gtacagcatc gtgcgccgtg ccgaccgcgc agccgtgccc      300
atcgtcaacc tcaaggacga gctgctgttt cccagctggg aggctctgtt ctcaggctct      360
gagggtccgc tgaagcccgg ggcacgcatc ttctcctttg acggcaagga cgtcctgagg      420
caccccacct ggccccagaa gagcgtgtgg catggctcgg accccaacgg cgcaggctg       480 accgagagct actgtgagac gtggcggacg gaggctccct cggccacggg ccaggcctcc      540
tcgctgctgg ggcaggct cctggggcag agtgccgcga gctgccatca cgcctacatc        600
gtgctctgca ttgagaacag cttcatgact gcctccaagg tgctgctggc ggcggcgctg      660
attgcgtag                                                              669
```

```
<210> SEQ ID NO 19
<211> LENGTH: 219
<212> TYPE: PRT
<213> ORGANISM: Artificial Sequence
<220> FEATURE:
<223> OTHER INFORMATION: Description of Artificial Sequence: Synthetic
      His-JO-56 MTD-Endostatin-JO-56 MTD Amino Acid Sequence

<400> SEQUENCE: 19

Met Gly Ser Ser Lys His His His His Ser Ser Gly Leu Val Pro
1               5                   10                  15

Arg Gly Ser Val Leu Leu Ala Ala Ala Leu Ile Ala His Ser His Arg
                20                  25                  30

Asp Phe Glu Pro Val Leu His Leu Val Ala Leu Asn Ser Pro Leu Gly
            35                  40                  45

Gly Met Arg Gly Ile Arg Gly Ala Asp Phe Gln Cys Phe Gln Gln Ala
    50                  55                  60

Arg Ala Val Gly Leu Ala Gly Thr Phe Arg Ala Phe Leu Ser Ser Arg
65                  70                  75                  80

Leu Gln Asp Leu Tyr Ser Ile Val Arg Arg Ala Asp Arg Ala Ala Val
                85                  90                  95

Pro Ile Val Asn Leu Lys Asp Glu Leu Leu Phe Pro Ser Trp Glu Ala
            100                 105                 110

Leu Phe Ser Gly Ser Glu Gly Pro Leu Lys Pro Gly Ala Arg Ile Phe
        115                 120                 125

Ser Phe Asp Gly Lys Asp Val Leu Arg His Pro Thr Trp Pro Gln Lys
130                 135                 140

Ser Val Trp His Gly Ser Asp Pro Asn Gly Arg Arg Leu Thr Glu Ser
145                 150                 155                 160

Tyr Cys Glu Thr Trp Arg Thr Glu Ala Pro Ser Ala Thr Gly Gln Ala
                165                 170                 175

Ser Ser Leu Leu Gly Gly Arg Leu Leu Gly Gln Ser Ala Ala Ser Cys
            180                 185                 190

His His Ala Tyr Ile Val Leu Cys Ile Glu Asn Ser Phe Met Thr Ala
        195                 200                 205

Ser Lys Val Leu Leu Ala Ala Ala Leu Ile Ala
    210                 215

<210> SEQ ID NO 20
<211> LENGTH: 639
<212> TYPE: DNA
<213> ORGANISM: Artificial Sequence
<220> FEATURE:
<223> OTHER INFORMATION: Description of Artificial Sequence: Synthetic
      His-JO-73 MTD-Endostatin cDNA Sequence

<400> SEQUENCE: 20
```

```
atgggcagca gcaaacatca tcatcatcac agcagcggcc tggtgccgcg cggcagccat    60
atgccggtgc tgctgctgct ggcgccgcac agccaccgcg acttccagcc ggtgctccac   120
ctggttgcgc tcaacagccc cctgtcaggc ggcatgcggg catccgcgg ggccgacttc   180
cagtgcttcc agcaggcgcg ggccgtgggg ctggcgggca ccttccgcgc cttcctgtcc   240
tcgcgcctgc aggacctgta cagcatcgtg cgccgtgccg accgcgcagc cgtgcccatc   300
gtcaacctca aggacgagct gctgtttccc agctgggagg ctctgttctc aggctctgag   360
ggtccgctga agcccggggc acgcatcttc tcctttgacg gcaaggacgt cctgaggcac   420
cccacctggc cccagaagag cgtgtggcat ggctcggacc ccaacgggcg caggctgacc   480
gagagctact gtgagacgtg gcggacggag gctccctcgg ccacgggcca ggcctcctcg   540
ctgctggggg gcaggctcct ggggcagagt gccgcgagct gccatcacgc ctacatcgtg   600
ctctgcattg agaacagctt catgactgcc tccaagtag                         639
```

<210> SEQ ID NO 21
<211> LENGTH: 209
<212> TYPE: PRT
<213> ORGANISM: Artificial Sequence
<220> FEATURE:
<223> OTHER INFORMATION: Description of Artificial Sequence: Synthetic His-JO-73 MTD-Endostatin Amino Acid Sequence

<400> SEQUENCE: 21

```
Met Gly Ser Ser Lys His His His His Ser Ser Gly Leu Val Pro
1               5                   10                  15

Arg Gly Ser Pro Val Leu Leu Leu Ala Pro His Ser His Arg Asp
            20                  25                  30

Phe Glu Pro Val Leu His Leu Val Ala Leu Asn Ser Pro Leu Gly Gly
        35                  40                  45

Met Arg Gly Ile Arg Gly Ala Asp Phe Gln Cys Phe Gln Gln Ala Arg
    50                  55                  60

Ala Val Gly Leu Ala Gly Thr Phe Arg Ala Phe Leu Ser Ser Arg Leu
65                  70                  75                  80

Gln Asp Leu Tyr Ser Ile Val Arg Arg Ala Asp Arg Ala Ala Val Pro
                85                  90                  95

Ile Val Asn Leu Lys Asp Glu Leu Leu Phe Pro Ser Trp Glu Ala Leu
            100                 105                 110

Phe Ser Gly Ser Glu Gly Pro Leu Lys Pro Gly Ala Arg Ile Phe Ser
        115                 120                 125

Phe Asp Gly Lys Asp Val Leu Arg His Pro Thr Trp Pro Gln Lys Ser
    130                 135                 140

Val Trp His Gly Ser Asp Pro Asn Gly Arg Arg Leu Thr Glu Ser Tyr
145                 150                 155                 160

Cys Glu Thr Trp Arg Thr Glu Ala Pro Ser Ala Thr Gly Gln Ala Ser
                165                 170                 175

Ser Leu Leu Gly Gly Arg Leu Leu Gly Gln Ser Ala Ala Ser Cys His
            180                 185                 190

His Ala Tyr Ile Val Leu Cys Ile Glu Asn Ser Phe Met Thr Ala Ser
        195                 200                 205

Lys
```

<210> SEQ ID NO 22
<211> LENGTH: 639
<212> TYPE: DNA
<213> ORGANISM: Artificial Sequence
<220> FEATURE:

<223> OTHER INFORMATION: Description of Artificial Sequence: Synthetic
His-Endostatin-JO-73 MTD cDNA Sequence

<400> SEQUENCE: 22

```
atgggcagca gcaaacatca tcatcatcac agcagcggcc tggtgccgcg cggcagccat      60
atgcacagcc accgcgactt ccagccggtg ctccacctgg ttgcgctcaa cagcccctg     120
tcaggcggca tgcggggcat ccgcggggcc gacttccagt gcttccagca ggcgcgggcc    180
gtggggctgg cgggcacctt ccgcgccttc ctgtcctcgc gcctgcagga cctgtacagc    240
atcgtgcgcc gtgccgaccg cgcagccgtg cccatcgtca acctcaagga cgagctgctg    300
tttcccagct gggaggctct gttctcaggc tctgagggtc cgctgaagcc cggggcacgc    360
atcttctcct tgacggcaa ggacgtcctg aggcacccca cctggcccca gaagagcgtg    420
tggcatggct cggaccccaa cgggcgcagg ctgaccgaga gctactgtga cgtggcgg      480
acggaggctc cctcggccac gggccaggcc tcctcgctgc tggggggcag gctcctgggg    540
cagagtgccg cgagctgcca tcacgcctac atcgtgctct gcattgagaa cagcttcatg    600
actgcctcca agccggtgct gctgctgctg gcgccgtag                          639
```

<210> SEQ ID NO 23
<211> LENGTH: 209
<212> TYPE: PRT
<213> ORGANISM: Artificial Sequence
<220> FEATURE:
<223> OTHER INFORMATION: Description of Artificial Sequence: Synthetic
His-Endostatin-JO-73 MTD Amino Acid Sequence

<400> SEQUENCE: 23

```
Met Gly Ser Ser Lys His His His His Ser Ser Gly Leu Val Pro
1               5                  10                  15

Arg Gly Ser His Ser His Arg Asp Phe Glu Pro Val Leu His Leu Val
            20                  25                  30

Ala Leu Asn Ser Pro Leu Gly Gly Met Arg Gly Ile Arg Gly Ala Asp
        35                  40                  45

Phe Gln Cys Phe Gln Gln Ala Arg Ala Val Gly Leu Ala Gly Thr Phe
    50                  55                  60

Arg Ala Phe Leu Ser Ser Arg Leu Gln Asp Leu Tyr Ser Ile Val Arg
65                  70                  75                  80

Arg Ala Asp Arg Ala Ala Val Pro Ile Val Asn Leu Lys Asp Glu Leu
                85                  90                  95

Leu Phe Pro Ser Trp Glu Ala Leu Phe Ser Gly Ser Glu Gly Pro Leu
            100                 105                 110

Lys Pro Gly Ala Arg Ile Phe Ser Phe Asp Gly Lys Asp Val Leu Arg
        115                 120                 125

His Pro Thr Trp Pro Gln Lys Ser Val Trp His Gly Ser Asp Pro Asn
    130                 135                 140

Gly Arg Arg Leu Thr Glu Ser Tyr Cys Glu Thr Trp Arg Thr Glu Ala
145                 150                 155                 160

Pro Ser Ala Thr Gly Gln Ala Ser Ser Leu Leu Gly Gly Arg Leu Leu
                165                 170                 175

Gly Gln Ser Ala Ala Ser Cys His His Ala Tyr Ile Val Leu Cys Ile
            180                 185                 190

Glu Asn Ser Phe Met Thr Ala Ser Lys Pro Val Leu Leu Leu Leu Ala
        195                 200                 205

Pro
```

```
<210> SEQ ID NO 24
<211> LENGTH: 663
<212> TYPE: DNA
<213> ORGANISM: Artificial Sequence
<220> FEATURE:
<223> OTHER INFORMATION: Description of Artificial Sequence: Synthetic
      His-JO-73 MTD-Endostatin-JO-73 MTD cDNA Sequence

<400> SEQUENCE: 24
atgggcagca gcaaacatca tcatcatcac agcagcggcc tggtgccgcg cggcagccat    60
atgccggtgc tgctgctgct ggcgccgcac agccaccgcg acttccagcc ggtgctccac   120
ctggttgcgc tcaacagccc cctgtcaggc ggcatgcggg gcatccgcgg ggccgacttc   180
cagtgcttcc agcaggcgcg ggccgtgggg ctggcgggca ccttccgcgc cttcctgtcc   240 cgcgcctgc aggacctgta cagcatcgtg cgccgtgccg accgcgcagc cgtgcccatc    300
gtcaacctca aggacgagct gctgtttccc agctgggagg ctctgttctc aggctctgag   360
ggtccgctga agcccggggc acgcatcttc tcctttgacg gcaaggacgt cctgaggcac   420
cccacctggc cccagaagag cgtgtggcat ggctcggacc ccaacgggcg caggctgacc   480
gagagctact gtgagacgtg gcggacggag gctccctcgg ccacgggcca ggcctcctcg   540
ctgctggggg gcaggctcct ggggcagagt gccgcgagct gccatcacgc ctacatcgtg   600
ctctgcattg agaacagctt catgactgcc tccaagccgg tgctgctgct gctggcgccg   660
tag                                                                  663

<210> SEQ ID NO 25
<211> LENGTH: 217
<212> TYPE: PRT
<213> ORGANISM: Artificial Sequence
<220> FEATURE:
<223> OTHER INFORMATION: Description of Artificial Sequence: Synthetic
      His-JO-73 MTD-Endostatin-JO-73 MTD Amino Acid Sequence

<400> SEQUENCE: 25

Met Gly Ser Ser Lys His His His His Ser Ser Gly Leu Val Pro
1               5                   10                  15

Arg Gly Ser Pro Val Leu Leu Leu Leu Ala Pro His Ser His Arg Asp
            20                  25                  30

Phe Glu Pro Val Leu His Leu Val Ala Leu Asn Ser Pro Leu Gly Gly
        35                  40                  45

Met Arg Gly Ile Arg Gly Ala Asp Phe Gln Cys Phe Gln Gln Ala Arg
    50                  55                  60

Ala Val Gly Leu Ala Gly Thr Phe Arg Ala Phe Leu Ser Arg Leu
65                  70                  75                  80

Gln Asp Leu Tyr Ser Ile Val Arg Arg Ala Asp Arg Ala Ala Val Pro
                85                  90                  95

Ile Val Asn Leu Lys Asp Glu Leu Leu Phe Pro Ser Trp Glu Ala Leu
            100                 105                 110

Phe Ser Gly Ser Glu Gly Pro Leu Lys Pro Gly Ala Arg Ile Phe Ser
        115                 120                 125

Phe Asp Gly Lys Asp Val Leu Arg His Pro Thr Trp Pro Gln Lys Ser
    130                 135                 140

Val Trp His Gly Ser Asp Pro Asn Gly Arg Arg Leu Thr Glu Ser Tyr
145                 150                 155                 160

Cys Glu Thr Trp Arg Thr Glu Ala Pro Ser Ala Thr Gly Gln Ala Ser
                165                 170                 175

Ser Leu Leu Gly Gly Arg Leu Leu Gly Gln Ser Ala Ala Ser Cys His
            180                 185                 190
```

His Ala Tyr Ile Val Leu Cys Ile Glu Asn Ser Phe Met Thr Ala Ser
            195                 200                 205

Lys Pro Val Leu Leu Leu Ala Pro
    210                 215

<210> SEQ ID NO 26
<211> LENGTH: 645
<212> TYPE: DNA
<213> ORGANISM: Artificial Sequence
<220> FEATURE:
<223> OTHER INFORMATION: Description of Artificial Sequence: Synthetic
      His-JO-66 MTD-Endostatin cDNA Sequence

<400> SEQUENCE: 26
atgggcagca gcaaacatca tcatcatcac agcagcggcc tggtgccgcg cggcagccat      60
atggcggcgg cgctggcggc gattgcggtg attcacagcc accgcgactt ccagccggtg     120
ctccacctgg ttgcgctcaa cagcccctg tcaggcggca tgcggggcat ccgcggggcc     180
gacttccagt gcttccagca ggcgcgggcc gtggggctgg cgggcacctt ccgcgccttc     240
ctgtcctcgc gcctgcagga cctgtacagc atcgtgcgcc gtgccgaccg cgcagccgtg     300
cccatcgtca acctcaagga cgagctgctg tttcccagct gggaggctct gttctcaggc     360
tctgagggtc cgctgaagcc cggggcacgc atcttctcct ttgacggcaa ggacgtcctg     420
aggcacccca cctggcccca gaagagcgtg tggcatggct cggaccccaa cgggcgcagg     480
ctgaccgaga gctactgtga cacggaggcg acggaggctc cctcggccac gggccaggcc     540
tcctcgctgc tgggggcag gctcctgggg cagagtgccg cgagctgcca tcacgcctac     600
atcgtgctct gcattgagaa cagcttcatg actgcctcca agtag                    645

<210> SEQ ID NO 27
<211> LENGTH: 211
<212> TYPE: PRT
<213> ORGANISM: Artificial Sequence
<220> FEATURE:
<223> OTHER INFORMATION: Description of Artificial Sequence: Synthetic
      His-JO-66 MTD-Endostatin Amino Acid Sequence

<400> SEQUENCE: 27

Met Gly Ser Ser Lys His His His His Ser Ser Gly Leu Val Pro
1               5                  10                  15

Arg Gly Ser Ala Ala Ala Leu Ala Ala Ile Ala Val Ile His Ser His
                20                  25                  30

Arg Asp Phe Glu Pro Val Leu His Leu Val Ala Leu Asn Ser Pro Leu
            35                  40                  45

Gly Gly Met Arg Gly Ile Arg Gly Ala Asp Phe Gln Cys Phe Gln Gln
    50                  55                  60

Ala Arg Ala Val Gly Leu Ala Gly Thr Phe Arg Ala Phe Leu Ser Ser
65                  70                  75                  80

Arg Leu Gln Asp Leu Tyr Ser Ile Val Arg Arg Ala Asp Arg Ala Ala
                85                  90                  95

Val Pro Ile Val Asn Leu Lys Asp Glu Leu Leu Phe Pro Ser Trp Glu
            100                 105                 110

Ala Leu Phe Ser Gly Ser Glu Gly Pro Leu Lys Pro Gly Ala Arg Ile
        115                 120                 125

Phe Ser Phe Asp Gly Lys Asp Val Leu Arg His Pro Thr Trp Pro Gln
    130                 135                 140

Lys Ser Val Trp His Gly Ser Asp Pro Asn Gly Arg Arg Leu Thr Glu
145                 150                 155                 160

```
Ser Tyr Cys Glu Thr Trp Arg Thr Glu Ala Pro Ser Ala Thr Gly Gln
                165                 170                 175

Ala Ser Ser Leu Leu Gly Gly Arg Leu Leu Gly Gln Ser Ala Ala Ser
            180                 185                 190

Cys His His Ala Tyr Ile Val Leu Cys Ile Glu Asn Ser Phe Met Thr
        195                 200                 205

Ala Ser Lys
    210

<210> SEQ ID NO 28
<211> LENGTH: 642
<212> TYPE: DNA
<213> ORGANISM: Artificial Sequence
<220> FEATURE:
<223> OTHER INFORMATION: Description of Artificial Sequence: Synthetic
      His-JO-71 MTD-Endostatin cDNA Sequence

<400> SEQUENCE: 28
atgggcagca gcaaacatca tcatcatcac agcagcggcc tggtgccgcg cggcagccat      60
atggcgctgg cgctgctgct gctggtgccg cacagccacc gcgacttcca gccggtgctc     120
cacctggttg cgctcaacag cccccctgtca ggcggcatgc ggggcatccg cggggccgac    180
ttccagtgct tccagcaggc gcgggccgtg gggctggcgg caccttccg cgccttcctg      240 tcctcgcgcc tgcaggacct gtacagcatc gtgcgccgtg ccgaccgcgc agccgtgccc    300
atcgtcaacc tcaaggacga gctgctgttt cccagctggg aggctctgtt ctcaggctct    360
gagggtccgc tgaagcccgg ggcacgcatc ttctcctttg acggcaagga cgtcctgagg    420 cacccccacct ggccccagaa gagcgtgtgg catggctcgg accccaacgg cgcaggctg    480 accgagagct actgtgagac gtggcggacg gaggctccct cggccacggg ccaggcctcc    540
tcgctgctgg ggggcaggct cctggggcag agtgccgcga gctgccatca cgcctacatc    600
gtgctctgca ttgagaacag cttcatgact gcctccaagt ag                       642

<210> SEQ ID NO 29
<211> LENGTH: 210
<212> TYPE: PRT
<213> ORGANISM: Artificial Sequence
<220> FEATURE:
<223> OTHER INFORMATION: Description of Artificial Sequence: Synthetic
      His-JO-71 MTD-Endostatin Amino Acid Sequence

<400> SEQUENCE: 29

Met Gly Ser Ser Lys His His His His Ser Ser Gly Leu Val Pro
1               5                   10                  15

Arg Gly Ser Ala Leu Ala Leu Leu Leu Val Pro His Ser His Arg
            20                  25                  30

Asp Phe Glu Pro Val Leu His Leu Val Ala Leu Asn Ser Pro Leu Gly
        35                  40                  45

Gly Met Arg Gly Ile Arg Gly Ala Asp Phe Gln Cys Phe Gln Gln Ala
    50                  55                  60

Arg Ala Val Gly Leu Ala Gly Thr Phe Arg Ala Phe Leu Ser Ser Arg
65                  70                  75                  80

Leu Gln Asp Leu Tyr Ser Ile Val Arg Arg Ala Asp Arg Ala Ala Val
                85                  90                  95

Pro Ile Val Asn Leu Lys Asp Glu Leu Leu Phe Pro Ser Trp Glu Ala
            100                 105                 110

Leu Phe Ser Gly Ser Glu Gly Pro Leu Lys Pro Gly Ala Arg Ile Phe
        115                 120                 125
```

Ser Phe Asp Gly Lys Asp Val Leu Arg His Pro Thr Trp Pro Gln Lys
       130                 135                 140

Ser Val Trp His Gly Ser Asp Pro Asn Gly Arg Arg Leu Thr Glu Ser
145                 150                 155                 160

Tyr Cys Glu Thr Trp Arg Thr Glu Ala Pro Ser Ala Thr Gly Gln Ala
                165                 170                 175

Ser Ser Leu Leu Gly Gly Arg Leu Leu Gly Gln Ser Ala Ala Ser Cys
            180                 185                 190

His His Ala Tyr Ile Val Leu Cys Ile Glu Asn Ser Phe Met Thr Ala
        195                 200                 205

Ser Lys
    210

<210> SEQ ID NO 30
<211> LENGTH: 648
<212> TYPE: DNA
<213> ORGANISM: Artificial Sequence
<220> FEATURE:
<223> OTHER INFORMATION: Description of Artificial Sequence: Synthetic
      His-JO-85 MTD-Endostatin cDNA Sequence

<400> SEQUENCE: 30
atgggcagca gcaaacatca tcatcatcac agcagcggcc tggtgccgcg cggcagccat      60
atgctgctgg cggcggcggc ggcgctgctg ctggcgcaca gccaccgcga cttccagccg     120
gtgctccacc tggttgcgct caacagcccc ctgtcaggcg gcatgcgggg catccgcggg     180
gccgacttcc agtgcttcca gcaggcgcgg gccgtggggc tggcgggcac cttccgcgcc     240
ttcctgtcct cgcgcctgca ggacctgtac agcatcgtgc gccgtgccga ccgcgcagcc     300
gtgcccatcg tcaacctcaa ggacgagctg ctgtttccca gctgggaggc tctgttctca     360
ggctctgagg tccgctgaa gcccggggca cgcatcttct cctttgacgg caaggacgtc     420
ctgaggcacc ccacctggcc ccagaagagc gtgtggcatg gctcggaccc caacgggcgc     480
aggctgaccg agagctactg tgagacgtgg cggacggagg ctccctcggc cacgggccag     540
gcctcctcgc tgctgggggg caggctcctg ggcagagtg ccgcgagctg ccatcacgcc     600
tacatcgtgc tctgcattga aacagcttc atgactgcct ccaagtag                   648

<210> SEQ ID NO 31
<211> LENGTH: 212
<212> TYPE: PRT
<213> ORGANISM: Artificial Sequence
<220> FEATURE:
<223> OTHER INFORMATION: Description of Artificial Sequence: Synthetic
      His-JO-85 MTD-Endostatin Amino Acid Sequence

<400> SEQUENCE: 31

Met Gly Ser Ser Lys His His His His His Ser Ser Gly Leu Val Pro
1               5                   10                  15

Arg Gly Ser Leu Leu Ala Ala Ala Ala Ala Leu Leu Leu Ala His Ser
            20                  25                  30

His Arg Asp Phe Glu Pro Val Leu His Leu Val Ala Leu Asn Ser Pro
        35                  40                  45

Leu Gly Gly Met Arg Gly Ile Arg Gly Ala Asp Phe Gln Cys Phe Gln
    50                  55                  60

Gln Ala Arg Ala Val Gly Leu Ala Gly Thr Phe Arg Ala Phe Leu Ser
65                  70                  75                  80

Ser Arg Leu Gln Asp Leu Tyr Ser Ile Val Arg Arg Ala Asp Arg Ala
                85                  90                  95

```
Ala Val Pro Ile Val Asn Leu Lys Asp Glu Leu Leu Phe Pro Ser Trp
            100                 105                 110

Glu Ala Leu Phe Ser Gly Ser Glu Gly Pro Leu Lys Pro Gly Ala Arg
        115                 120                 125

Ile Phe Ser Phe Asp Gly Lys Asp Val Leu Arg His Pro Thr Trp Pro
    130                 135                 140

Gln Lys Ser Val Trp His Gly Ser Asp Pro Asn Gly Arg Arg Leu Thr
145                 150                 155                 160

Glu Ser Tyr Cys Glu Thr Trp Arg Thr Glu Ala Pro Ser Ala Thr Gly
                165                 170                 175

Gln Ala Ser Ser Leu Leu Gly Gly Arg Leu Leu Gly Gln Ser Ala Ala
            180                 185                 190

Ser Cys His His Ala Tyr Ile Val Leu Cys Ile Glu Asn Ser Phe Met
            195                 200                 205

Thr Ala Ser Lys
    210
```

<210> SEQ ID NO 32
<211> LENGTH: 663
<212> TYPE: DNA
<213> ORGANISM: Artificial Sequence
<220> FEATURE:
<223> OTHER INFORMATION: Description of Artificial Sequence: Synthetic
      His-JO-18 MTD-Endostatin cDNA Sequence

<400> SEQUENCE: 32

```
atgggcagca gcaaacatca tcatcatcac agcagcggcc tggtgccgcg cggcagccat      60
atggcggcgc tggcgctggg cgtggcggcg gcgccggcgg cggcgccggc gcacagccac     120
cgcgacttcc agccggtgct ccacctggtt gcgctcaaca gccccctgtc aggcggcatg     180
cggggcatcc gcggggccga cttccagtgc ttccagcagg cgcgggccgt ggggctggcg     240
ggcaccttcc gcgccttcct gtcctcgcgc ctgcaggacc tgtacagcat cgtgcgccgt     300
gccgaccgcg cagccgtgcc catcgtcaac ctcaaggacg agctgctgtt cccagctgg      360
gaggctctgt tctcaggctc tgagggtccg ctgaagcccg ggcacgcat cttctccttt      420
gacggcaagg acgtcctgag gcaccccacc tggccccaga gagcgtgtg catggctcg      480
gaccccaacg gcgcaggct gaccgagagc tactgtgaga cgtggcggac ggaggctccc     540
tcggccacgg gccaggcctc ctcgctgctg ggggcaggc tcctggggca gagtgccgcg    600
agctgccatc acgcctacat cgtgctctgc attgagaaca gcttcatgac tgcctccaag     660
tag                                                                  663
```

<210> SEQ ID NO 33
<211> LENGTH: 217
<212> TYPE: PRT
<213> ORGANISM: Artificial Sequence
<220> FEATURE:
<223> OTHER INFORMATION: Description of Artificial Sequence: Synthetic
      His-JO-18 MTD-Endostatin Amino Acid Sequence

<400> SEQUENCE: 33

```
Met Gly Ser Ser Lys His His His His Ser Ser Gly Leu Val Pro
1               5                   10                  15

Arg Gly Ser Ala Ala Leu Ala Leu Gly Val Ala Ala Pro Ala Ala
            20                  25                  30

Ala Pro Ala His Ser His Arg Asp Phe Glu Pro Val Leu His Leu Val
        35                  40                  45
```

Ala Leu Asn Ser Pro Leu Gly Gly Met Arg Gly Ile Arg Gly Ala Asp
         50                  55                  60

Phe Gln Cys Phe Gln Gln Ala Arg Ala Val Gly Leu Ala Gly Thr Phe
 65                  70                  75                  80

Arg Ala Phe Leu Ser Ser Arg Leu Gln Asp Leu Tyr Ser Ile Val Arg
                 85                  90                  95

Arg Ala Asp Arg Ala Ala Val Pro Ile Val Asn Leu Lys Asp Glu Leu
            100                 105                 110

Leu Phe Pro Ser Trp Glu Ala Leu Phe Ser Gly Ser Glu Gly Pro Leu
        115                 120                 125

Lys Pro Gly Ala Arg Ile Phe Ser Phe Asp Gly Lys Asp Val Leu Arg
    130                 135                 140

His Pro Thr Trp Pro Gln Lys Ser Val Trp His Gly Ser Asp Pro Asn
145                 150                 155                 160

Gly Arg Arg Leu Thr Glu Ser Tyr Cys Glu Thr Trp Arg Thr Glu Ala
                165                 170                 175

Pro Ser Ala Thr Gly Gln Ala Ser Ser Leu Leu Gly Gly Arg Leu Leu
            180                 185                 190

Gly Gln Ser Ala Ala Ser Cys His His Ala Tyr Ile Val Leu Cys Ile
        195                 200                 205

Glu Asn Ser Phe Met Thr Ala Ser Lys
    210                 215

<210> SEQ ID NO 34
<211> LENGTH: 639
<212> TYPE: DNA
<213> ORGANISM: Artificial Sequence
<220> FEATURE:
<223> OTHER INFORMATION: Description of Artificial Sequence: Synthetic
      His-JO-41 MTD-Endostatin cDNA Sequence

<400> SEQUENCE: 34
atgggcagca gcaaacatca tcatcatcac agcagcggcc tggtgccgcg cggcagccat      60
atggcggcgg cgctgctggc ggtggcgcac agccaccgcg acttccagcc ggtgctccac     120
ctggttgcgc tcaacagccc cctgtcaggc ggcatgcggg gcatccgcgg ggccgacttc     180
cagtgcttcc agcaggcgcg ggccgtgggg ctggcgggca ccttccgcgc cttcctgtcc     240
tcgcgcctgc aggacctgta cagcatcgtg cgccgtgccg accgcgcagc cgtgcccatc     300
gtcaacctca aggacgagct gctgtttccc agctgggagg ctctgttctc aggctctgag     360
ggtccgctga gcccggggc acgcatcttc cctttgacg caaggacgt cctgaggcac     420 cccacctggc cccagaagag cgtgtggcat ggctcggacc ccaacgggcg caggctgacc     480
gagagctact gtgagacgtg gcggacggag gctccctcgg ccacgggcca ggcctcctcg     540
ctgctggggg gcaggctcct ggggcagagt gccgcgagct gccatcacgc ctacatcgtg     600
ctctgcattg agaacagctt catgactgcc tccaagtag                            639

<210> SEQ ID NO 35
<211> LENGTH: 209
<212> TYPE: PRT
<213> ORGANISM: Artificial Sequence
<220> FEATURE:
<223> OTHER INFORMATION: Description of Artificial Sequence: Synthetic
      His-JO-41 MTD-Endostatin Amino Acid Sequence

<400> SEQUENCE: 35

Met Gly Ser Ser Lys His His His His His Ser Ser Gly Leu Val Pro
 1               5                  10                  15

```
Arg Gly Ser Ala Ala Ala Leu Leu Ala Val Ala His Ser His Arg Asp
            20                  25                  30

Phe Glu Pro Val Leu His Leu Val Ala Leu Asn Ser Pro Leu Gly Gly
        35                  40                  45

Met Arg Gly Ile Arg Gly Ala Asp Phe Gln Cys Phe Gln Gln Ala Arg
    50                  55                  60

Ala Val Gly Leu Ala Gly Thr Phe Arg Ala Phe Leu Ser Ser Arg Leu
65                  70                  75                  80

Gln Asp Leu Tyr Ser Ile Val Arg Arg Ala Asp Arg Ala Ala Val Pro
                85                  90                  95

Ile Val Asn Leu Lys Asp Glu Leu Leu Phe Pro Ser Trp Glu Ala Leu
            100                 105                 110

Phe Ser Gly Ser Glu Gly Pro Leu Lys Pro Gly Ala Arg Ile Phe Ser
        115                 120                 125

Phe Asp Gly Lys Asp Val Leu Arg His Pro Thr Trp Pro Gln Lys Ser
    130                 135                 140

Val Trp His Gly Ser Asp Pro Asn Gly Arg Arg Leu Thr Glu Ser Tyr
145                 150                 155                 160

Cys Glu Thr Trp Arg Thr Glu Ala Pro Ser Ala Thr Gly Gln Ala Ser
                165                 170                 175

Ser Leu Leu Gly Gly Arg Leu Leu Gly Gln Ser Ala Ala Ser Cys His
            180                 185                 190

His Ala Tyr Ile Val Leu Cys Ile Glu Asn Ser Phe Met Thr Ala Ser
        195                 200                 205

Lys
```

<210> SEQ ID NO 36
<211> LENGTH: 645
<212> TYPE: DNA
<213> ORGANISM: Artificial Sequence
<220> FEATURE:
<223> OTHER INFORMATION: Description of Artificial Sequence: Synthetic His-JO-135 MTD-Endostatin cDNA Sequence

<400> SEQUENCE: 36

```
atgggcagca gcaaacatca tcatcatcac agcagcggcc tggtgccgcg cggcagccat     60
atggcggcgg tggcgctgcc ggcggcggcg ccgcacagcc accgcgactt ccagccggtg    120
ctccacctgg ttgcgctcaa cagccccctg tcaggcggca tgcggggcat ccgcggggcc    180
gacttccagt gcttccagca ggcgcgggcc gtggggctgg cgggcacctt ccgcgccttc    240
ctgtcctcgc gcctgcagga cctgtacagc atcgtgcgcc gtgccgaccg cgcagccgtg    300
cccatcgtca acctcaagga cgagctgctg tttcccagct gggaggctct gttctcaggc    360
tctgagggtc cgctgaagcc cggggcacgc atcttctcct ttgacggcaa ggacgtcctg    420
aggcacccca cctggcccca gaagagcgtg tggcatggct cggaccccaa cgggcgcagg    480
ctgaccgaga gctactgtga gacgtggcgg acggaggctc cctcggccac gggccaggcc    540
tcctcgctgc tgggggcag gctcctgggg cagagtgccg cgagctgcca tcacgcctac     600
atcgtgctct gcattgagaa cagcttcatg actgcctcca agtag                    645
```

<210> SEQ ID NO 37
<211> LENGTH: 211
<212> TYPE: PRT
<213> ORGANISM: Artificial Sequence
<220> FEATURE:
<223> OTHER INFORMATION: Description of Artificial Sequence: Synthetic His-JO-135 MTD-Endostatin Amino Acid Sequence

<400> SEQUENCE: 37

```
Met Gly Ser Ser Lys His His His His Ser Ser Gly Leu Val Pro
1               5                   10                  15

Arg Gly Ser Ala Ala Val Ala Leu Pro Ala Ala Pro His Ser His
            20                  25                  30

Arg Asp Phe Glu Pro Val Leu His Leu Val Ala Leu Asn Ser Pro Leu
        35                  40                  45

Gly Gly Met Arg Gly Ile Arg Gly Ala Asp Phe Gln Cys Phe Gln
    50                  55                  60

Ala Arg Ala Val Gly Leu Ala Gly Thr Phe Arg Ala Phe Leu Ser Ser
65                  70                  75                  80

Arg Leu Gln Asp Leu Tyr Ser Ile Val Arg Arg Ala Asp Arg Ala Ala
            85                  90                  95

Val Pro Ile Val Asn Leu Lys Asp Glu Leu Leu Phe Pro Ser Trp Glu
            100                 105                 110

Ala Leu Phe Ser Gly Ser Glu Gly Pro Leu Lys Pro Gly Ala Arg Ile
            115                 120                 125

Phe Ser Phe Asp Gly Lys Asp Val Leu Arg His Pro Thr Trp Pro Gln
130                 135                 140

Lys Ser Val Trp His Gly Ser Asp Pro Asn Gly Arg Arg Leu Thr Glu
145                 150                 155                 160

Ser Tyr Cys Glu Thr Trp Arg Thr Glu Ala Pro Ser Ala Thr Gly Gln
                165                 170                 175

Ala Ser Ser Leu Leu Gly Gly Arg Leu Leu Gly Gln Ser Ala Ala Ser
            180                 185                 190

Cys His His Ala Tyr Ile Val Leu Cys Ile Glu Asn Ser Phe Met Thr
195                 200                 205

Ala Ser Lys
    210
```

<210> SEQ ID NO 38
<211> LENGTH: 651
<212> TYPE: DNA
<213> ORGANISM: Artificial Sequence
<220> FEATURE:
<223> OTHER INFORMATION: Description of Artificial Sequence: Synthetic His-JO-159 MTD-Endostatin cDNA Sequence

<400> SEQUENCE: 38

```
atgggcagca gcaaacatca tcatcatcac agcagcggcc tggtgccgcg cggcagccat      60
atgattgcga ttgcggcgat tccggcgatt ctggcgctgc acagccaccg cgacttccag     120
ccggtgctcc acctggttgc gctcaacagc cccctgtcag gcggcatgcg gggcatccgc     180
ggggccgact ccagtgctt ccagcaggcg cgggccgtgg gctggcggg caccttccgc       240
gccttcctgt cctcgcgcct gcaggacctg tacagcatcg tgcgccgtgc cgaccgcgca     300
gccgtgccca tcgtcaacct caaggacgag ctgctgtttc cagctggga ggctctgttc      360
tcaggctctg agggtccgct gaagcccggg gcacgcatct ctcctttga cggcaaggac      420
gtcctgaggc accccacctg gccccagaag agcgtgtggc atggctcgga ccccaacggg     480
cgcaggctga ccgagagcta ctgtgagacg tggcggacgg aggctccctc ggccacgggc     540
caggcctcct cgctgctggg gggcaggctc ctggggcaga gtgccgcgag ctgccatcac     600
gcctacatcg tgctctgcat tgagaacagc ttcatgactg cctccaagta g              651
```

<210> SEQ ID NO 39
<211> LENGTH: 213

```
<212> TYPE: PRT
<213> ORGANISM: Artificial Sequence
<220> FEATURE:
<223> OTHER INFORMATION: Description of Artificial Sequence: Synthetic
      His-JO-159 MTD-Endostatin Amino Acid Sequence

<400> SEQUENCE: 39
```

Met Gly Ser Ser Lys His His His His Ser Ser Gly Leu Val Pro
1               5                   10                  15

Arg Gly Ser Ile Ala Ile Ala Ala Ile Pro Ala Ile Leu Ala Leu His
                20                  25                  30

Ser His Arg Asp Phe Glu Pro Val Leu His Leu Val Ala Leu Asn Ser
            35                  40                  45

Pro Leu Gly Gly Met Arg Gly Ile Arg Gly Ala Asp Phe Gln Cys Phe
        50                  55                  60

Gln Gln Ala Arg Ala Val Gly Leu Ala Gly Thr Phe Arg Ala Phe Leu
65                  70                  75                  80

Ser Ser Arg Leu Gln Asp Leu Tyr Ser Ile Val Arg Arg Ala Asp Arg
                85                  90                  95

Ala Ala Val Pro Ile Val Asn Leu Lys Asp Glu Leu Leu Phe Pro Ser
                100                 105                 110

Trp Glu Ala Leu Phe Ser Gly Ser Glu Gly Pro Leu Lys Pro Gly Ala
            115                 120                 125

Arg Ile Phe Ser Phe Asp Gly Lys Asp Val Leu Arg His Pro Thr Trp
        130                 135                 140

Pro Gln Lys Ser Val Trp His Gly Ser Asp Pro Asn Gly Arg Arg Leu
145                 150                 155                 160

Thr Glu Ser Tyr Cys Glu Thr Trp Arg Thr Glu Ala Pro Ser Ala Thr
                165                 170                 175

Gly Gln Ala Ser Ser Leu Leu Gly Gly Arg Leu Leu Gly Gln Ser Ala
                180                 185                 190

Ala Ser Cys His His Ala Tyr Ile Val Leu Cys Ile Glu Asn Ser Phe
            195                 200                 205

Met Thr Ala Ser Lys
        210

```
<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      HE-5' forward primer

<400> SEQUENCE: 40
ccgcatatgc acagccaccg cgacttccag ccggtg                        36

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      HE-3' reverse primer

<400> SEQUENCE: 41
ccgcatatgc tacttggagg cagtcatgaa gctgtt                        36

<210> SEQ ID NO 42
<211> LENGTH: 63
<212> TYPE: DNA
```

<213> ORGANISM: Artificial Sequence
<220> FEATURE:
<223> OTHER INFORMATION: Description of Artificial Sequence: Synthetic
      HM1E-5' forward primer

<400> SEQUENCE: 42
ccgcatatgg tgctgctggc ggcggcgctg attgcgcaca gccaccgcga cttccagccg    60
gtg                                                                  63

<210> SEQ ID NO 43
<211> LENGTH: 63
<212> TYPE: DNA
<213> ORGANISM: Artificial Sequence
<220> FEATURE:
<223> OTHER INFORMATION: Description of Artificial Sequence: Synthetic
      HEM1-3' reverse primer

<400> SEQUENCE: 43
ccgcatatgc tacgcaatca gcgccgccgc cagcagcacc ttggaggcag tcatgaagct    60
gtt                                                                  63

<210> SEQ ID NO 44
<211> LENGTH: 60
<212> TYPE: DNA
<213> ORGANISM: Artificial Sequence
<220> FEATURE:
<223> OTHER INFORMATION: Description of Artificial Sequence: Synthetic
      HM2E-5' forward primer

<400> SEQUENCE: 44
ccgcatatgc cggtgctgct gctgctggcg ccgcacagcc accgcgactt ccagccggtg    60

<210> SEQ ID NO 45
<211> LENGTH: 60
<212> TYPE: DNA
<213> ORGANISM: Artificial Sequence
<220> FEATURE:
<223> OTHER INFORMATION: Description of Artificial Sequence: Synthetic
      HEM2-3' reverse primer

<400> SEQUENCE: 45
ccgcatatgc tacggcgcca gcagcagcag caccggcttg gaggcagtca tgaagctgtt    60

<210> SEQ ID NO 46
<211> LENGTH: 66
<212> TYPE: DNA
<213> ORGANISM: Artificial Sequence
<220> FEATURE:
<223> OTHER INFORMATION: Description of Artificial Sequence: Synthetic
      HM3E-5' forward primer

<400> SEQUENCE: 46
ccgcatatgg cggcggcgct ggcggcgatt gcggtgattc acagccaccg cgacttccag    60
ccggtg                                                               66

<210> SEQ ID NO 47
<211> LENGTH: 63
<212> TYPE: DNA
<213> ORGANISM: Artificial Sequence
<220> FEATURE:
<223> OTHER INFORMATION: Description of Artificial Sequence: Synthetic
      HM4E-5' forward primer

<400> SEQUENCE: 47
ccgcatatgg cgctggcgct gctgctgctg gtgccgcaca gccaccgcga cttccagccg    60

-continued gtg                                                                63

<210> SEQ ID NO 48
<211> LENGTH: 69
<212> TYPE: DNA
<213> ORGANISM: Artificial Sequence
<220> FEATURE:
<223> OTHER INFORMATION: Description of Artificial Sequence: Synthetic
      HM5E-5' forward primer

<400> SEQUENCE: 48
ccgcatatgc tgctggcggc ggcggcggcg ctgctgctgg cgcacagcca ccgcgacttc    60
cagccggtg                                                           69

<210> SEQ ID NO 49
<211> LENGTH: 84
<212> TYPE: DNA
<213> ORGANISM: Artificial Sequence
<220> FEATURE:
<223> OTHER INFORMATION: Description of Artificial Sequence: Synthetic
      HM6E-5' forward primer

<400> SEQUENCE: 49
ccgcatatgg cggcgctggc gctgggcgtg gcggcggcgc cggcggcggc gccggcgcac    60
agccaccgcg acttccagcc ggtg                                          84

<210> SEQ ID NO 50
<211> LENGTH: 60
<212> TYPE: DNA
<213> ORGANISM: Artificial Sequence
<220> FEATURE:
<223> OTHER INFORMATION: Description of Artificial Sequence: Synthetic
      HM7E-5' forward primer

<400> SEQUENCE: 50
ccgcatatgg cggcggcgct gctggcggtg gcgcacagcc accgcgactt ccagccggtg    60

<210> SEQ ID NO 51
<211> LENGTH: 66
<212> TYPE: DNA
<213> ORGANISM: Artificial Sequence
<220> FEATURE:
<223> OTHER INFORMATION: Description of Artificial Sequence: Synthetic
      HM8E-5' forward primer

<400> SEQUENCE: 51
ccgcatatgg cggcggtggc gctgccggcg gcggcgccgc acagccaccg cgacttccag    60
ccggtg                                                              66

<210> SEQ ID NO 52
<211> LENGTH: 72
<212> TYPE: DNA
<213> ORGANISM: Artificial Sequence
<220> FEATURE:
<223> OTHER INFORMATION: Description of Artificial Sequence: Synthetic
      HM9E-5' forward primer

<400> SEQUENCE: 52
ccgcatatga ttgcgattgc ggcgattccg gcgattctgg cgctgcacag ccaccgcgac    60
ttccagccgg tg                                                       72

<210> SEQ ID NO 53
<211> LENGTH: 6
<212> TYPE: PRT
<213> ORGANISM: Artificial Sequence -continued

```
<220> FEATURE:
<223> OTHER INFORMATION: Description of Artificial Sequence: Synthetic
      6xHis tag

<400> SEQUENCE: 53

His His His His His His
1               5
```